US012582466B2

(12) United States Patent
Werneth et al.

(10) Patent No.: US 12,582,466 B2
(45) Date of Patent: Mar. 24, 2026

(54) ABLATION ASSEMBLY TO TREAT TARGET REGIONS OF TISSUE IN ORGANS

(71) Applicant: Arga' Medtech SA, Chardonne (CH)

(72) Inventors: Randell L. Werneth, San Diego, CA (US); David Zarbatany, Laguna Niguel, CA (US); Ricardo David Roman, Chula Vista, CA (US)

(73) Assignee: Argá Medtech SA, Epalinges (CH)

( * ) Notice: Subject to any disclaimer, the term of this patent is extended or adjusted under 35 U.S.C. 154(b) by 967 days.

(21) Appl. No.: 17/686,001

(22) Filed: Mar. 3, 2022

(65) Prior Publication Data

US 2022/0183752 A1 Jun. 16, 2022

Related U.S. Application Data

(63) Continuation of application No. PCT/IB2020/058173, filed on Sep. 2, 2020.

(Continued)

(51) Int. Cl.

*A61B 18/14* (2006.01)
*A61B 5/283* (2021.01)

(Continued)

(52) U.S. Cl.

CPC .......... *A61B 18/1492* (2013.01); *A61B 5/283* (2021.01); *A61B 18/1206* (2013.01);

(Continued)

(58) Field of Classification Search

CPC .... A61N 1/362; A61N 7/022; A61B 18/1206; A61B 18/1492; A61B 2018/0016;

(Continued)

(56) References Cited

U.S. PATENT DOCUMENTS 5,807,324 A * 9/1998 Griffin, III ......... A61B 18/1492 607/116
5,882,346 A * 3/1999 Pomeranz .......... A61B 18/1492 604/510

(Continued)

FOREIGN PATENT DOCUMENTS

CN 205866827 U 1/2017
JP 2018517494 A 7/2018

(Continued)

OTHER PUBLICATIONS

Davalos , et al., "Tissue Ablation with Irreversible Electroporation", Annals of Biomedical Engineering, Feb. 2005, 9 pgs.

(Continued)

*Primary Examiner* — Tigist S Demie
(74) *Attorney, Agent, or Firm* — Bookoff McAndrews, PLLC

(57) ABSTRACT

The present invention relates to an ablation assembly to treat target regions of a tissue in organs comprising:

an ablation catheter comprising an elongate shaft having a longitudinal main direction (X-X), said elongate shaft comprising at least a shaft distal portion, said shaft distal portion comprising a shaft distal portion distal end;

said ablation catheter comprising an inner lumen arranged within the elongate shaft;

said ablation catheter comprising a shaft ablation assembly fixedly disposed at said shaft distal portion, the shaft ablation assembly being configured to deliver both thermal energy for ablating said tissue and non-thermal energy for treating said tissue;

at least a shape setting mandrel disposed within the ablation catheter, the shape setting mandrel being insertable within the inner lumen and removable from the inner lumen, (Continued)

wherein the shape setting mandrel is free to move in respect of the inner lumen avoiding any constraint with said shaft distal portion during the shape setting mandrel insertion,
wherein the shape setting mandrel comprises at least a pre-shaped configuration and the shape setting mandrel is reversibly deformable between at least a straight loaded configuration and said pre-shaped configuration,
wherein, when the shape setting mandrel is fully inserted in the shaft distal portion, the shape setting mandrel is configured to shape set said shaft distal portion with said pre-shaped configuration.

14 Claims, 36 Drawing Sheets

Related U.S. Application Data

(60) Provisional application No. 62/897,200, filed on Sep. 6, 2019, provisional application No. 62/895,658, filed on Sep. 4, 2019.

(51) Int. Cl.
*A61B 18/12* (2006.01)
*A61B 18/00* (2006.01)

(52) U.S. Cl.
CPC ............... *A61B 2018/00351* (2013.01); *A61B 2018/00577* (2013.01); *A61B 2018/00613* (2013.01); *A61B 2018/00767* (2013.01); *A61B 2018/0091* (2013.01); *A61B 2018/1226* (2013.01); *A61B 2018/1253* (2013.01); *A61B 2018/126* (2013.01); *A61B 2018/1417* (2013.01); *A61B 2018/1435* (2013.01)

(58) Field of Classification Search
CPC A61B 2018/00196; A61B 2018/00351; A61B 2018/00577; A61B 2018/00613; A61B 2018/00702; A61B 2018/00726; A61B 2018/00761; A61B 2018/00767; A61B 2018/00839; A61B 2018/00886; A61B 2018/0091; A61B 2018/0212; A61B 2018/1226; A61B 2018/124; A61B 2018/1253; A61B 2018/126; A61B 2018/1266; A61B 2018/1273; A61B 2018/1407; A61B 2018/1417; A61B 2018/1435; A61B 5/283; A61B 5/4836; A61B 5/6855; A61B 5/6856; A61B 5/6857
See application file for complete search history.

(56) References Cited

U.S. PATENT DOCUMENTS

| | | | | |
|---|---|---|---|---|
| 7,101,362 | B2 | 9/2006 | Vanney | |
| 7,311,705 | B2 | 12/2007 | Sra | |
| 8,221,411 | B2 | 7/2012 | Francischelli et al. | |
| 8,475,449 | B2 | 7/2013 | Werneth et al. | |
| 8,540,710 | B2 | 9/2013 | Johnson et al. | |
| 8,641,704 | B2 | 2/2014 | Werneth et al. | |
| 8,948,865 | B2 | 2/2015 | Zarins et al. | |
| 2002/0177765 | A1 | 11/2002 | Bowe et al. | |
| 2008/0281314 | A1 | 11/2008 | Johnson et al. | |
| 2009/0149848 | A1 * | 6/2009 | Werneth | A61B 18/18 606/41 |
| 2010/0152725 | A1 | 6/2010 | Pearson et al. | |
| 2012/0130218 | A1 * | 5/2012 | Kauphusman | A61B 5/6852 600/585 |
| 2015/0327994 | A1 | 11/2015 | Morriss et al. | |
| 2016/0051324 | A1 | 2/2016 | Stewart et al. | |
| 2018/0085160 | A1 | 3/2018 | Viswanathan et al. | |
| 2018/0161092 | A1 * | 6/2018 | Greifeneder | A61B 18/1492 |
| 2018/0214202 | A1 | 8/2018 | Howard et al. | |
| 2019/0038171 | A1 | 2/2019 | Howard | |
| 2019/0201688 | A1 | 7/2019 | Olson | |
| 2020/0229866 | A1 | 7/2020 | Harlev et al. | |

FOREIGN PATENT DOCUMENTS

| | | |
|---|---|---|
| WO | 2017192804 | 11/2017 |
| WO | 2019023280 | 1/2019 |
| WO | 2021044312 | 3/2021 |

OTHER PUBLICATIONS

Ellis , et al., "Radiofrequency Ablation for Cancer", Springer, 2004, 310 pgs.
Chinese Office Action issued on May 11, 2024, in corresponding Chinese Application No. 202080074201X (27 pages, with English translation).
Heller , et al., "Gene Electrotransfer Clinical Trials", Advances in Genetics, vol. 89, 2015, 28 pgs.
Neumann , et al., "Gene transfer into mouse lyoma cells by electroporation in high electric fields", EMBO Journal, vol. 1, No. 7, 1982, 5 pgs.
WIPO, International Search Report and Written Opinion mailed Nov. 6, 2020, in PCT/IB2020/058173, 13 pgs.
Mali , et al., "Antitumor effectiveness of electrochemotherapy: A systematice review and meta-analysis", EJSO 39, Sep. 11, 2012, 13.

* cited by examiner

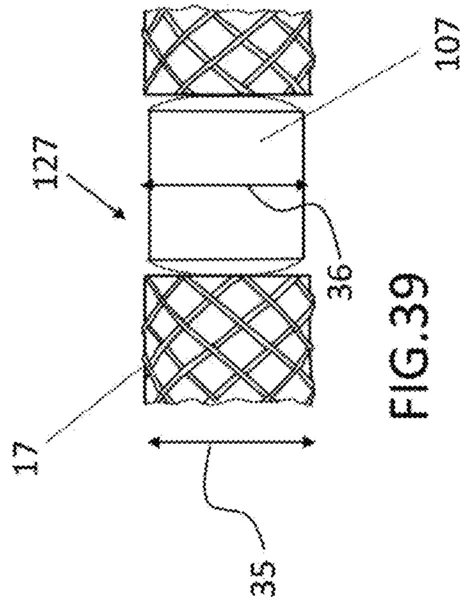
FIG.39
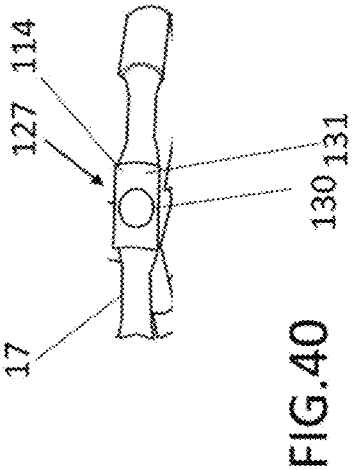
FIG.40
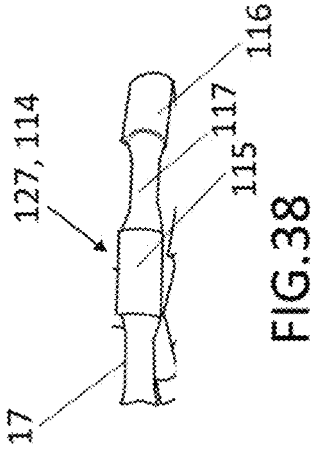
FIG.38
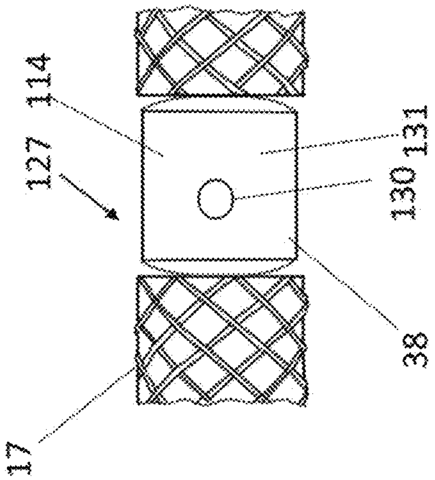

14
18
1
17
19

14
126
1
27
17

14
126
1
27
17
126

ABLATION ASSEMBLY TO TREAT TARGET REGIONS OF TISSUE IN ORGANS

CROSS-REFERENCE TO RELATED APPLICATIONS

This application is a continuation of PCT/IB2020/058173, filed Sep. 2, 2020, which claims priority to U.S. Provisional Patent Application No. 62/895,658, filed Sep. 4, 2019, and U.S. Provisional Patent Application No. 62/897,200, filed Sep. 6, 2019, the disclosures of which are hereby incorporated by reference.

FIELD OF THE INVENTION

The present invention relates to ablation equipment or assemblies to treat target regions of tissue in organs systems and methods for treating target regions of tissue in organs.

More particularly, the present invention relates to a combination system and method for non-thermally treating target tissue and thermally ablating tissue. Said tissue would be that which is either diseased such as in atrial fibrillation (or AF) patient where the cardiac cell action potential is not normal, typically phase phases 0-3. Said tissue could also be tissue where it is deemed necessary to block a refractory wave-front to stop or prevent irregular arrhythmias in patients.

The present invention relates generally to ablation systems and methods for performing targeted tissue ablation in a patient. In particular, the present invention provides catheters which deliver radiofrequency (RF) and/or Irreversible electroporation (IRE) which occurs when a strong, pulsed electrical field (PEF) causes permeabilization of the cell membrane, leading to cellular homeostasis disruption and cell death. Irreversible Electroporation (IRE) energies that create safe, precision lesions in targeted tissue such as that cause heart arrhythmias.

BACKGROUND ART

Applications of PEF in cardiology are vast and include atrial fibrillation, ventricular fibrillation, septal ablation, and targeting vascular structures. PEF has appealing characteristics including ability to be tissue specific and non-thermal. This invention provides for a novel catheter design to delivery IRE/PEF to cardiac tissue.

Pulsed electric fields (PEF) refer to application of intermittent, high-intensity electric fields for short periods of time (micro- or nanoseconds), which results in cellular and tissue electroporation. Electroporation is a process whereby an applied electric field (i.e. PEF) results in formation of pores in cell membranes. Pore formation leads to permeabilization, which can be reversible or irreversible, depending upon parameters of the applied PEF. In reversible electroporation, cells remain viable, and underlies the basis of electrochemotherapy and gene electrotransfer. See references 1) Mali B, Jarm T, Snoj M, Sersa G, Miklavcic D. Antitumor effectiveness of electrochemotherapy: A systematic review and meta-analysis. Eur J Surg Oncol. 2013; 39:4-16; 2) 2) Heller R, Heller L C. Gene Electrotransfer Clinical Trials. Adv Genet. 2015; 89:235-62; 3) Neumann E, Schaefer-Ridder M, Wang Y, Hofschneider P. Gene transfer into mouse lyoma cells by electroporation in high electric fields. EMBO J. 1982; 1:841-5.

Electroporation is a phenomenon whereby PEF (created by high voltage currents) are applied to a cell resulting in pore formation in the cell membrane with a subsequent increase in cell permeability. The electric field is most commonly produced by high voltage direct current delivered between two or more electrodes. When electric fields are applied, charge is established across the lipid bilayer and, once a critical threshold is reached (dependent on transmembrane voltage), electroporation occurs. In contrast, with irreversible electroporation (IRE), cells and tissue are non-viable because of programmed cell death cascade activation. IRE is a well-established treatment for solid tumors. However, PEFs may also be useful in cardiology, particularly for cardiac ablation, given limitations of current thermal based approaches. PEF can create lesions without tissue heating, and be cell/tissue selective which enables preservation of critical surrounding structures.

Tissue ablation is used in numerous medical procedures to treat a patient. Ablation can be performed to remove or denature undesired tissue such as diseased cardiac cells. Ablation procedures may also involve the modification of the tissue without removal, such as to stop electrical function in a particular area in the chain of electrical propagation through the heart tissue in patients with an arrhythmia condition. The ablation can be performed by passing energy, such as electrical energy, through one or more electrodes and causing tissue death where the electrodes are in contact. Ablation procedures can be performed on patients with any cardiac arrythmia such as atrial fibrillation (AF) by ablating tissue in the heart.

Mammalian organ function typically occurs when electrical activity is spontaneously generated by the SA node, the cardiac pacemaker. This electrical impulse is propagated throughout the right atrium, and through Bachmann's bundle to the left atrium, stimulating the myocardium of the atria to contract. The conduction system consists of specialized heart muscle cells. Cardiac myocardial cell has a negative membrane potential when at rest. Stimulation above a threshold value induces the opening of voltage-gated ion channels and a flood of cations into the cell. The positively charged ions entering the cell cause the depolarization characteristic of an action potential. Like skeletal muscle, depolarization causes the opening of voltage-gated calcium channels and release of Ca2+ from the t-tubules. This influx of calcium causes calcium-induced calcium release from the sarcoplasmic reticulum, and free Ca2+ causes muscle contraction. After a delay, potassium channels reopen, and the resulting flow of K+ out of the cell causes repolarization to the resting state. This transmission of electrical impulses propagates through the heart chamber. A disturbance of such electrical transmission may lead to organ malfunction. One particular area where electrical impulse transmission is critical for proper organ function is in the heart, resulting in atrial contractions which leads to the pumping of blood into the ventricles in a manner synchronous with the pulse.

Atrial fibrillation (AF) refers to a type of cardiac arrhythmia where there is disorganized electrical conduction in the atria causing rapid uncoordinated atrial contractions that result in ineffective pumping of blood into the ventricle as well as a lack of synchrony. During AF, the atrioventricular node receives electrical impulses from numerous locations throughout the atria instead of only from the sinus node. These aberrant signals overwhelm the atrioventricular node, producing an irregular and rapid heartbeat. As a result, blood may pool in the atria, increasing the likelihood of blood clot formation. The major risk factors for AF include age, coronary artery disease, rheumatic heart disease, hypertension, diabetes, and thyrotoxicosis. AF affects 7% of the population over age 65.

Atrial fibrillation treatment options are limited. Lifestyle changes only assist individuals with lifestyle related AF. Medication therapy manages AF symptoms, often presents side effects more dangerous than AF, and fails to cure AF. Electrical cardioversion attempts to restore a normal sinus rhythm, but has a high AF recurrence rate due to disease progression. In addition, if there is a blood clot in the atria, cardioversion may cause the clot to leave the heart and travel to the brain (causing a stroke) or to some other part of the body. What are needed are new methods for treating AF and other medical conditions involving disorganized electrical conduction.

Various ablation techniques have been proposed to treat AF, including the Cox-Maze ablation procedure, linear ablation of various regions of the atrium, and circumferential ablation of pulmonary vein ostia. The Cox-Maze ablation procedure and linear ablation procedures are tedious and time-consuming, taking several hours to accomplish. Current pulmonary vein ostial ablation is proving to be ineffective long-term. All ablation procedures involve the risk of inadvertently damaging untargeted tissue, such as the esophagus while ablating tissue in the left atrium of the heart.

There is therefore a need for improved atrial ablation products and techniques that create efficacious lesions in a safe manner.

Solutions are known in the following documents: U.S. Pat. No. 8,641,704B2, U.S. Pat. No. 8,475,449B2, US2010152725A1, US2010152725A1, U.S. Pat. No. 8,948,865B2, US2008281314A1, U.S. Pat. No. 8,540,710B2, US2019038171A1, U.S. Pat. No. 8,221,411B2, US2016051324A1, US2015327994A1, WO2017192804A1, US2020229866A1, WO2019023280A1.

In many of these procedures an energy delivery device, such as a probe with or without a needle, is inserted into a target tissue to cause destruction of a target region of the cardiac tissue through the application of energy, such as thermal energy, non-thermal energy, and energy associated with cryo ablation procedures. The insertion of the energy delivery device into the heart chamber or other organs is accomplished by an elongated track which is typically created from points inferior to the heart. An elongated track or access tube is defined as the space created by the insertion of a device extending from the point of skin puncture to the target tissue. When the energy delivery device is removed, it is pulled back along the elongated track or access tube that had been previously created to allow insertion of the energy delivery device.

Prior to delivery device being withdrawn, the tissue immediately adjacent to the energy delivery device is ablated. This can produce a focalized zone around the ablation elements, maximizing the chance of death in the desired tissue location. It is known in the art that electrically induced thermal ablation such as RF can be used to effectively and continuously locally ablate a tissue site as an energy delivery device is placed on the tissue surface. RF can lead to coagulation necrosis in a margin surrounding normal tissue where hyperthermic conditions lead to cellular injury such as coagulation of cytosolic enzymes and damage to histone complexes, leading to ultimate cell death. Although these tissue treatment methods and systems can effectively ablate volumes of target tissue, there are limitations to each technique. One often cited problem using these procedures during cardiac ablation involves heat sink, a process whereby one aspect can include blood flow whereas the heat generated on the ablation element will be removed/dissipated by the cooler blood flows over the element. This heat dissipation effect can change both the shape and maximum volume of the tissue being ablated. After treatment of a target tissue region with an energy delivery device, upon removal of the energy delivery device from the targeted tissue region, the energy delivery device can be placed in a new, un-ablated site needing treatment.

More recently, irreversible electroporation (IRE) has been used as an alternative to the above-mentioned procedures to ablate cardiac or organ tissue. However, though IRE can be a non-thermal method causing cell death, it is not ideal for coagulation, and specifically does not cause electrically induced thermal coagulation, demonstrating the importance of using an alternative source such as RF or long DC pulses in heating a tissue site. Instead, IRE involves the application of electrical pulses to targeted tissue in the range of microseconds to milliseconds that can lead to non-thermally produced defects in the cell membrane that are nanoscale in size. These defects can lead to a disruption of homeostasis of the cell membrane, thereby causing irreversible cell membrane permeabilization which induces cell necrosis, without raising the temperature of the tissue ablation zone. During IRE ablation, connective tissue and scaffolding structures are spared, thus allowing the surrounding organs, structures, blood vessels, and connective tissue to remain intact. With nonthermal IRE (hereinafter also called non-thermal IRE), cell death is mediated through a nonthermal mechanism, so the heat sink problem associated with many ablation techniques is nullified. Therefore the advantages of IRE to allow focused treatment with tissue sparing and without thermal effects can be used effectively in conjunction with thermal treatment such as RF that has been proven effective to prevent ablation site bleeding; this will also allow (in this example embodiment) the user to utilize determined RF levels leading to in some cases ablation and in some cases coagulation; this is important since IRE will not effectively coagulate when dealing with large tissue regions. In this way the newly discovered advantages of IRE can be utilized effectively with known techniques of non-thermal damage with the added advantage of either selecting to use RF or no RF in conjunction.

Although IRE has distinct advantages, there are also advantages of utilizing thermal ablation during treatment procedures. Prior to the disclosure of this invention, an invention had not been proposed that could solve the problems of nonthermally ablating a target region of cardiac or organ tissue, while maintaining integrity of the surrounding tissue, and effectively switching to a device for effectively thermally ablating tissue along the ablation track. In certain proposed embodiments, an energy delivery device can be utilized that is powered by a single energy source that is capable of application of energy in various forms, and subsequently ablating a tissue track during a medical procedure for the treatment of arrhythmias using the same energy delivery device that can be powered by a different form of energy from the same energy source, to maximize procedure outcomes. As indicated, IRE provides advantages for nonthermal cell death and thermal mechanisms provide advantages for not only preventing seeding, but also for effectively bringing about coagulation. A need exists for a system and method that can provide this combined non-thermal/thermal tumor ablation and that allows for switching between non-thermal IRE energy delivery and thermal energy delivery to increase tumor ablation efficiency and efficacy and the prevention of tissue track.

Nevertheless, it is therefore still strongly felt the need to simplifying the tissue, especially the heart tissue, speeding up treatment and reducing intervention times.

Solution

This invention provides for a novel assembly or equipment and method to delivery non-thermal and thermal energies to cardiac tissue.

A unique multi-electrode and multi-functional ablation catheter and ablation catheter systems, or ablation assembly or equipment 100, and methods are provided which map and ablate myocardial tissue within the heart chambers of a patient. Any electrocardiogram signal site (e.g. a site with aberrant signals) or combination of multiple sites that are discovered with this placement may be ablated. In alternative embodiments, the ablation catheters and systems may be used to treat non-cardiac patient tissue, such as tumor tissue, renal artery nerves, etc.

According to alternative embodiments, an probe, e.g. an ablation catheter 1 for performing a medical procedure on a patient is provided. The ablation catheter 1 comprises an elongate shaft 13 with a proximal portion 14 including a proximal end 15 and a distal end 16, and a distal portion 17 with a proximal end 18 and a distal end 19. The elongate shaft 13 further comprises a shaft ablation assembly 20 and a distal ablation assembly 21 configured to deliver energy, such as RF and/or Irreversible Electroporation energy, to tissue 41. The shaft ablation assembly 20 is proximal to the distal end of the distal portion 19, and includes at least one shaft ablation element 22, or shaft electrode 127, fixedly or removable attached to the shaft 13 and configured to deliver ablation energy to tissue. The distal ablation assembly 21 is at the distal end of the distal portion 19 and includes at least one tip ablation element 23, or electrode tip 128, configured to deliver ablation energy to tissue.

According to alternative embodiments, the distal portion 17 is configured to be in a circular configuration and can deflected in one or more directions, in one or more deflection shapes and geometries 24. The deflection geometries 24 may be similar or symmetric deflection geometries, or the deflection geometries may be dissimilar or asymmetric deflection geometries. The shaft, or ablation catheter 1, may include one or more steering wires 25 configured to deflect the distal portion 17 in the one or more deflection directions. The catheter deflection can also occur by placing or removing a shape setting mandrel 26. The elongate shaft 13 may include difference is the stiffness of the shaft along its length. The elongate shaft 13 may include a shape setting mandrel 26 within the shaft, or ablation catheter 1, the shape setting mandrel 26 configured to perform or enhance the deflection (steering and shape) of the distal portion 17, such as to maintain deflections in a single plane. The shaft, or ablation catheter, may include variable material properties such as a asymmetric joint 27 between two portions, an integral member 28 within a wall or fixedly attached to the shaft, a variable braid 29 or other variation used to create multiple deflections, such as deflections with asymmetric deflection geometries.

According to alternative embodiments, the distal ablation assembly 21 may be fixedly attached to the distal end of the distal portion 19, or it may be advanceable from the distal shaft 17, such as via a control port 30. The distal ablation assembly 21 may comprise a single ablation element 31, such as an electrode, or tip ablation element 23 or electrode tip 128, or multiple ablation elements 32, or mandrel electrodes 132. The distal ablation assembly 21 may include a shape setting mandrel carrier assembly 33 of ablation elements, or simply shape setting mandrel 26, and the shape setting mandrel carrier assembly 33 may be changeable from a compact geometry to an expanded geometry, such transition caused by advancement and/or retraction of a control shaft.

According to alternative embodiments, the shaft ablation assembly 20 may include a single ablation element 31 or multiple ablation elements 32, or shaft electrodes 127, preferably five to ten ablation elements fixedly attached to the shaft or shape setting mandrel. The ablation elements may have a profile that is flush with the surface of the shaft, or more preferably the shaft between the electrode elements outer diameter 35, or shaft outer diameter 35, is slightly smaller than the diameter of the ablation electrodes 36, or shaft electrodes outer diameter 36, such that the distal end of the catheter is more flexible.

According to alternative embodiments, the ablation elements 31, 32, 127, 128, 132 of the present invention can deliver one or more forms of energy, preferably RF and/or Irreversible Electroporation energy. The ablation elements may have similar or dissimilar construction, and may be constructed in various sizes and geometries. The ablation elements may include one or more thermocouples 37, such as two thermocouples mounted 90° from each other on the inside of an ablation element. The ablation elements may include means of dissipating heat 38, such as increased surface area. According to alternative embodiments, one or more ablation elements is configured in a tubular geometry, and the wall thickness to outer diameter approximates a 1:15 ratio. According to alternative embodiments, one or more ablation elements is configured to record, or map electrical activity in tissue such as mapping of cardiac electrograms. According to alternative embodiments, one or more ablation elements is configured to deliver pacing energy, such as to energy delivered to pace the heart of a patient.

According to alternative embodiments, the ablation catheters of the present invention may be used to treat one or more medical conditions by delivering ablation energy to tissue. Conditions include an arrhythmia of the heart, cancer, and other conditions in which removing or denaturing tissue improves the patient's health.

According to alternative embodiments, a kit of ablation catheters, or ablation catheter kit 300, is provided. A first ablation catheter 1 has a distal portion which can be deflected in at least two symmetric geometries. A second ablation catheter 1' has a distal portion which can be deflected in at least two asymmetric geometries.

According to alternative embodiments, a method of treating proximal, persistent or long-standing persistent atrial fibrillation is provided. An ablation catheter of the present invention 1 may be placed in the coronary sinus of the patient, such as to map electrograms and/or ablate tissue, and subsequently placed in the left or right atrium to map electrograms and/or ablate tissue. The ablation catheter may be placed to ablate one or more tissue locations including but not limited to: fasicals around a pulmonary vein; the left atrial roof, and the mitral isthmus.

According to alternative embodiments, a method of treating atrial flutter is provided. An ablation catheter of the present invention may be used to achieve bi-directional block, such as by placement in one or more locations in the right atrium of the heart 43.

According to alternative embodiments, a method of ablating tissue in the right atrium of the heart is provided. An ablation catheter of the present invention may be used to: create lesions between the superior vena cava and the inferior vena cava; the coronary sinus and the inferior vena cava; the superior vena cava and the coronary sinus; and combinations of these. The catheter can be used to map electrograms and/or map and/or ablate the sinus node, such as to treat sinus node tachycardia.

According to alternative embodiments, a method of treating ventricular tachycardia is provided. An ablation catheter of the present invention may be placed in the left or right ventricles of the heart, induce ventricular tachycardia by delivering pacing energy, and ablating tissue to treat the patient.

According to alternative embodiments, an ablation catheter with a first geometry larger than a second deflection geometry is provided via the shape setting mandrel. The ablation catheter is placed in the smaller second shape geometry to ablate one or more of the following tissue locations: left atrial septum; tissue adjacent the left atrial septum; and tissue adjacent the left atrial posterior wall. The ablation catheter is placed in the larger first geometry to ablate at least the circumference around the pulmonary veins.

According to alternative embodiments, an ablation catheter of the present invention is used to treat both the left and right atria of a heart. The catheter is configured to transition to a geometry with a first shape setting mandrel and/or deflection geometry and a second shape setting mandrel and/or deflection geometry, where the first geometry is different than the second geometry. The catheter is used to ablate tissue in the right atrium using at least the first geometry and also ablate tissue in the left atrium using at least the second geometry.

According to alternative embodiments, a catheter for performing a medical procedure on a patient is provided. The catheter, or catheter assembly or equipment 100, comprises an elongate shaft with a proximal portion including a proximal end and a distal end, and a distal portion with a proximal end and a distal end. The catheter further comprises a shape setting mandrel and/or deflection assembly configured to shape the distal portion in a first direction in a first geometry and a second direction in a second geometry, wherein the first and second geometries are different. The catheter further includes a functional element fixedly mounted to the distal portion.

According to alternative embodiments, a combination treatment system that has at least one energy delivery device, or ablation catheter 1, and at least one power or energy or power source, or single power source 4, that is capable of providing IRE energy and thermal energy to the energy delivery device is provided. The at least one energy delivery device can be either a monopolar or bipolar device. The system can continuously modify the energy or power source from energy utilized in a nonthermal form to energy in a thermal form to ablate target regions of tissue as well as tissue along a track.

According to alternative embodiments, a method that involves using non-thermal IRE energy and thermal energy to effectively ablate target regions of tissue is provided. The method involves positioning at least one energy delivery device that is coupled to a single power source within a target region of a tissue, applying IRE energy from the power source to the energy delivery device which is used to ablate a target region of tissue, while preventing damage to surrounding structures, then switching from IRE energy to thermal energy using the same power source, and positioning the energy delivery device while ablating said tissue with thermal energy such as RF energy, to allow for focal tissue ablation and the safe energy delivery used during the treatment procedure, while among other things, coagulating tissue and preventing bleeding.

According to alternative embodiments, what is described herein is a system and method for selectively ablating tissue 3, the system 3 comprising an ablation catheter 1 and a single power source 4.

According to alternative embodiments, the method involves providing application of IRE to ablate and or treat tissue and treatment of tissue with an alternative energy form (such as thermal energy) to effectively ablate tissue from the same ablation device and the same energy source. The method can involve providing at least one energy source, or single power source 4, which has at least a non-thermal energy source 6 and a thermal energy source 7, providing at least one probe, or ablation catheter 1, that is configured to be selectively operatively coupled to a desired energy source of the at least one energy source, positioning via a probe at least a portion of the at least one probe within a desired region of a heart or organ, selectively coupling the at least one probe to the non-thermal energy source, selectively energizing the non-thermal energy source to apply non-thermal energy from the non-thermal energy source to at least a portion of the desired region to ablate at least a portion of the desired region, selectively coupling the at least one probe to the thermal energy source, withdrawing the at least probe from the desired region, and selectively energizing the thermal energy source to apply thermal energy during at least a portion of withdrawal of the at least one probe to ablate tissue substantially adjacent to the probe track.

According to alternative embodiments, a system for selectively ablating tissue 3 is provided herein that has at least one energy source, or single power source 4, that has a non-thermal energy source 6 and a thermal energy source 7, at least one probe, or ablation catheter 1, a means for selectively coupling 8 the probe to one desired energy source of the at least one energy source means for selectively energizing the non-thermal energy source 11 of the at least one energy source to apply non-thermal energy to at least a portion of the desired region to ablate at least a portion of the desired region, and means for selectively energizing the thermal energy source 12 of the at least one energy source during the withdrawal of the at least one probe to thermally ablate tissue substantially adjacent to a probe track.

Therefore, it is the object of the present invention to provide an ablation assembly having structural and functional features such as to meet the aforementioned needs and overcome the drawbacks mentioned above with reference to the devices of the prior art.

These and other objects are achieved by a device according to claim 1.

Some advantageous embodiments are the subject of the dependent claims.

DRAWINGS

Further features and advantages of the invention will become apparent from the description provided below of exemplary embodiment thereof, given by way of non-limiting example, with reference to the accompanying drawings, in which.

Figure 1:
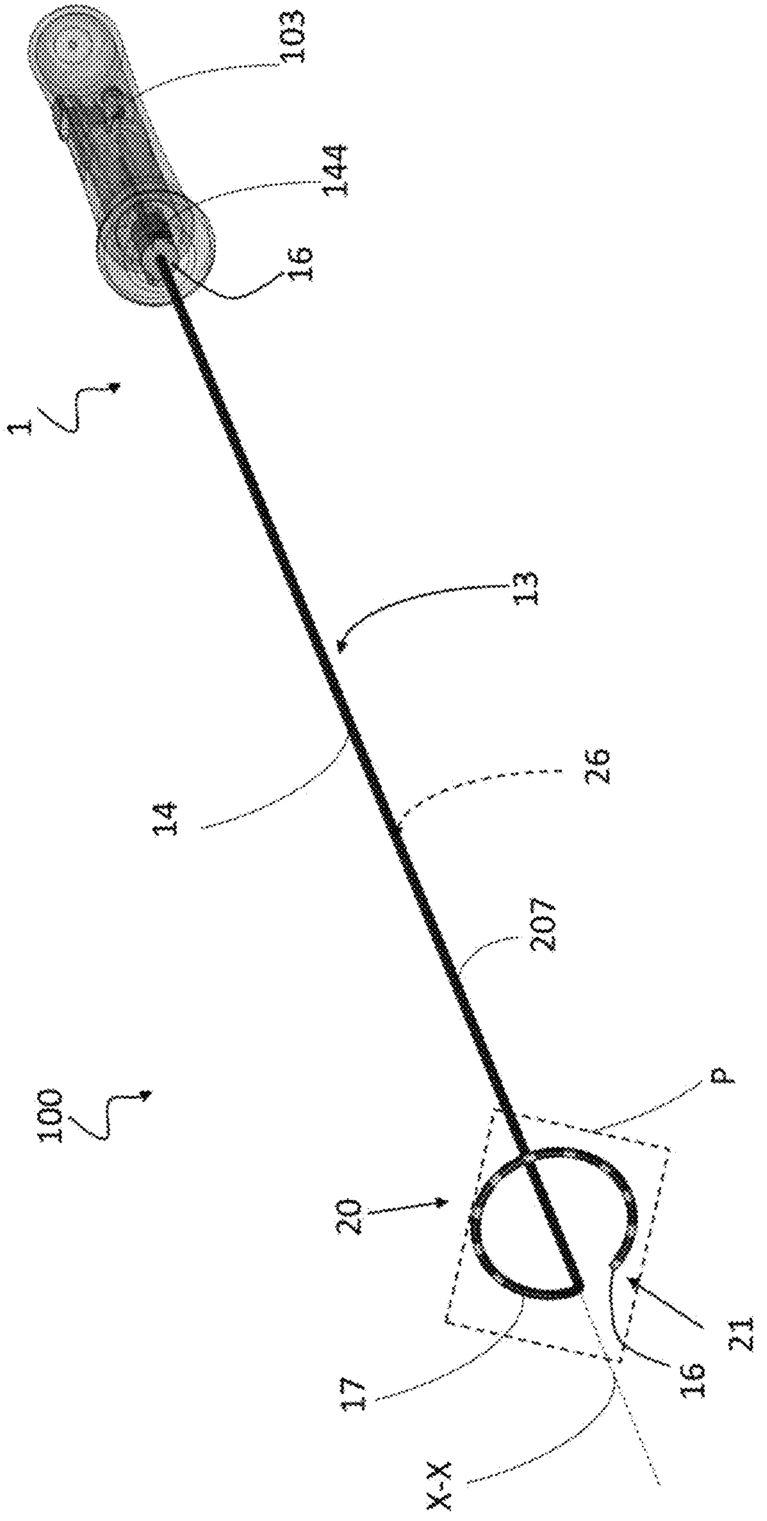
FIG. 1 is a perspective view of an ablation assembly according to an embodiment of the present invention showing an ablation catheter having an elongate shaft, and a shape setting mandrel having disposed within the ablation catheter.
Figure 3:
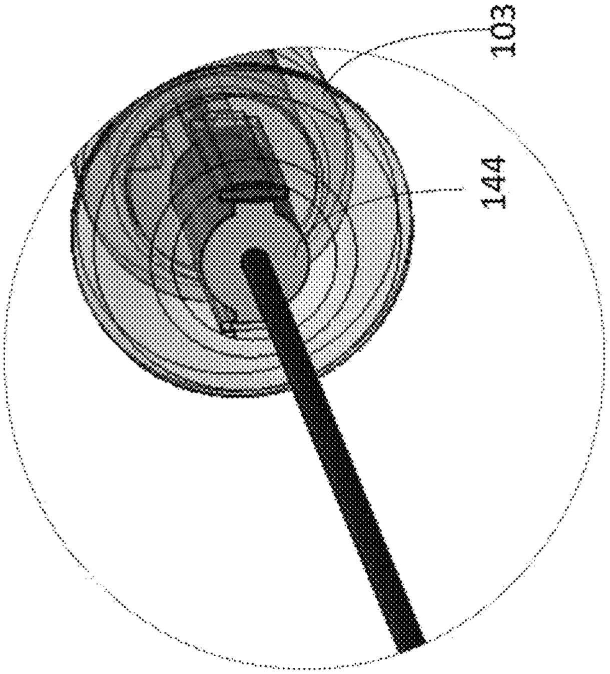
FIG. 3 is a detail of the ablation assembly of FIG. 1 showing an handle and a steering device connected to the handle and to the elongate shaft.
Figure 2:
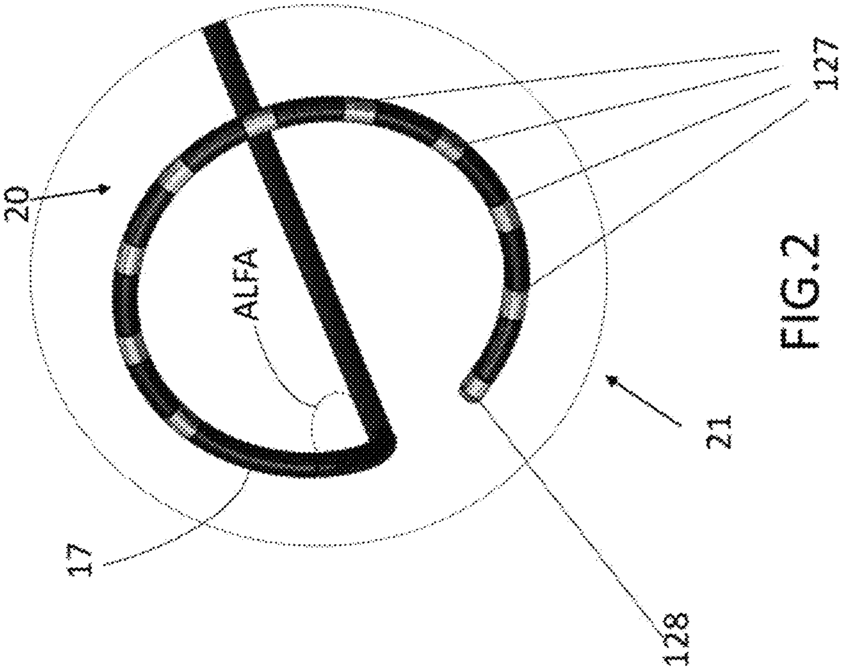
FIG. 2 is a detail of the ablation assembly of FIG. 1 showing a shaft distal portion of the elongate shaft.
Figure 4:
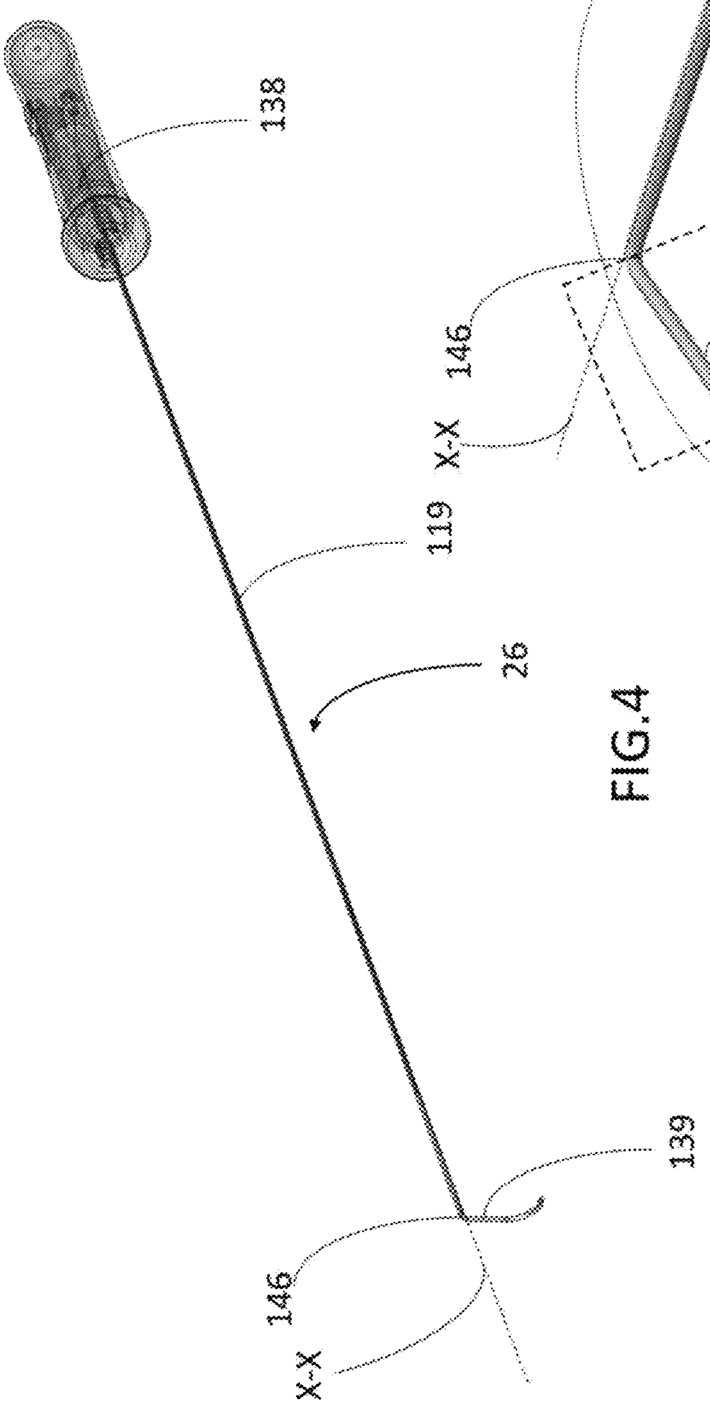
FIG. 4 shows an ablation assembly according to the invention, wherein the elongate shaft and the steering device are omitted to show the shape setting mandrel partially inserted into the handle, wherein the shape setting mandrel has a bend preformed configuration.
Figure 5:
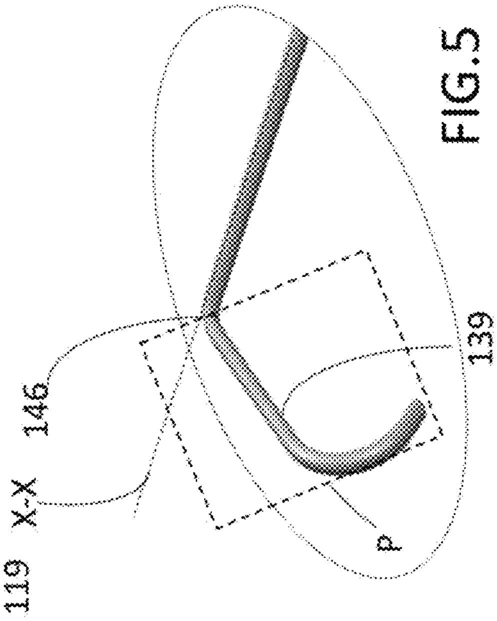
FIG. 5 is a detail of the shape setting mandrel of FIG. 4 showing a mandrel distal portion in the bend preformed configuration.
Figure 7:
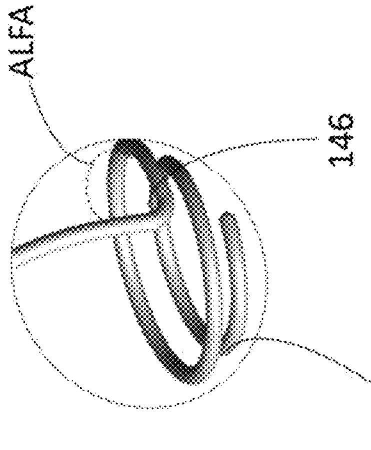
FIG. 7 is a detail of the shape setting mandrel of FIG. 6 showing a mandrel distal portion in the spiral bend preformed configuration.
Figure 6:
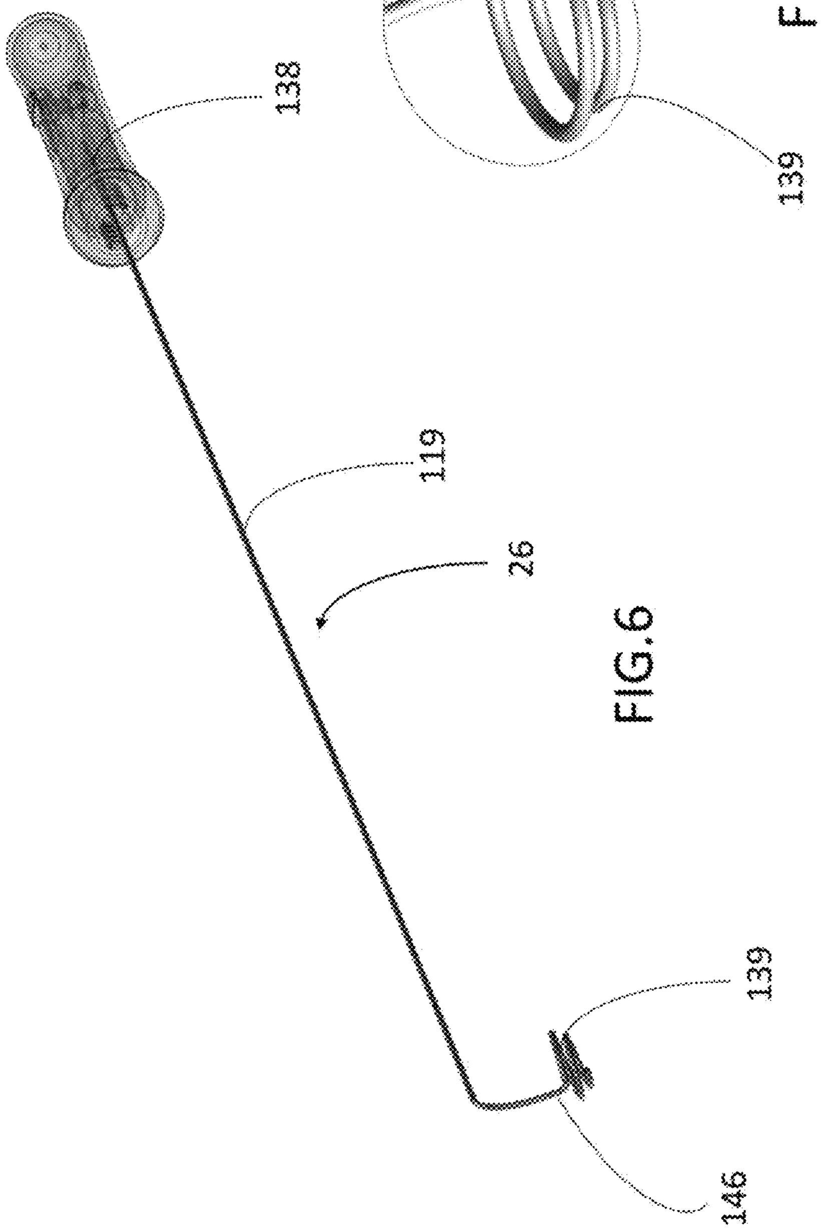
FIG. 6 shows an ablation assembly according to the invention, wherein the elongate shaft and the steering device are omitted to show the shape setting mandrel partially inserted into the handle, wherein the shape setting mandrel has a spiral bend preformed configuration.
Figure 8:
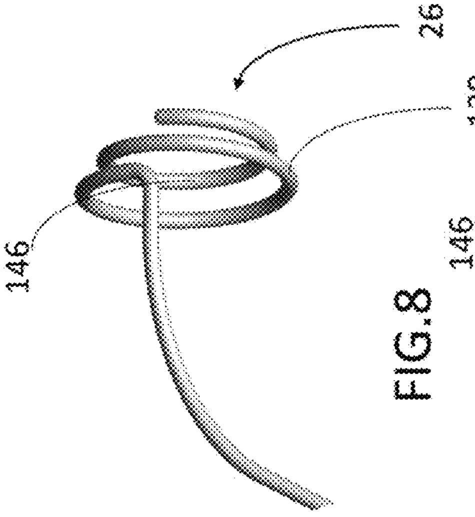
FIGS. 8-13 show different preformed configuration of a shape setting mandrel and the ablation assembly of the present invention.
Figure 9:
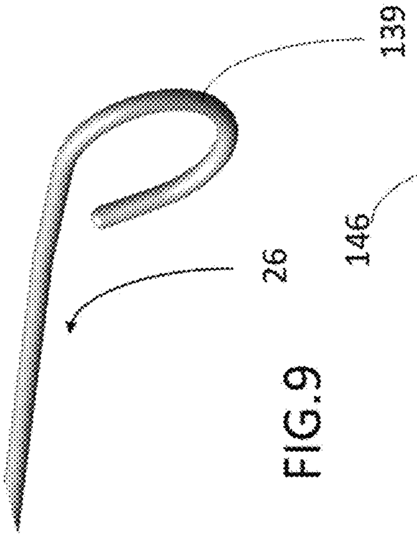
Figure 10:
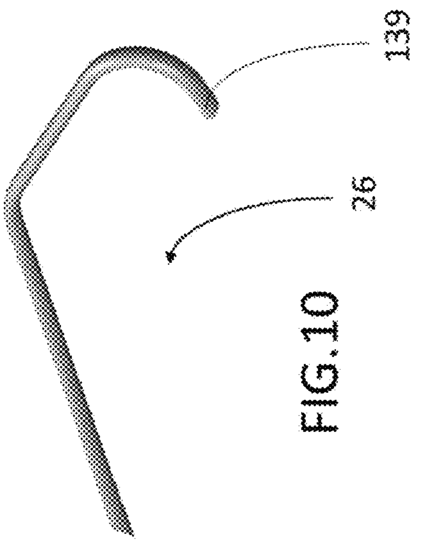
Figure 11:
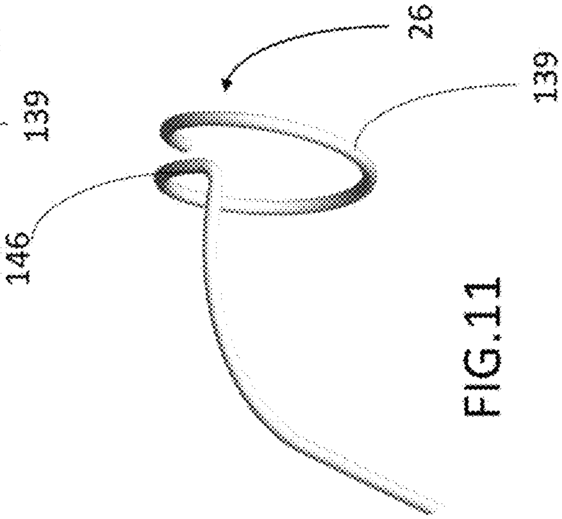
Figure 12:
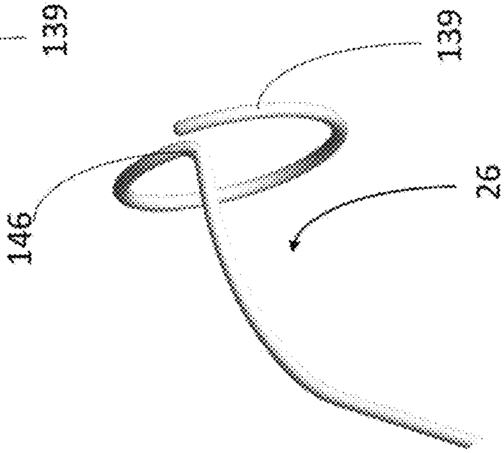
Figure 13:
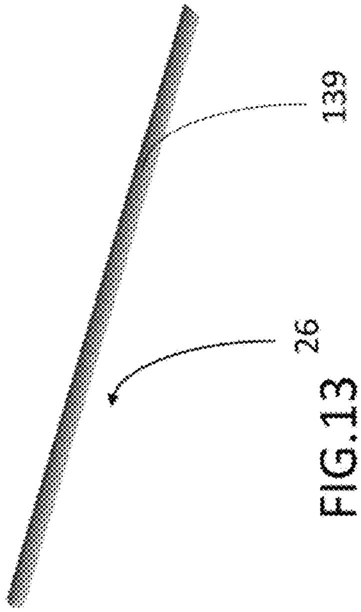
Figure 15:
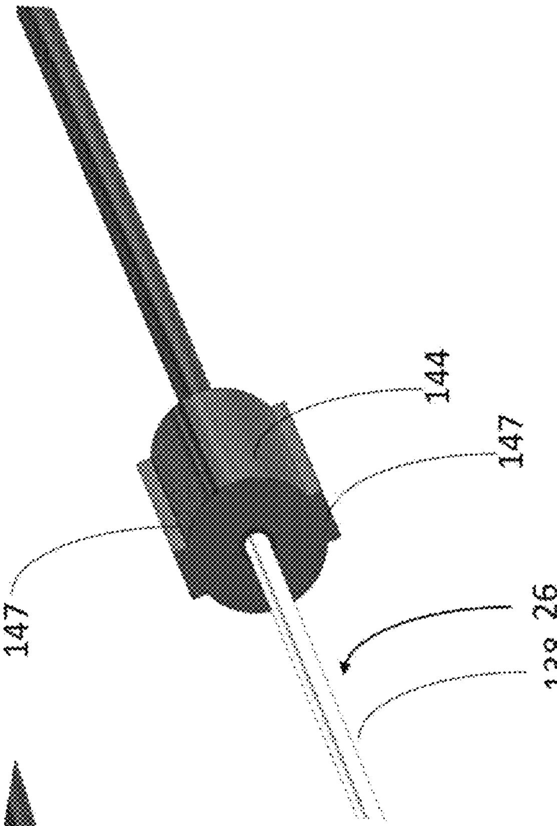
FIGS. 14-15 show a sequence of insertion of a shape setting mandrel in a loaded straight configuration within the elongate shaft of the ablation catheter of FIG. 1, wherein the shape setting mandrel slides into a steering device connectable to an handle of the ablation catheter.
Figure 14:
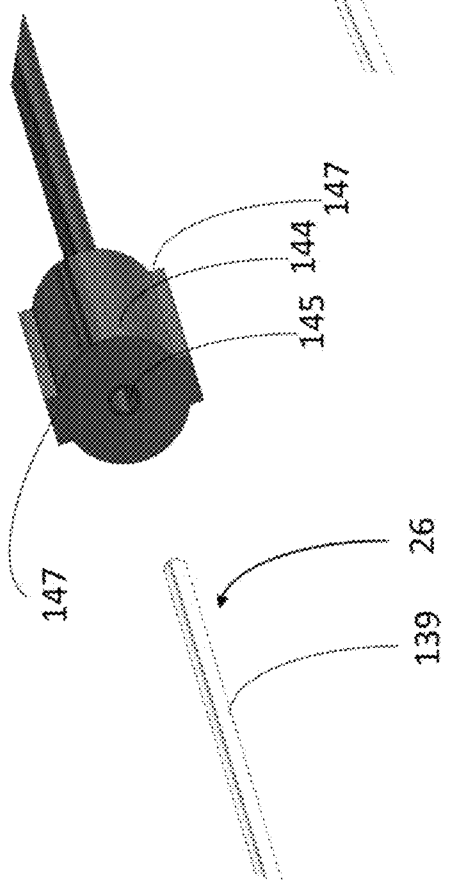
Figure 16:
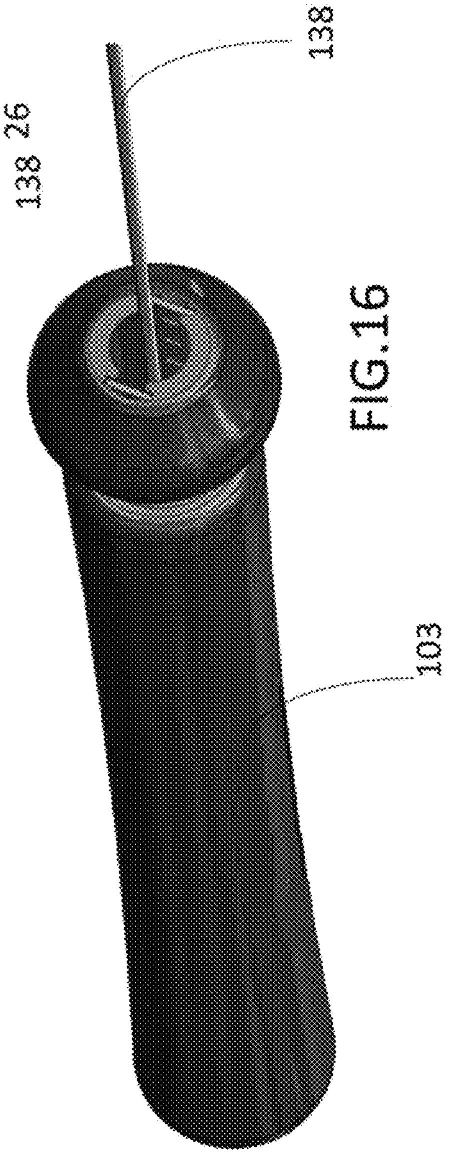
FIG. 16 is a partial perspective view of the ablation assembly according to the invention, wherein the steering device and elongate shaft of FIGS. 14 and 15 are omitted in order to show a proximal part of the mandrel disposed within the handle of the ablation catheter.
Figure 17:
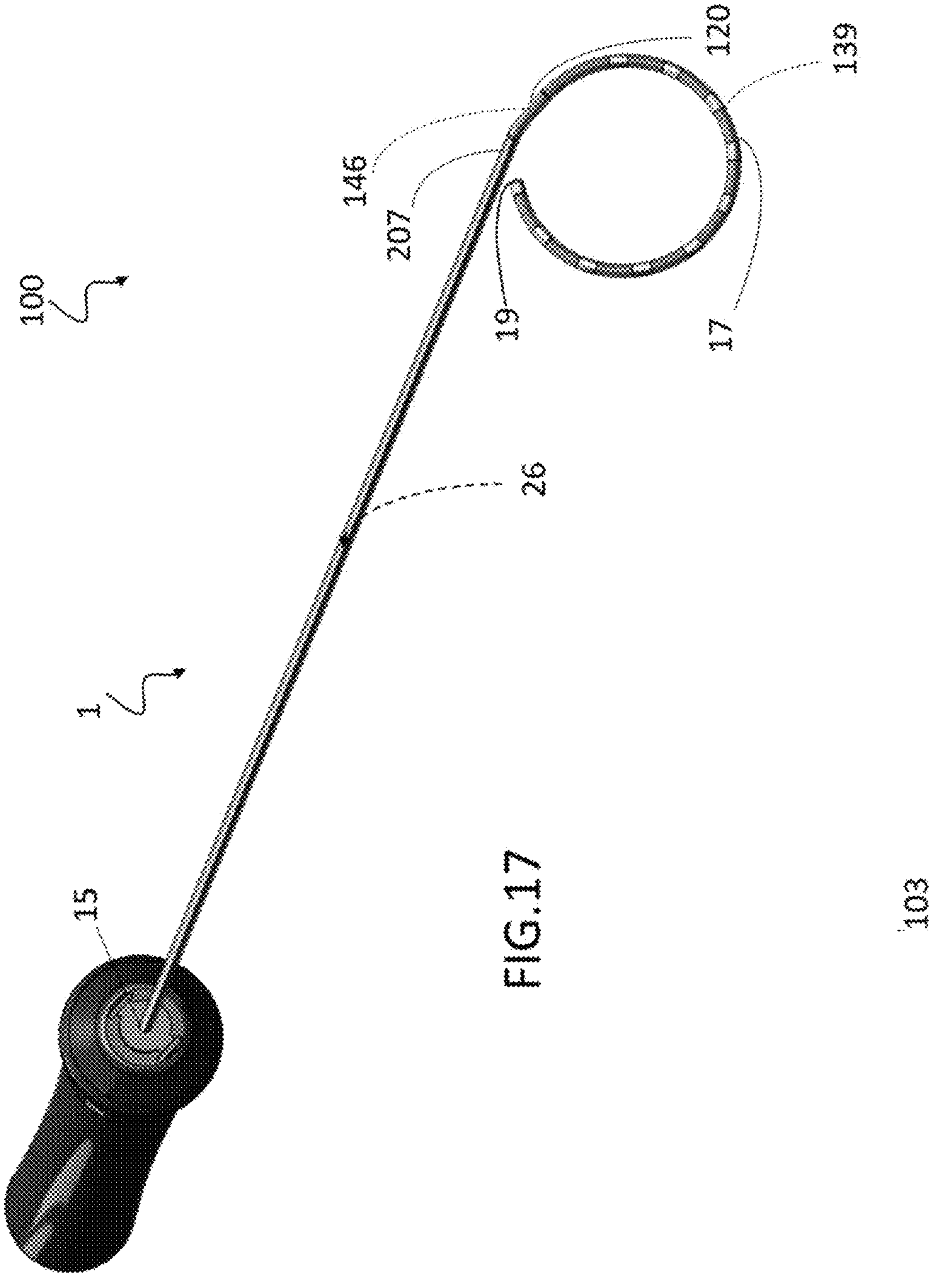
FIG. 17 is a perspective view of an ablation assembly according to another embodiment of the present invention showing an ablation catheter having an elongate shaft, and a shape setting mandrel having a circular preformed configuration disposed within the ablation catheter.
Figure 18:
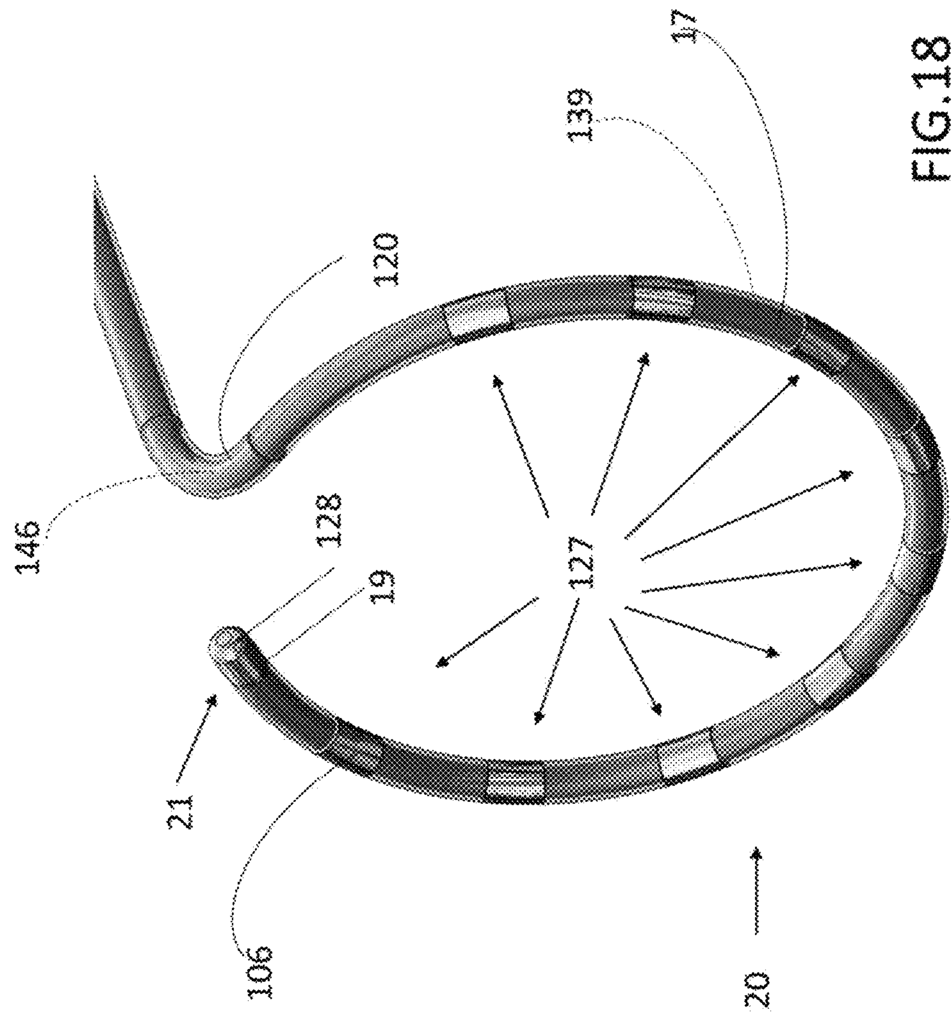
FIG. 18 is a detail of the ablation assembly of FIG. 1 showing a shaft distal portion of the elongate shaft.
Figure 20:
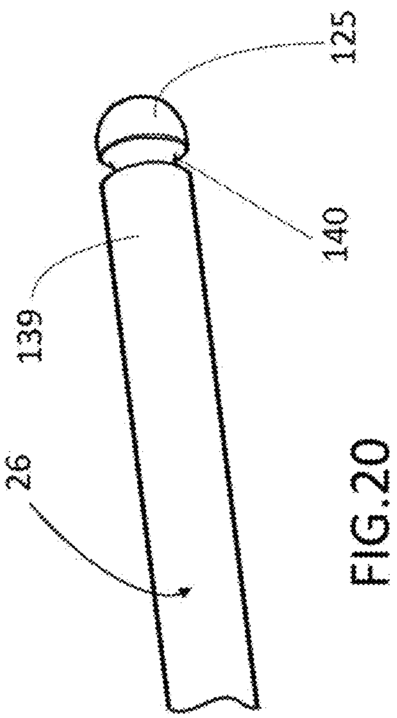
FIG. 20 shows in detail the shape setting mandrel of FIG. 19 having a ball tip.
Figure 19:
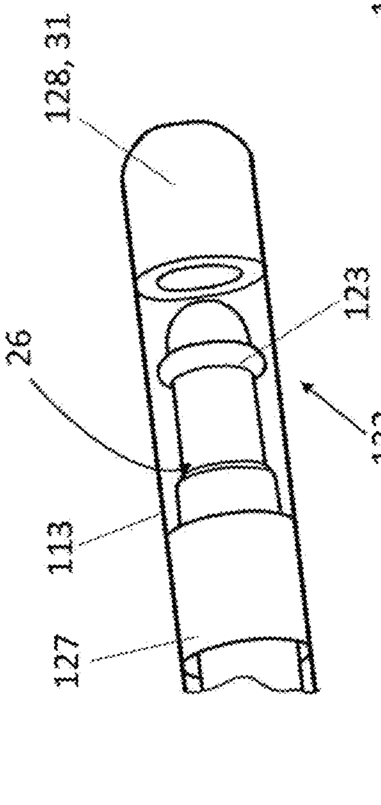
FIG. 19 is perspective and schematic view of a shaft distal portion of the ablation catheter of the assembly according to the invention, that shows a locking mechanism between a shape setting mandrel and the shaft distal portion.
Figure 21:
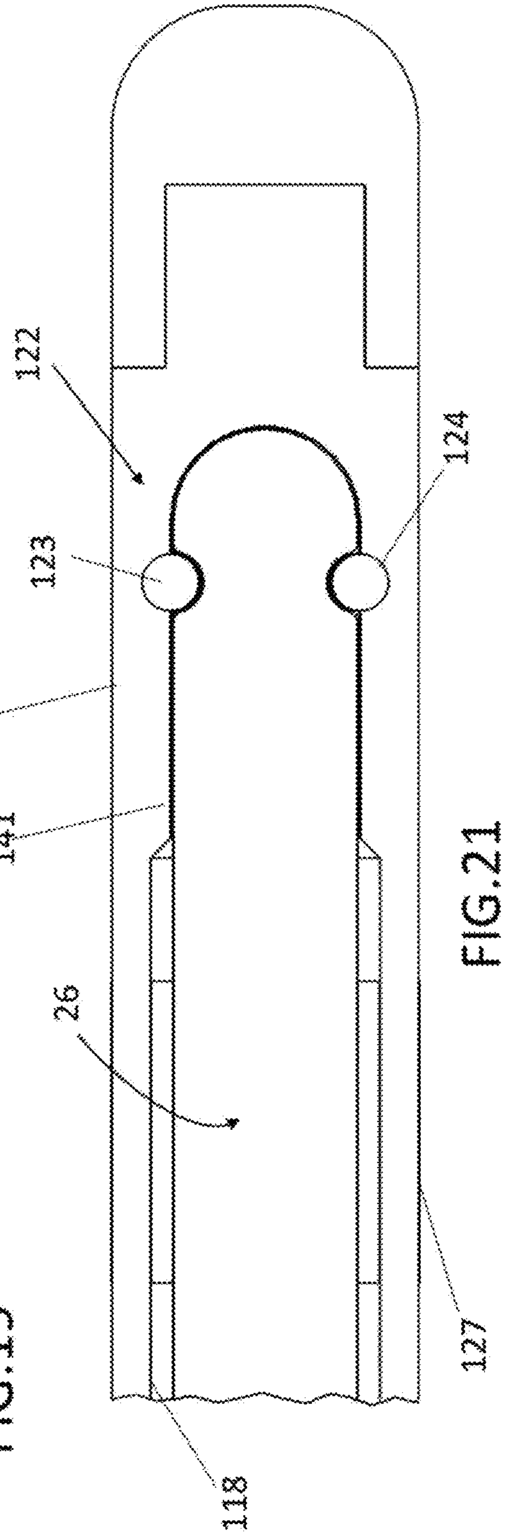
FIG. 21 is a section view of the shaft distal portion of FIG. 19 along a longitudinal direction showing in detail the elements of the locking mechanism.
Figure 23:
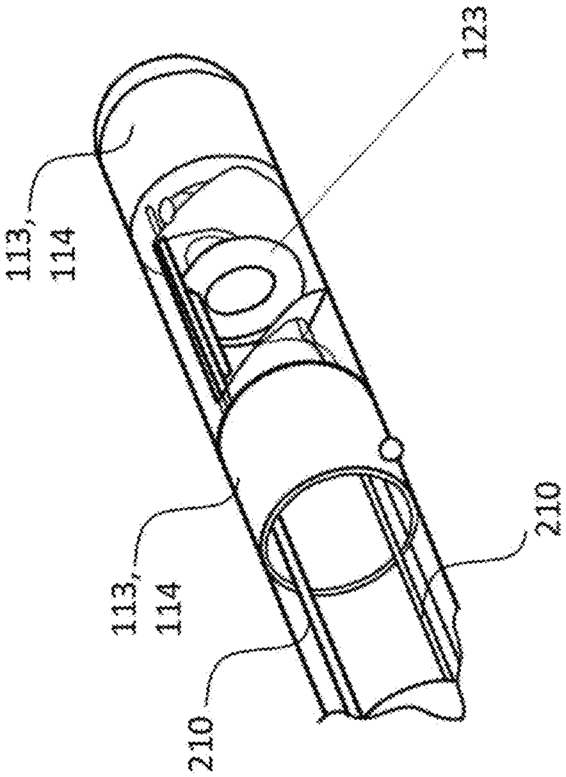
FIG. 23 is a perspective view of the shaft distal portion of FIG. 19, wherein some external elements are partially removed and the shape setting mandrel is omitted to show the inner lumen of the catheter.
Figure 22:
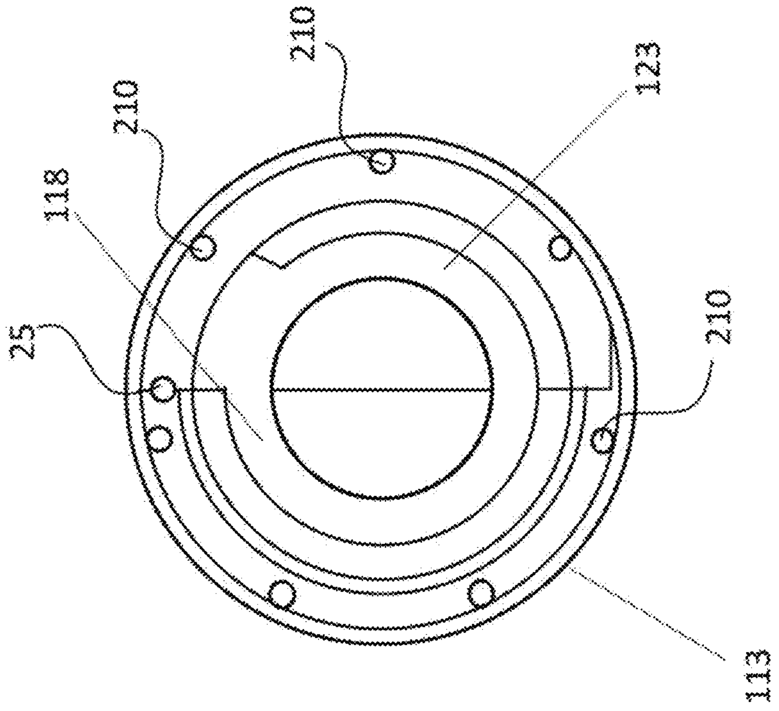
FIG. 22 is a cross-sectional view of the shaft distal portion of FIG. 19, wherein the shape setting mandrel is omitted.
Figure 24:
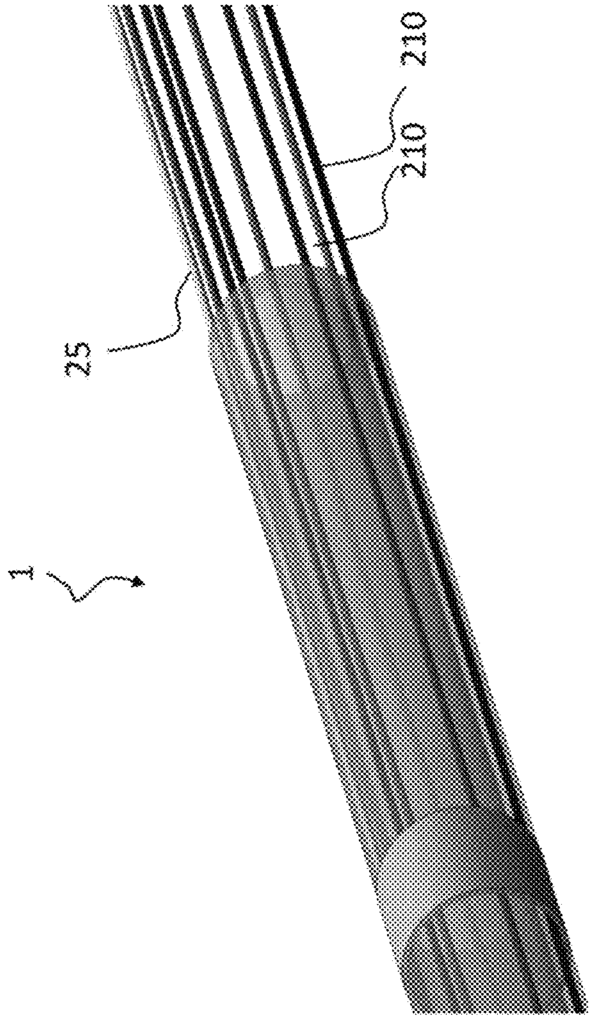
FIG. 24 is a perspective schematic view of a portion of the ablation catheter wherein are shown electrical connectors disposed within the ablation catheter.
Figure 26:
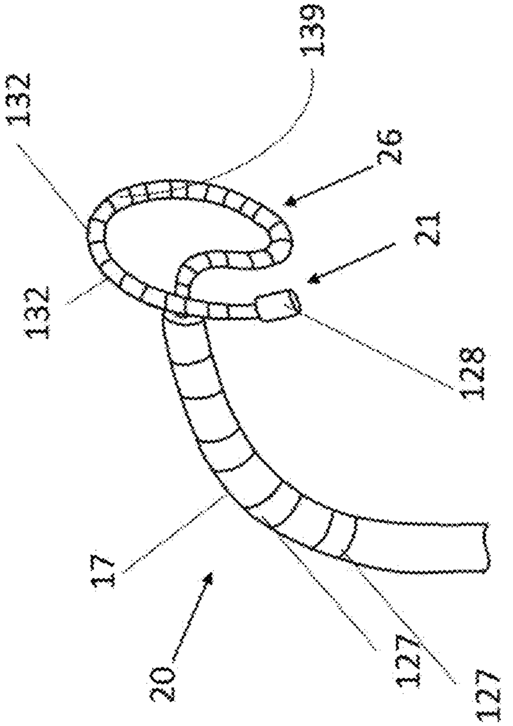
Figure 25:
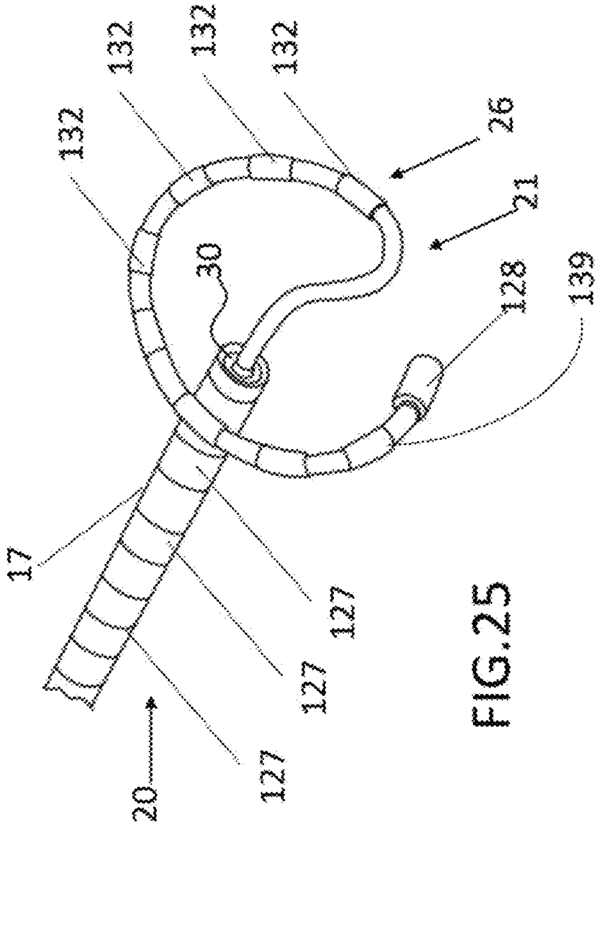
FIG. 25 is a perspective view of a distal portion of an ablation assembly according to a further embodiment of the present invention showing an ablation catheter having an elongate shaft, and a shape setting mandrel having a circular preformed configuration disposed with its distal portion beyond a distal end of the elongate shaft.
Figure 27:
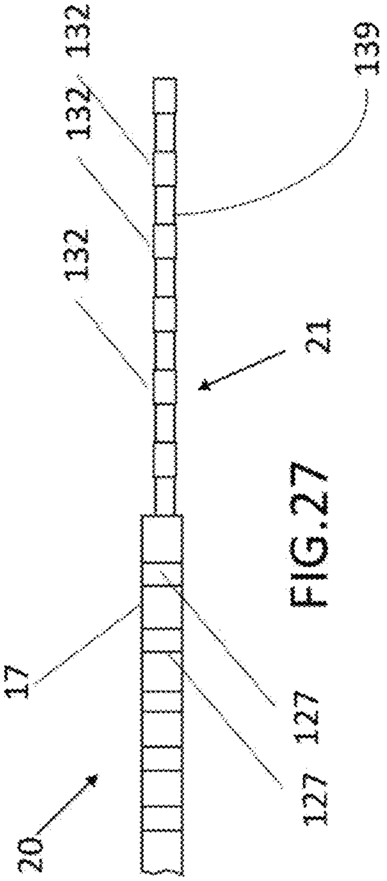
Figure 28:
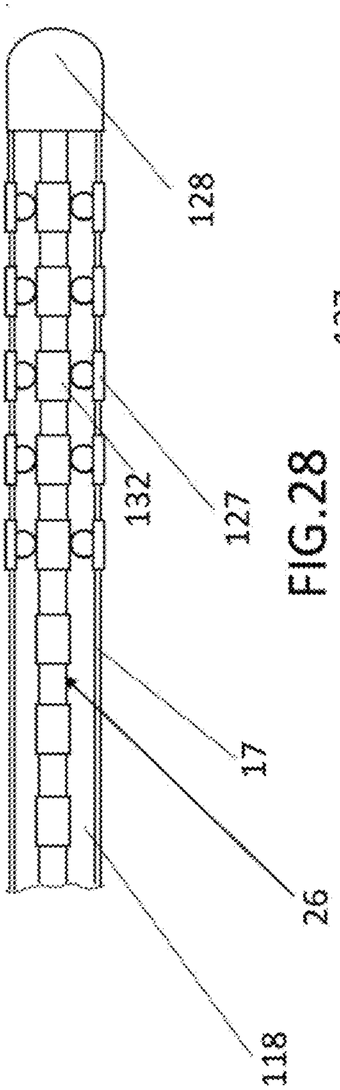
Figure 29:
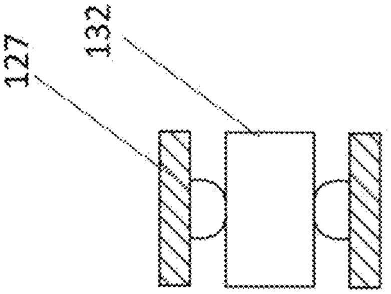
Figure 30C:
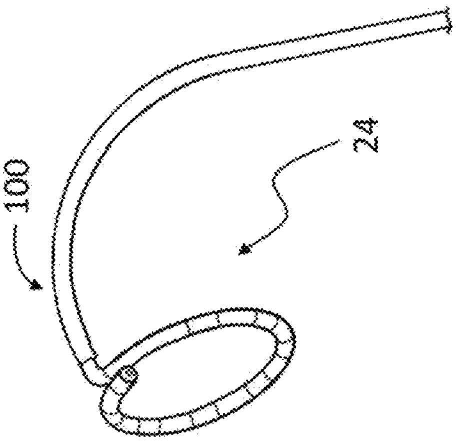
Figure 30A:
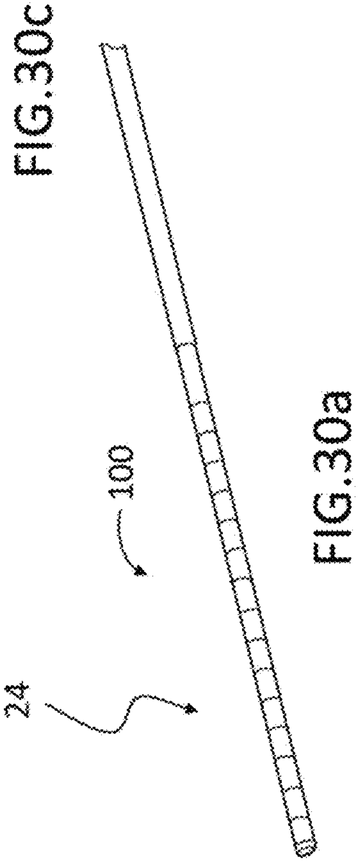
Figure 30B:
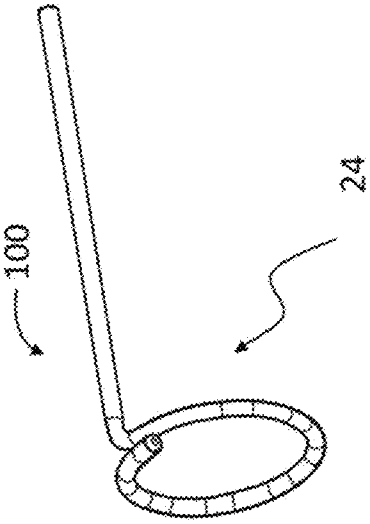
Figure 32B:
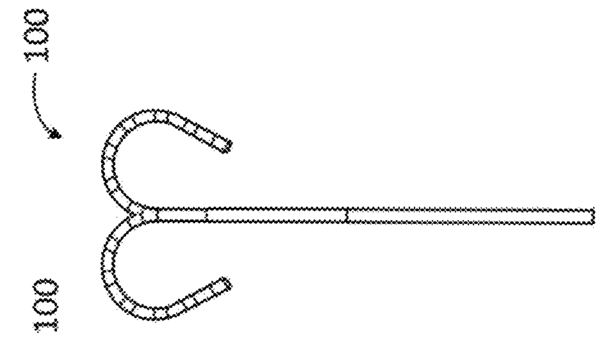
Figure 32A:
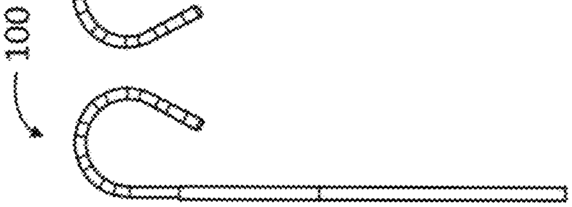
Figure 31B:
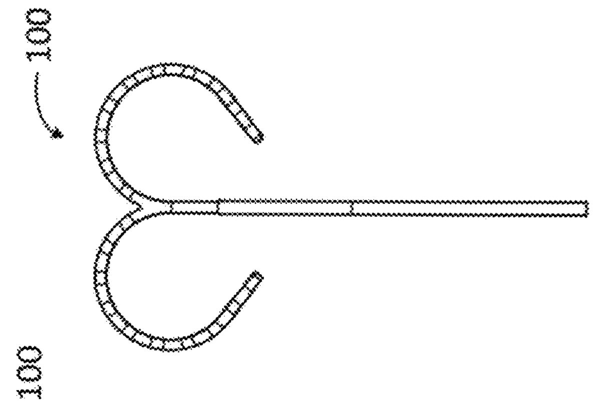
Figure 31A:
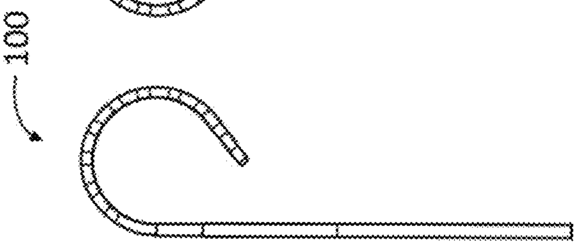
Figure 34B:
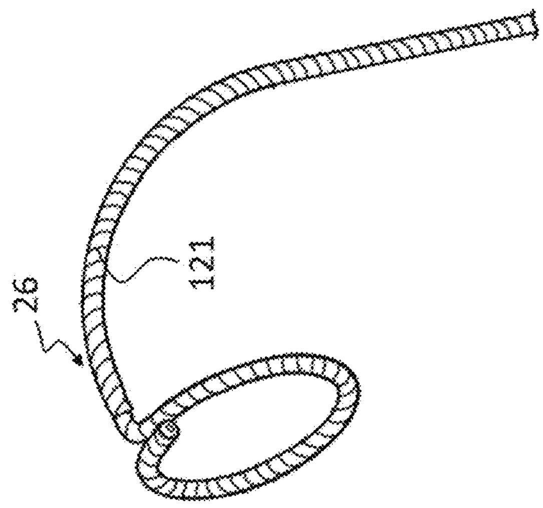
Figure 34A:
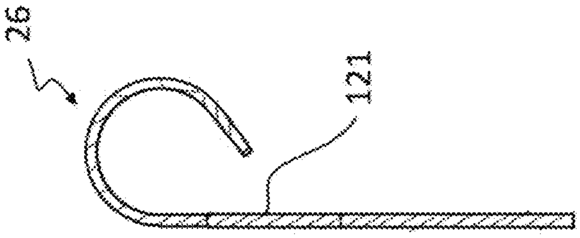
Figure 33B:
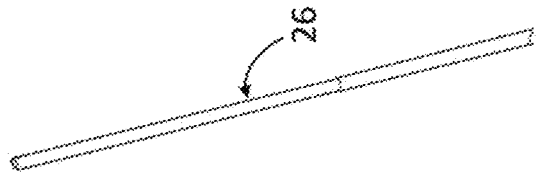
Figure 33A:
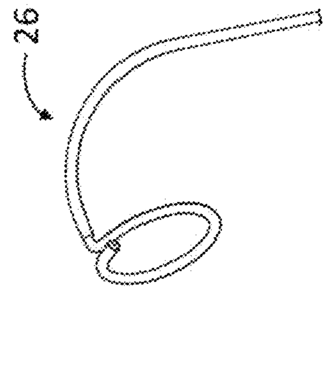
Figure 33C:
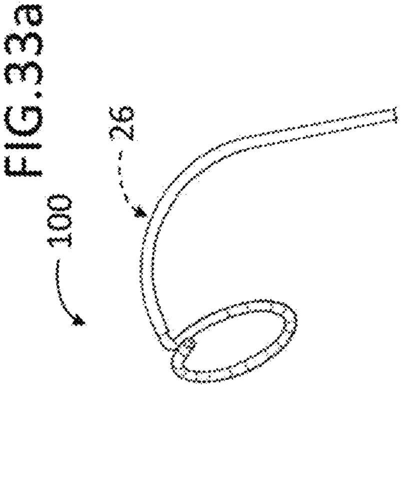
Figure 35D:
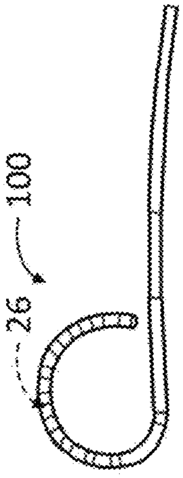
Figure 35C:
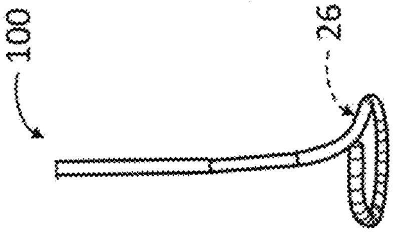
Figure 35A:
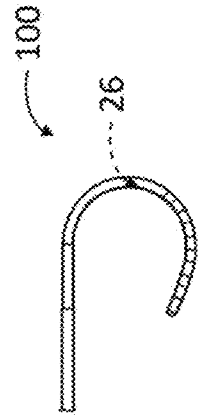
Figure 35B:
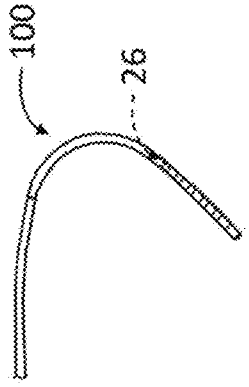
Figure 37:
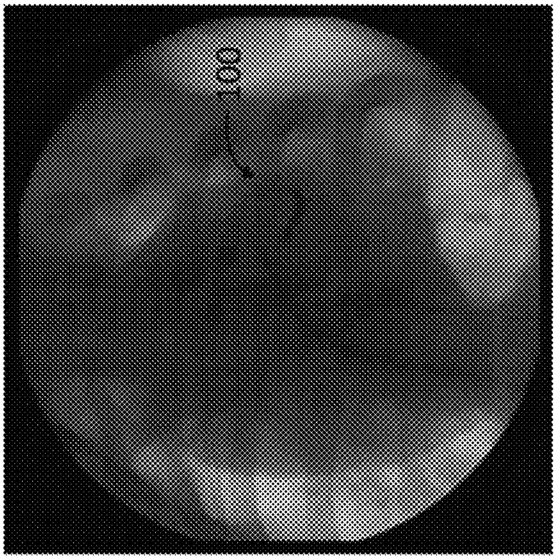
Figure 36:
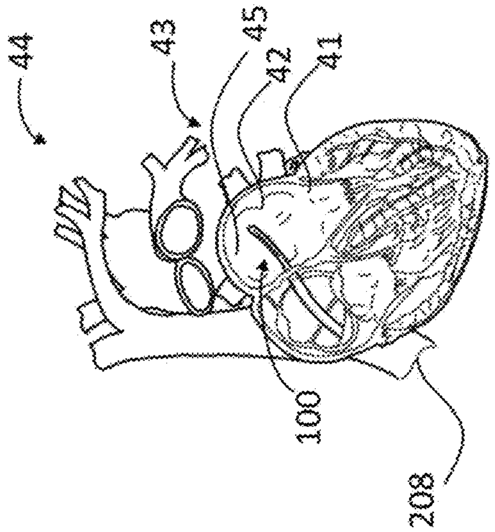
Figure 42A:
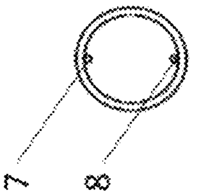
Figure 42B:
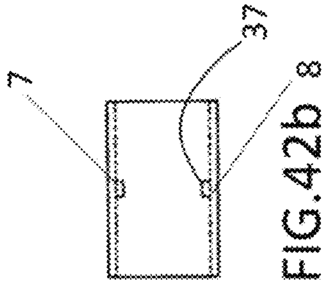
Figure 43A:
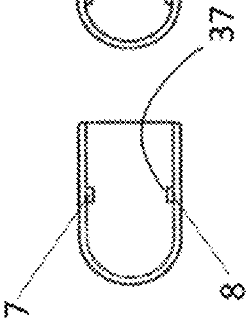
Figure 43B:
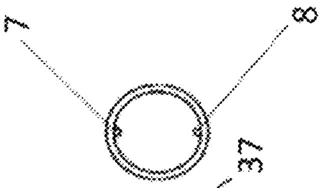
Figure 41:
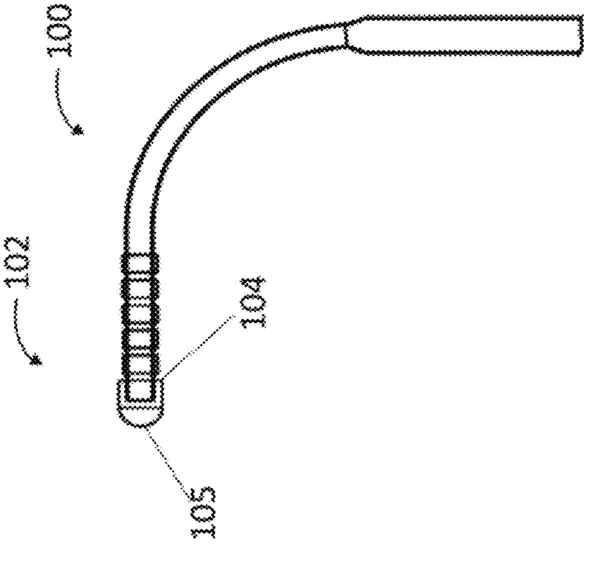
Figure 44:
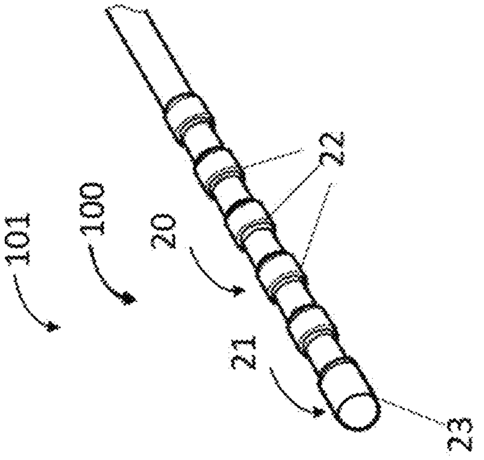
Figure 45:
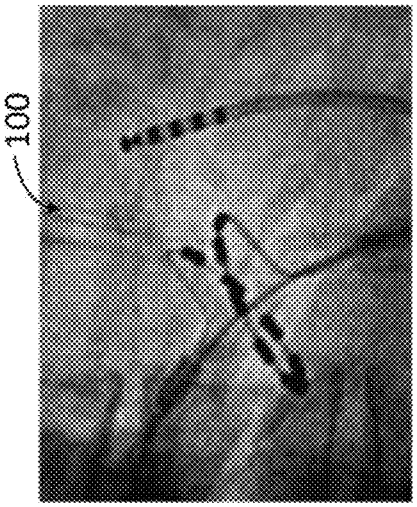
Figure 46:
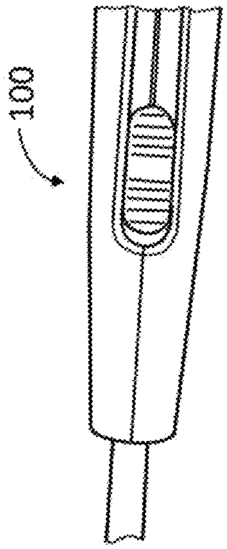
Figures 47A, 47B, 47C:
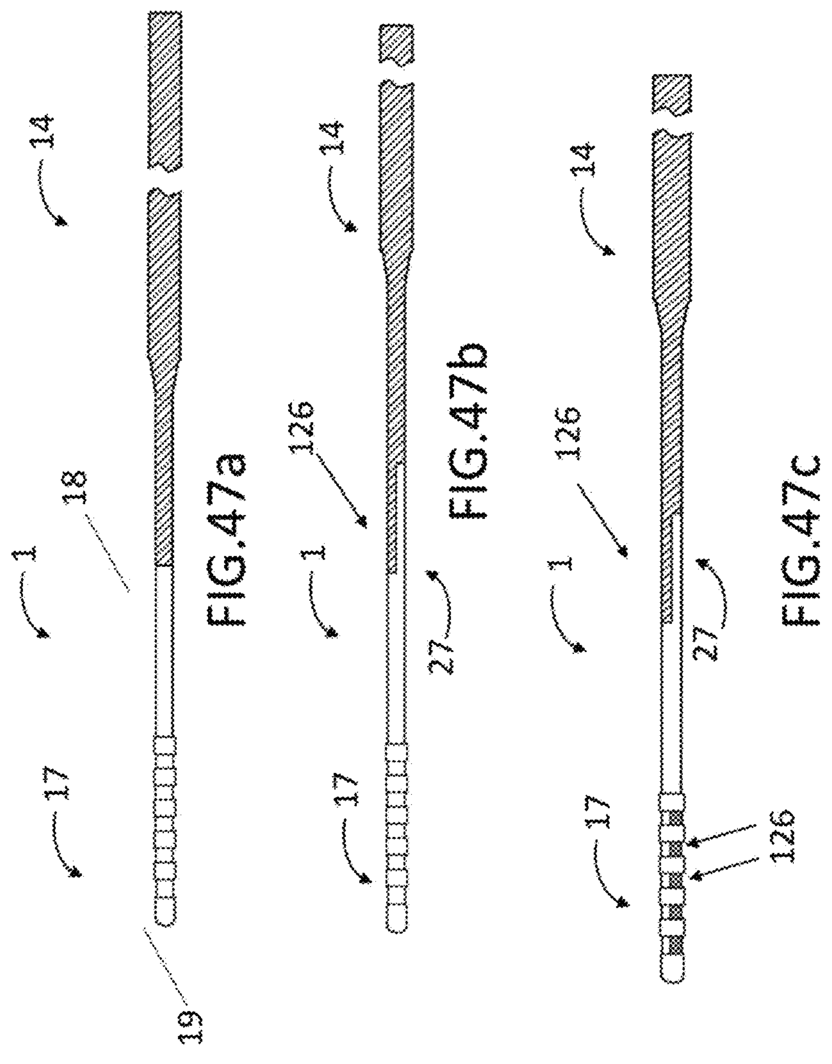
Figure 49:
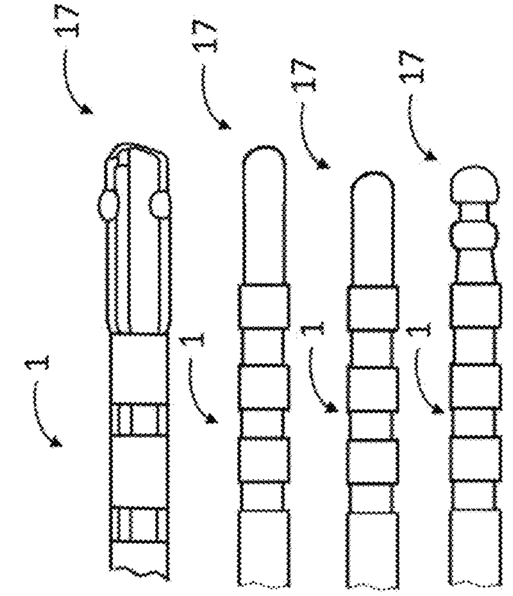
Figure 48:
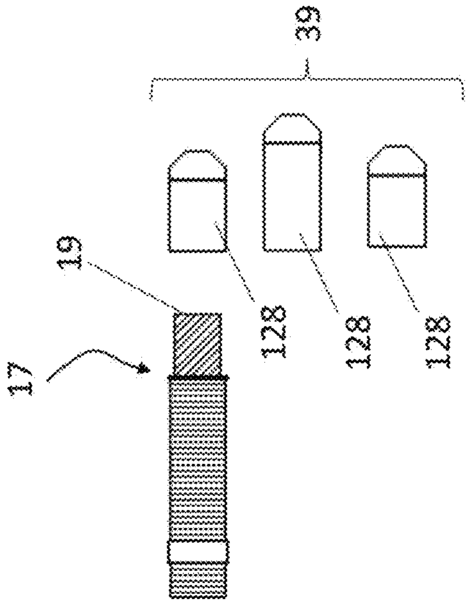
Figure 50:
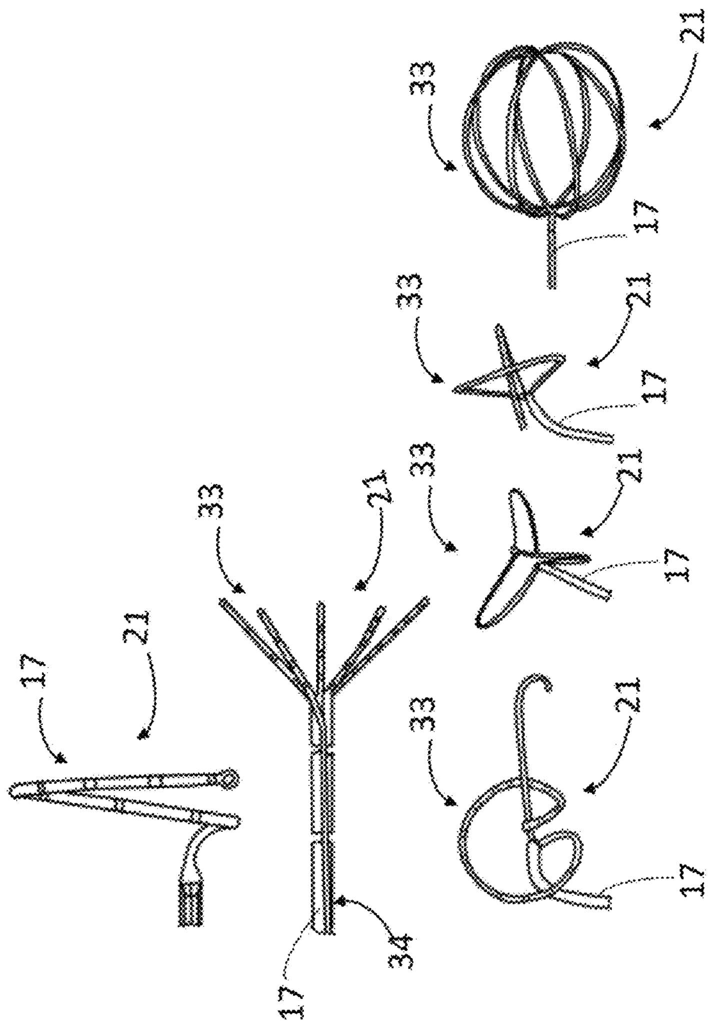
Figure 51:
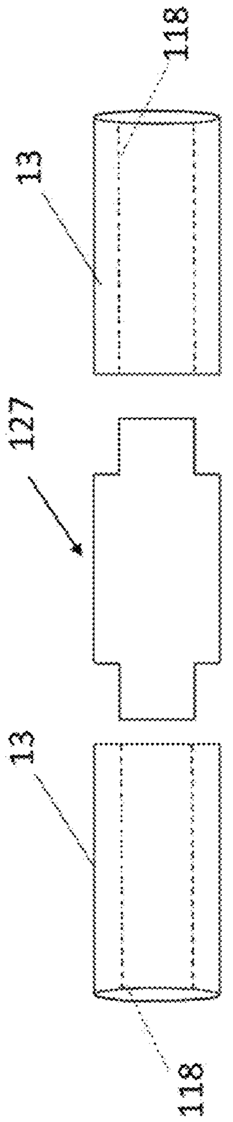
Figure 52:
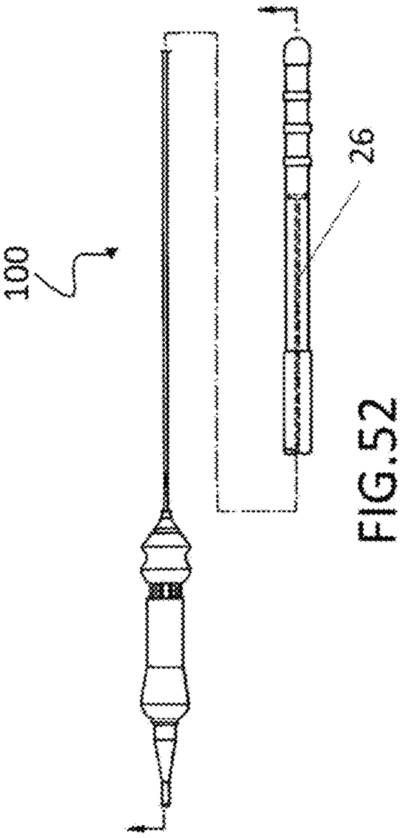
Figure 54:
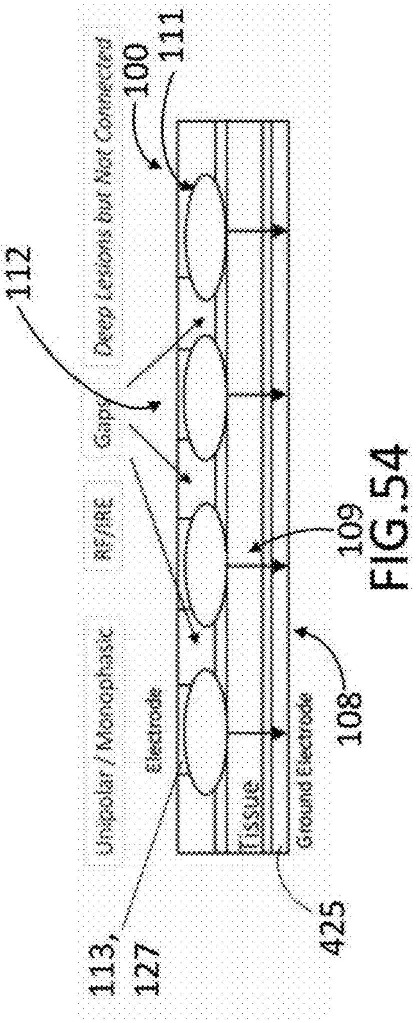
Figure 55:
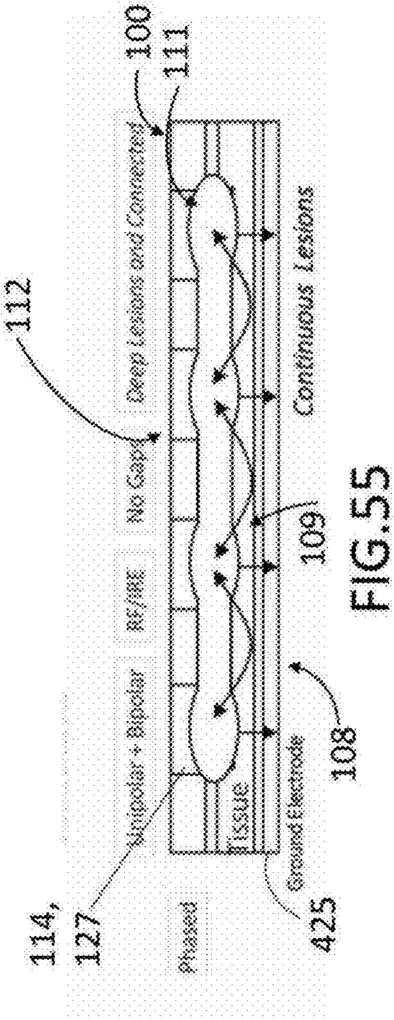
Figure 53:
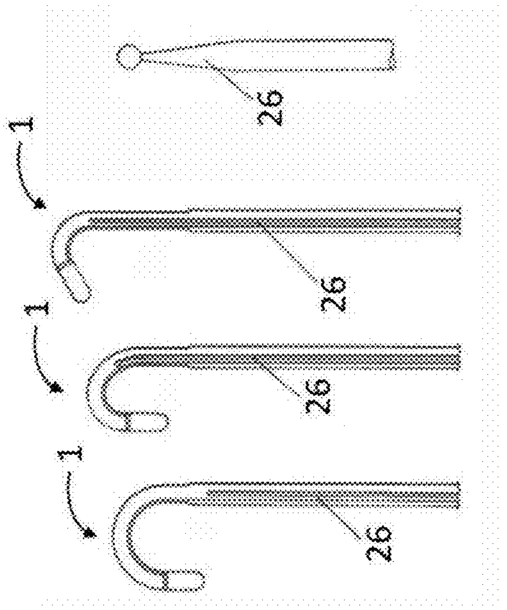
Figure 56:
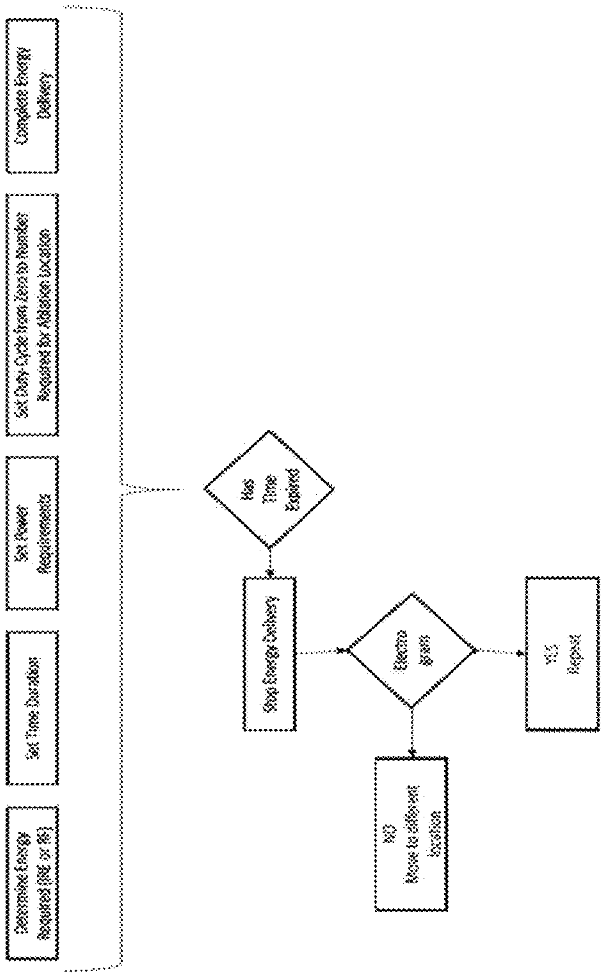
Figure 57:
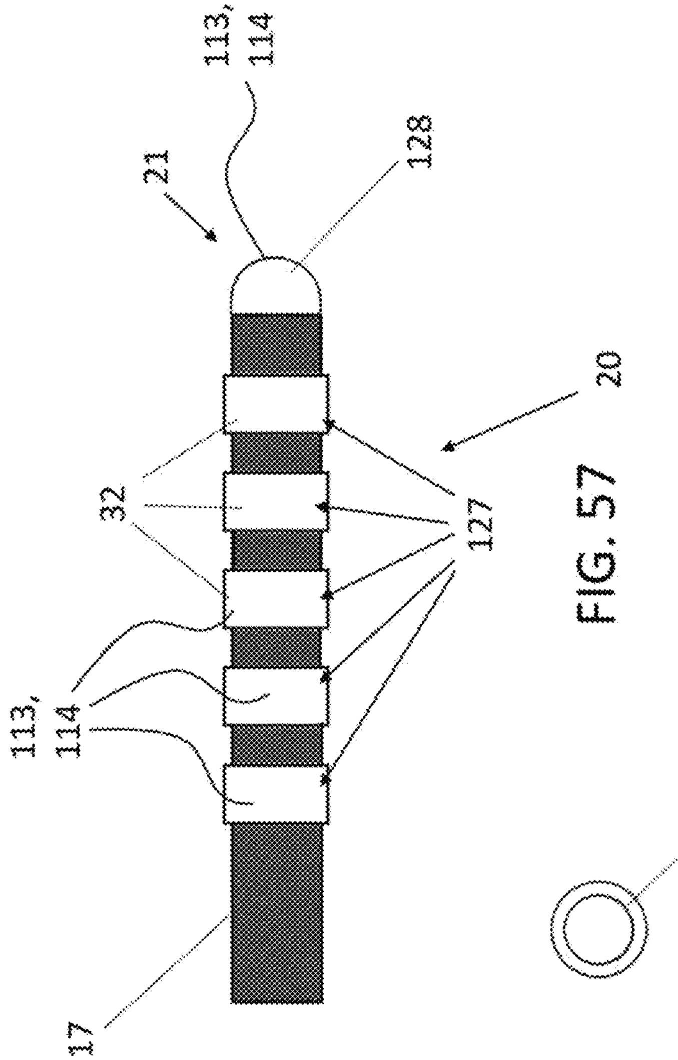
Figure 58:
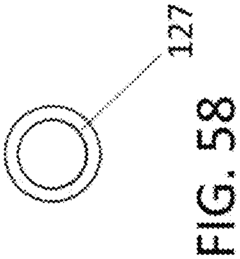
Figure 59:
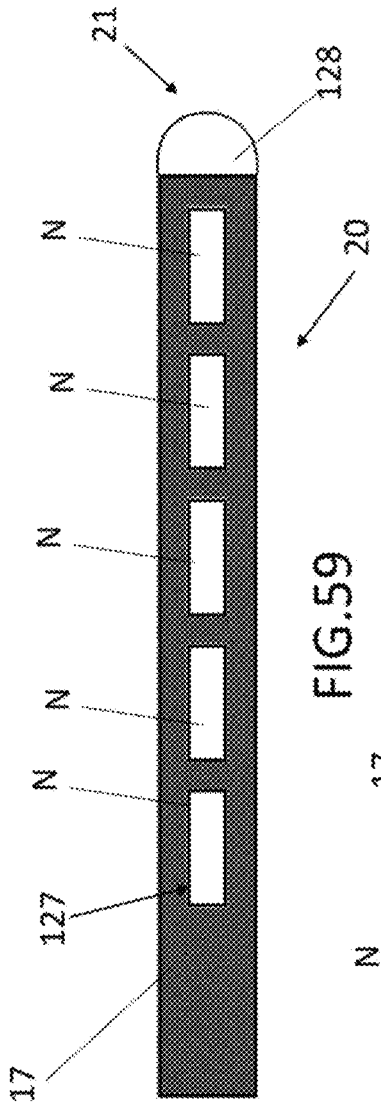
Figure 60:
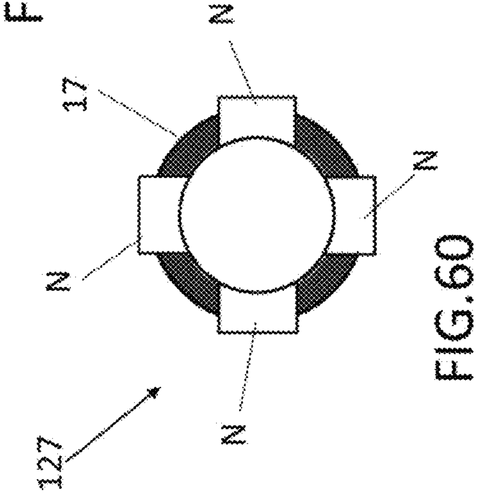
Figure 61:
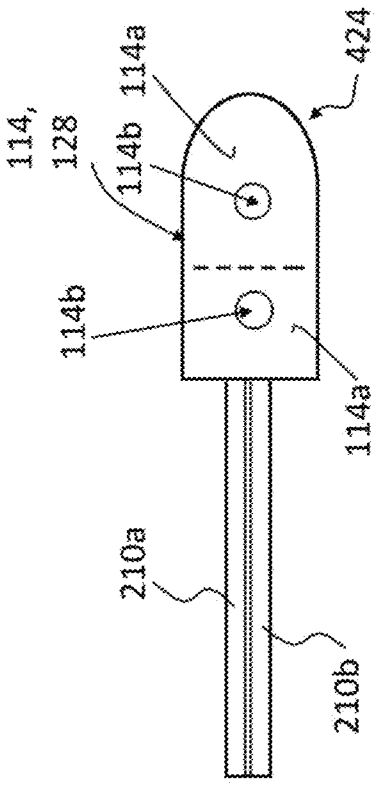
Figures 62A, 62B, 62C:
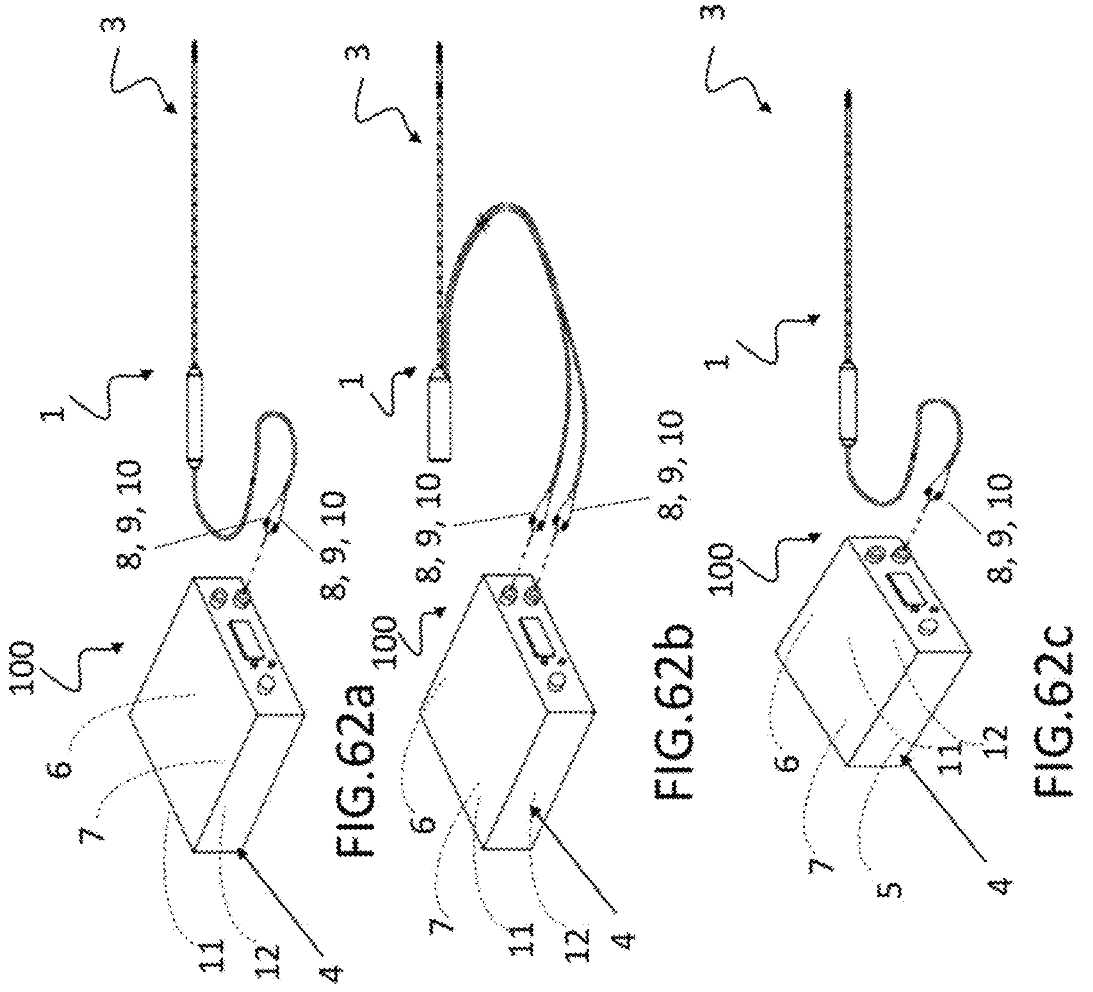
Figure 63:
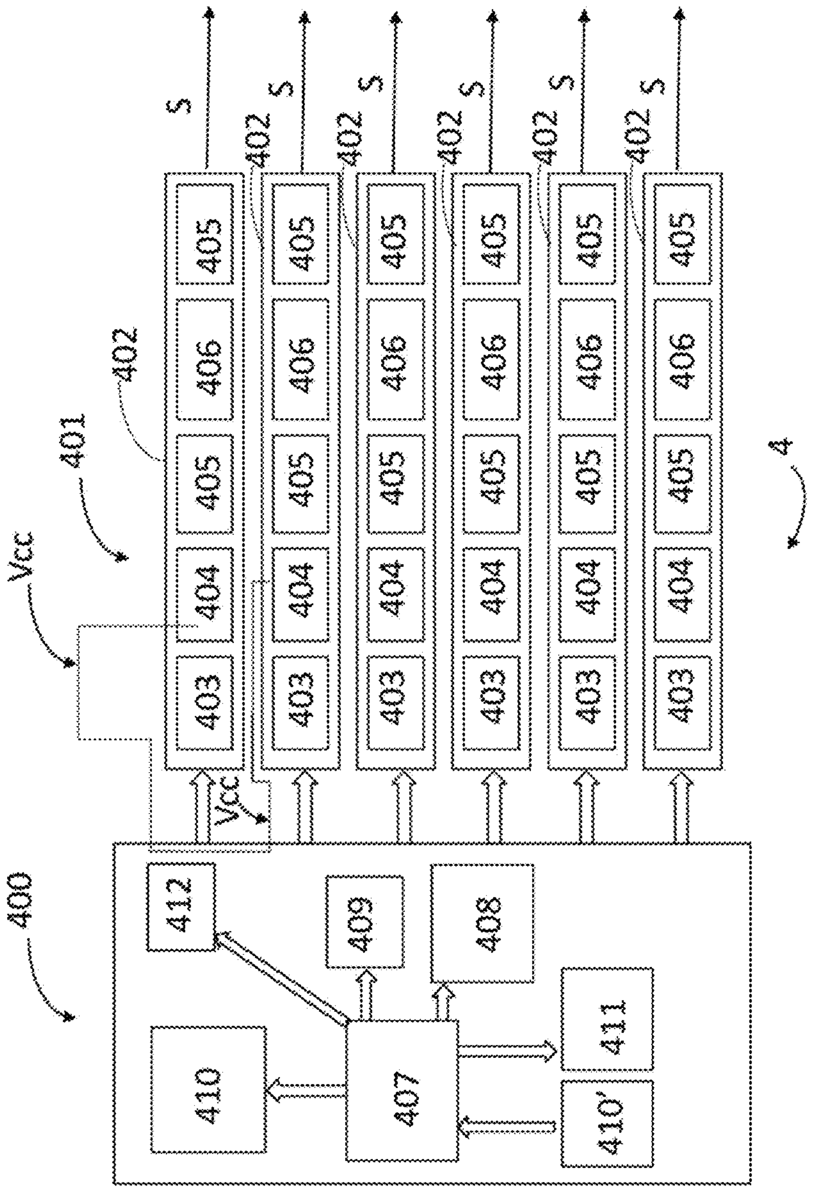
Figures 64A, 64B, 64C:
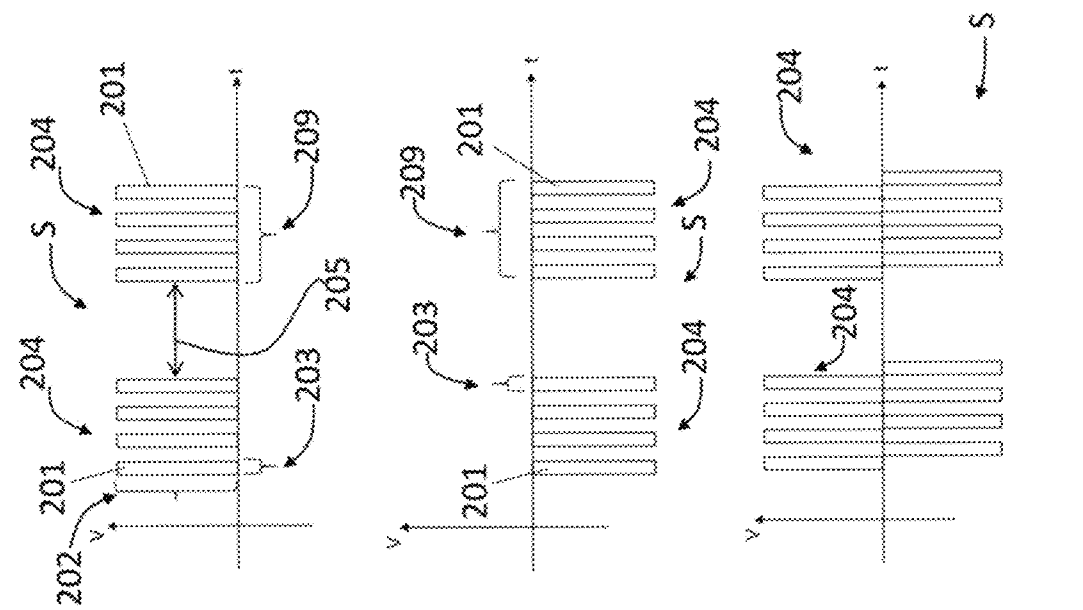
Figure 65:
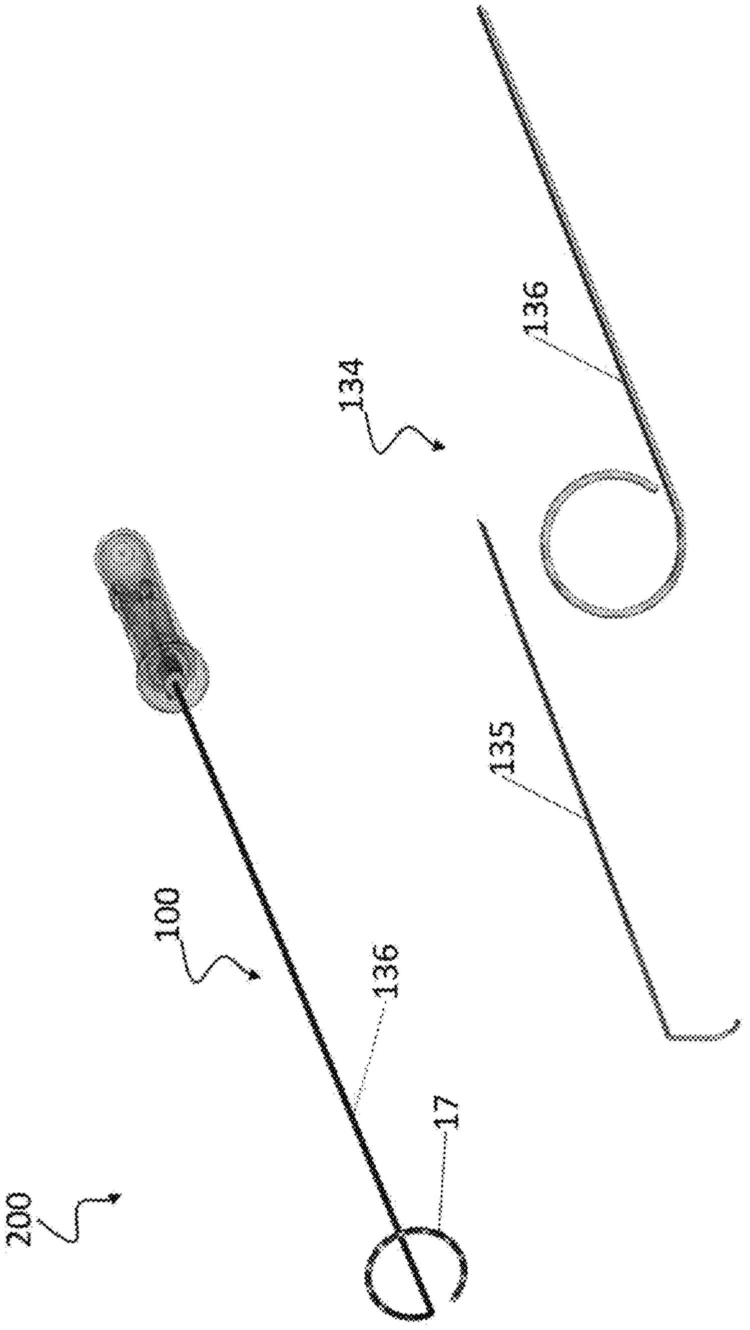
Figure 66:
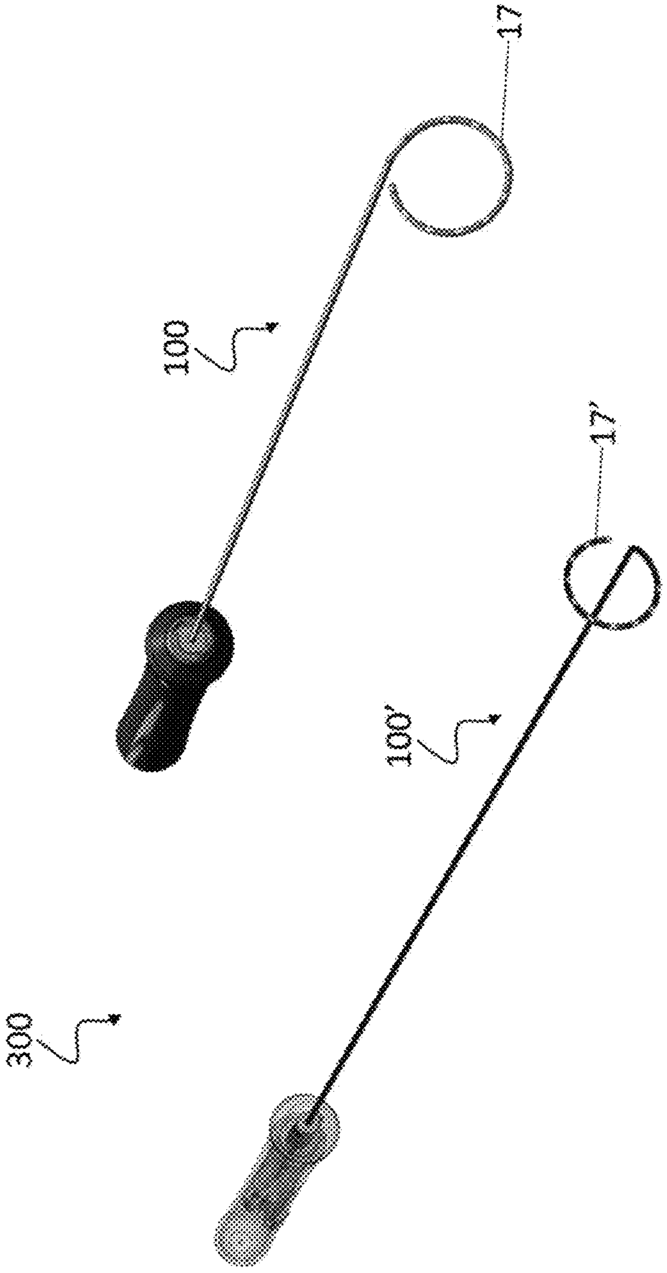
Figure 67:
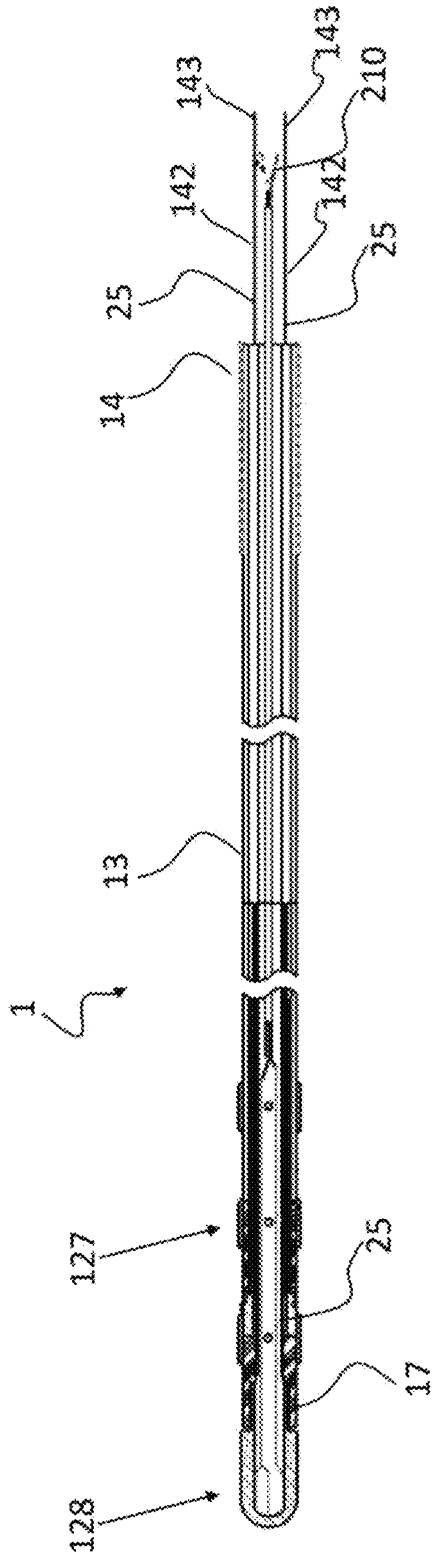

FIG. 26 is a perspective view of a distal portion of an ablation assembly according to a further embodiment of the present invention showing an ablation catheter having an elongate shaft, and a shape setting mandrel having a circular preformed configuration disposed with its distal portion beyond a distal end of the elongate shaft, and wherein a distal portion of the elongate shaft is deflected in a deflection direction, wherein the shape setting mandrel comprises a plurality of mandrel electrodes disposed along its length, and the elongate shaft comprises a plurality of shaft electrodes;

FIG. 27 is a side view of the ablation assembly of FIG. 25;

FIG. 28 is a section view of the ablation assembly of FIG. 25, wherein the distal portion of the shape setting mandrel is fully inserted into the elongate shaft;

FIG. 29 shows a detail of FIG. 28, showing an electrical connection between the mandrel electrodes and the shaft electrodes;

FIG. 30*a*-30*c* shows a shape setting mandrel respectively in a loaded straight configuration, in a preformed circular configuration, and in a preformed circular and bent configuration;

FIGS. 31*a*-31*b* and 32*a*-32*b* show a plurality of shape setting mandrels having different preformed configurations;

FIG. 33*a*-33*c* shows a shape setting mandrel respectively in a preformed circular and bent configuration and in a loaded straight configuration, and the shape setting mandrel in the preformed circular and bent configuration disposed within an ablation catheter;

FIG. 34*a*-34*b* shows two shape setting mandrels coupled to a respective heating element, wherein the heating element is configured to apply heat to the shape setting mandrel to modify shape of the shape setting mandrel from a loaded configuration to a preformed configuration;

FIG. 35*a*-35*d* show different curves and 2-D and 3-D configurations of a distal portion of an ablation catheter with a shape setting mandrel disposed within the distal portion of the ablation catheter;

FIG. 36 shows an ablation assembly according to the present invention disposed within an heart, wherein a shape setting mandrel is fully inserted in a distal portion of the ablation catheter shaft;

FIG. 37 shows a radiography of an ablation assembly according to the present invention, wherein a catheter distal portion is shape set as a pre-formed configuration of a shape setting catheter fully inserted into the catheter distal portion;

FIG. 38 shows a plurality of shaft electrodes fixedly disposed and spaced apart along a catheter shaft distal portion according to an embodiment, wherein said shaft electrodes are biased in circular configuration on the catheter shaft;

FIG. 39 shows a shaft electrode disposed along the catheter shaft wherein the shaft electrode catheter is tubular and forms a part of the catheter shaft;

FIG. 40 shows the shaft electrodes of FIG. 38 an FIG. 39 in a bipolar configuration;

FIG. 41 is a side view of a distal portion of an ablation catheter according to the invention comprising a plurality of shaft electrodes and an tip electrode;

FIG. 42*a*-42*b* shows a cross-section view and a longitudinal section view of the ablation catheter of FIG. 41, showing the electrical connections for electrical wires for connecting one of the shaft electrodes to a single power source;

FIG. 43*a*-43*b* shows a cross-section view and a longitudinal section view of the ablation catheter of FIG. 41, showing the electrical connections for electrical wires for connecting the tip electrode to a single power source;

FIG. 44 is a perspective view of a shaft distal portion of an ablation catheter according to the invention comprising a plurality of shaft electrodes and a tip electrode, wherein the outer profile or diameter of the shaft electrodes and the outer profile of the tip electrode are bigger than the outer profile or diameter of the shaft distal portion;

FIG. 45 shows a radiography of an ablation assembly according to the present invention, wherein a catheter distal portion is shown in two different shapes and deflections;

FIG. 46 shows a side view of an ablation catheter handle of the ablation assembly according to an embodiment;

FIG. 47*a*-47*c* shows a schematic lateral view of three different configuration of an ablation catheter, wherein the ablation catheter have different stiffness along its length, wherein the ablation catheter is symmetrical deflectable, or asymmetrical deflectable, and/or wherein the plurality of catheter shaft portions between two electrodes have a first stiffness, the remaining portion of the shaft distal portion have a second stiffness and the shaft proximal portion have a third stiffness;

FIG. 48 shows a side view of a shaft distal portion and a set of different tip electrodes, wherein each tip electrode can be coupled to the shaft distal portion;

FIG. 49 shows a side view of different shaft distal portion of different ablation catheters;

FIG. 50 shows a perspective view of different distal ablation assemblies which can be coupled to the shaft distal portion;

FIG. 51 shows an exploded side view of a tubular shaft electrode and two portions of a shaft distal portion;

FIG. 52 shows a side schematic view of an ablation catheter assembly according to an embodiment;

FIG. 53 shows a section side view of different ablation catheters and different shape setting mandrels disposed within the ablation catheter, and a shape setting mandrel having a rounded distal end;

FIG. 54 shows an example of operation of the ablation equipment of the invention to generate monopolar electric filed from each electrode with a ground electrode;

FIG. 55 shows an example of operation of the ablation equipment of the invention to generate both a monopolar electric filed from each electrode with a ground electrode and a bipolar electric field between two contiguous electrodes;

FIG. 56 shows a flux diagram of a method for ablation with an ablation assembly of the present invention;

FIGS. 57 and 58 show a side view and a cross-sectional view, respectively, of the shaft distal portion of a catheter showing a shaft ablation assembly comprising a plurality of electrodes according to a first embodiment;

FIGS. 59 and 60 show a side view and a cross-sectional view, respectively, of the shaft distal portion of a catheter, showing a shaft ablation assembly comprising a plurality of electrodes according to a second embodiment;

FIG. 61 shows an embodiment of a bipolar electrode comprising a first electrode having an electrode body that delimits an internal compartment of the first electrode accessible from the outside and a second point like electrode housed in said internal compartment of the first electrode;

FIGS. 62A, 62B, 62C shows an ablation equipment comprising a single power source, a single control unit and a power unit, an ablation catheter and a shape setting mandrel disposed in the ablation catheter, wherein are shown in three different electrical connection configurations between the ablation catheter and the single power source;

FIG. 63 shows a block diagram of a single power source of an ablation equipment comprising a single control unit and a power unit;

FIGS. 64A, 64B, 64C show examples of an electrical signal generated by the single power source of FIG. 63 comprising pulse trains;

FIG. 65 shows an ablation kit comprising at least an ablation assembly and a set of shape setting mandrels;

FIG. 66 shows an ablation catheter kit comprising a first ablation assembly and a second ablation assembly having different deflection configurations FIG. 67 shows an ablation catheter in a schematic section view along its length, wherein steering wires and electrical conductors wires are shown.

DESCRIPTION OF SOME PREFERRED EMBODIMENTS

The present invention can be understood more readily by reference to the following detailed description, examples, drawing, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof. As used throughout, the singular forms “a,” “an” and “the” include plural referents unless the context clearly dictates otherwise. Thus, for example, reference to “a tube segment” can include two or more such tube segments unless the context indicates otherwise. The term “plurality,” as used herein refers to two or more.

Ranges can be expressed herein as from “about” one particular value, and/or to “about” another particular value. When such a range is expressed, another aspect includes from the one particular value and/or to the other particular value. Similarly, when values are expressed as approximations, by use of the antecedent “about,” it will be understood that the particular value forms another aspect. It will be further understood that the endpoints of each of the ranges are significant both in relation to the other endpoint, and independently of the other endpoint.

As used herein, the terms “optional” or “optionally” mean that the subsequently described event or circumstance can or cannot occur, and that the description includes instances where the event or circumstance occurs and instances where it does not.

The term “distal” is understood to mean away from a medical practitioner and towards the body site at which the procedure is performed, and “proximal” means towards the medical practitioner and away from the body site.

In accordance with a general embodiment, an ablation assembly 100 to treat target regions of tissue 41 in organs 44, comprises an ablation catheter 1 and at least a shape setting mandrel 26 disposed within the ablation catheter 1.

Said ablation catheter 1 comprises a catheter elongate shaft 13 having a longitudinal main direction X-X and comprising at least an elongate shaft distal portion 17.

Said shaft distal portion 17 comprises a shaft distal portion distal end 19.

Said ablation catheter 1 comprises an inner lumen 118 arranged within the elongate shaft 13.

According to an embodiment, said catheter elongated shaft 13 comprises a flexible body 207 to navigate through body vessels 208.

Said ablation catheter 1 further comprises a shaft ablation assembly 20 fixedly disposed at said elongate shaft distal portion 17.

Said shaft ablation assembly 20 is configured to deliver both thermal energy for ablating said tissue 41 and non-thermal energy for treating said tissue 41.

Said least a shape setting mandrel 26 is insertable within the inner lumen 118 and removable from the inner lumen 118.

Said at least shape setting mandrel 26 is free to move in respect of the inner lumen 118 avoiding any constraint with said shaft distal portion 17 during the shape setting mandrel insertion.

Said at least a shape setting mandrel 26 comprises at least a pre-shaped configuration and the at least a shape setting mandrel 26 is reversibly deformable between at least a straight loaded configuration and said pre-shaped configuration.

When the at least a shape setting mandrel 26 is fully inserted in the shaft distal portion 17, the shape setting mandrel 26 is configured to shape set said shaft distal portion 17 with said pre-shaped configuration.

In accordance with an alternative embodiment, said shaft distal portion 17 is elastically deformable.

In accordance with an alternative embodiment, when the shape setting mandrel 26 is fully inserted in the shaft distal portion 17, said shaft distal portion 17 is configured to conform to said pre-shaped configuration.

In accordance with an alternative embodiment, when the shape setting mandrel 26 is fully inserted in the shaft distal portion 17 it is defined a mandrel fully inserted position.

In accordance with an alternative embodiment, while the shape setting mandrel 26 slides within the inner lumen 118 towards said mandrel fully inserted position, the shape setting mandrel 26 is configured to variably shape set the shaft distal portion 17 passing from said loaded straight configuration to said pre-shaped configuration.

In accordance with an alternative embodiment, when the shape setting mandrel 26 is fully inserted in the shaft distal portion 17, said shape setting mandrel 26 deform said shaft distal portion 17 at least in a shaft distal portion plane P.

In accordance with an alternative embodiment, said ablation catheter 1 comprises a catheter bend portion 120 proximal to the shaft ablation assembly 20, wherein said catheter bend portion 120 is configured to realize an elbow that steer said shaft distal portion plane P with respect to said longitudinal main direction X-X.

In accordance with an alternative embodiment, at least when the shape setting mandrel 26 is fully inserted in the shaft distal portion 17 said shaft distal portion 17 forms an acute angle ALFA with respect to the shaft longitudinal main direction X-X.

In accordance with an alternative embodiment, wherein when the shape setting mandrel 26 is fully inserted in the shaft distal portion 17, the shape setting mandrel 26 is configured to bend at said catheter bend portion 120.

In accordance with an alternative embodiment, said shape setting mandrel 26 in said pre-shaped configuration comprises a mandrel bend portion 146, and when said shape setting mandrel 26 is fully inserted in said shaft distal portion 17, said mandrel bend portion 146 is disposed in correspondence of said catheter bend portion 120 performing said catheter bend portion 120.

In accordance with an alternative embodiment, when the shape setting mandrel 26 is fully inserted in the shaft distal portion 17, the shaft distal portion 17 takes a circular configuration.

In accordance with an alternative embodiment, the shape setting mandrel 26 comprises a mandrel elastic body 119 capable to deform into at least said straight loaded configuration and to return to said pre-shaped configuration.

In accordance with an alternative embodiment, the shape setting mandrel 26 is made of at least a shape memory alloy.

In accordance with an alternative embodiment, said assembly 100 comprises a mandrel heating element 121 coupled to said shape setting mandrel 26, wherein said heating element 121 is configured to apply heat to said shape setting mandrel 26 so that shape setting mandrel 26 changes shape configuration from said loaded straight configuration to said pre-shaped configuration.

In accordance with an alternative embodiment, said ablation assembly 100 comprises a locking mechanism 122 configured to lock said shape setting mandrel 26 to said shaft distal portion 17 when said shape setting mandrel 26 is in said mandrel fully inserted position.

In accordance with an alternative embodiment, said locking mechanism 122 comprises a retention element 123 that reversibly locks said shape setting mandrel 26 in said mandrel fully inserted position.

In accordance with an alternative embodiment, said retention element 123 is configured to release said shape setting mandrel 26 from said mandrel fully inserted position when a pull force is applied to said shape setting mandrel 26.

In accordance with an alternative embodiment, said retention element 123 is made of metal, metal alloy, rubber or polymer.

In accordance with an alternative embodiment, said shape setting mandrel 26 comprises a ball-tip 125 configured to engage said retention element 123 when said shape setting mandrel 26 is in said fully inserted position.

In accordance with an alternative embodiment, said shape setting mandrel 26 comprises a mandrel distal portion 139.

In accordance with an alternative embodiment, said mandrel distal portion 139 comprises a mandrel seat 140, wherein said retention element 123 is fixed to said shape setting mandrel 26 and partially housed in said mandrel seat 140.

In accordance with an alternative embodiment, said inner lumen 118 proximal to said shaft distal portion distal end 19 presents a neck portion 141, wherein said retention element 123 interferes with said neck portion 141 to lock said shape setting mandrel 26 in said mandrel fully inserted position.

In accordance with an alternative embodiment, said retention element 123 is an O-ring, wherein said mandrel seat 140 is toroidal.

In accordance with an alternative embodiment, the shaft distal portion 17 is deflectable in one or more directions, in one or more deflections shapes and geometries.

In accordance with an alternative embodiment, the shape setting mandrel 26 in the pre-shaped configuration is configured to maintain the deflections of the shaft distal portion 17 in a single plane.

In accordance with an alternative embodiment, the deflection directions are symmetric deflection geometries or asymmetric deflection geometries.

In accordance with an alternative embodiment, the elongate shaft 13 has difference in the stiffness of the shaft along its length.

In accordance with an alternative embodiment, the elongate shaft 13 comprises a shaft proximal portion 14.

In accordance with an alternative embodiment, said shaft proximal portion 14 is more rigid than said shaft distal portion 17.

In accordance with an alternative embodiment, the elongate shaft 13 comprises a shaft transition portion 126 disposed between said shaft proximal portion 14 and said shaft distal portion 17.

In accordance with an alternative embodiment, said shaft transition portion 126 is more rigid than said shaft distal portion 17 and less rigid then said shaft proximal portion 14.

In accordance with an alternative embodiment, said elongate shaft 13 comprises shaft portions having different stiffness, wherein said elongate shaft 13 comprises at least one circumferentially dissymmetric stiffness portions between two of said shaft portions having different stiffness.

In accordance with an alternative embodiment, said elongate shaft 13 is made of Pebax®, or said elongate shaft 13 is braided and made of stainless steel flat wire brake and/or Nylon® strand braid.

In accordance with an alternative embodiment, said ablation catheter 1 comprises at least one steering wire 25 configured to deflect the shaft distal portion 17 in one or more deflection directions, wherein said at least one steering wire 25 is fixedly connected to said shaft distal portion 17.

In accordance with an alternative embodiment, said at least one steering wire 25 comprises a wire proximal extension 142 that is arranged outside with respect to a shaft proximal portion 14.

In accordance with an alternative embodiment, said wire proximal extension 142 comprises a wire gripping portion 143 configured to pull at least one the steering wire 25 for steering the shaft distal portion 17 with shape setting mandrel 26 fully inserted into the shaft distal portion 17.

In accordance with an alternative embodiment, said shaft distal portion 17 comprises a shaft distal portion proximal end 18.

In accordance with an alternative embodiment, said ablation catheter 1 comprises at least two steering wires 25.

In accordance with an alternative embodiment, a first steering wire of said at least two steering wires 25 is fixedly connected proximal to the shaft distal portion distal end 19 or the shaft distal portion proximal end 18.

In accordance with an alternative embodiment, a second steering wire of said at least two steering wires 25 is fixedly connected proximal to the shaft distal portion proximal end 18 or to the shaft distal portion distal end 19.

In accordance with an alternative embodiment, a third steering wire of said at least two steering wires 25 is fixedly connected proximal to the shaft distal portion distal end 19 or to the shaft distal portion proximal end 18.

In accordance with an alternative embodiment, a fourth steering wire of said at least two steering wires 25 is fixedly connected proximal to the shaft distal portion distal end 19 or to the shaft distal portion proximal end 18.

In accordance with an alternative embodiment, said shape setting mandrel 26 comprises a mandrel proximal portion 138, wherein said mandrel proximal portion 138 is disposed outside said inner lumen 118 so that said shape setting mandrel 26 is drivable by a user.

In accordance with an alternative embodiment, said elongate shaft 13 comprises a shaft proximal end 15.

In accordance with an alternative embodiment, said ablation catheter 1 comprises a steering device 144 attached to said shaft proximal end 15.

In accordance with an alternative embodiment, said ablation catheter 1 comprises an handle 103, wherein said steering device 144 is connected to said handle 103.

In accordance with an alternative embodiment, said steering device 144 is drivable in rotation with respect to said handle 103 so that a rotation of said steering device 144 with respect to said handle causes a rotation of said elongate shaft 13.

In accordance with an alternative embodiment, said steering device 144 comprises a through hole 145 in communication with said inner lumen 118.

In accordance with an alternative embodiment, during insertion or removal of the shape setting mandrel 26 within or from said ablation catheter 1 said shape setting mandrel 26 passes through said through hole 145, and wherein when the shape setting mandrel 26 is fully inserted in the shaft distal portion 17, said mandrel proximal portion 138 is outside said steering device 144.

In accordance with an alternative embodiment, when the shape setting mandrel 26 is fully inserted in the shaft distal portion 17, said shape setting mandrel 26 deforms said shaft distal portion 17 at least in a shaft distal portion plane P.

In accordance with an alternative embodiment, said steering device 140 comprises at least two protrusion 147, wherein said at least two protrusions and said shaft distal portion plane P are coplanar to help a user to handle the catheter assembly 1.

In accordance with an alternative embodiment, said ablation assembly 100 comprises a distal ablation assembly 21 disposable at least at said shaft distal portion distal end 19.

In accordance with an alternative embodiment, said distal ablation assembly 21 is configured to deliver both thermal energy for ablating said tissue 41 and non-thermal energy for treating said tissue 41.

In accordance with an alternative embodiment, said distal ablation assembly 21 comprises at least an electrode tip 128 disposable at least at said shaft distal portion distal end 19.

In accordance with an alternative embodiment, said shaft electrodes 127 are arranged along the shaft distal portion 17 spaced apart from each other.

In accordance with an alternative embodiment, said shaft ablation assembly 20 is configured also to map a tissue 41.

In accordance with an alternative embodiment, said electrode tip 128 has an external surface shaped to be atraumatic and resiliently biased in rounded configuration.

In accordance with an alternative embodiment, said shaft electrodes 127 and said electrode tip 128 comprise at least a monopolar electrode 113 and/or at least a bipolar electrode 114.

In accordance with an alternative embodiment, said distal ablation assembly 21 comprises at least one thermocouple 37.

In accordance with an alternative embodiment, said shaft ablation assembly 20 comprises at least one thermocouple 37.

In accordance with an alternative embodiment, the shaft electrodes 127 are five to ten electrodes fixedly attached to the shaft distal portion 17.

In accordance with an alternative embodiment, said electrode tip 128 is fixedly disposed at least at said shaft distal portion distal end 19.

In accordance with an alternative embodiment, said electrode tip 128 is removable from said shaft distal portion distal end 19 and interchangeable with a set of tip electrodes 39, wherein the tip electrodes of said set of tip electrodes 39 have different shapes and dimensions.

In accordance with an alternative embodiment, the shaft electrodes 127 are arranged spaced apart along a length of the shaft distal portion 17 in one of the following configurations:

spaced apart 1-5 cm, and/or spaced apart 2-3 cm, or spaced about 2-5 mm apart, preferably 4 mm apart, when a tension of 4000 volts is applied; or spaced about 6 mm apart when a tension of 5000 volts is applied; and/or wherein each shaft electrode of said plurality of shaft electrodes 127 comprises an exposed length of up to 20-25 mm or 2-4 mm.

In accordance with an alternative embodiment, each shaft electrode of said plurality of shaft electrodes 127 comprises an electrode surface area from about 0.05 cm2 to about 5 cm2 or from about 1 cm2 to about 2 cm2.

In accordance with an alternative embodiment, each shaft electrode of said plurality of shaft electrodes 127 is configured to deliver an electric field to the target tissue with at least one of the following electric field intensity ranges: about 100 V/cm to about 7,000 V/cm; and/or about 200 V/cm to about 2000 V/cm; and/or about 300 V/cm to about 1000 V/cm; and/or about 2,000 V/cm to about 20,000 V/cm.

In accordance with an alternative embodiment, said plurality of shaft electrodes 127 comprise a distal shaft electrode 106, said distal shaft electrode 106 being mounted on the shaft distal portion 17 at a distance of 2-4 mm from the shaft distal portion distal end 19.

In accordance with an alternative embodiment, the shaft electrodes 127 are cylindrical.

In accordance with an alternative embodiment, the shaft electrodes 127 have a profile that is flush with the surface of the shaft.

In accordance with an alternative embodiment, the shaft electrodes 127 present a shaft electrodes outer diameter 36, and the shaft portions between the shaft electrodes 127 present an outer shaft diameter 35 that is slightly smaller than the shaft electrodes outer diameter 36 such that the shaft distal end is more flexible.

In accordance with an alternative embodiment, the shaft electrodes 127 are resiliently biased in circular configuration.

In accordance with an alternative embodiment, the shaft electrodes 127 present a tubular geometry having a wall thickness to outer diameter that approximates a 1:15 ratio.

In accordance with an alternative embodiment, said plurality of shaft electrodes 127 comprise at least a bipolar electrode 114, said bipolar electrode 114 comprising a small electrode 130 and a large electrode 131, wherein the small electrode 130 is isolated from the large electrode 131.

In accordance with an alternative embodiment, at least one of said shaft electrodes 127 comprises at least two conductive portions N electrically isolated from each other, wherein each conductive portion N covers radially less than 180° around the shaft distal portion 17.

In accordance with an alternative embodiment, at least one of said shaft electrodes 127 comprises at least four conductive portions N electrically isolated from each other, wherein each conductive portion N covers radially less than 90° around the shaft distal portion 17.

In accordance with an alternative embodiment, the shaft distal portion distal end 19 is open and the shape setting mandrel 26 is slidable outside said shaft distal portion distal end 19 from said mandrel fully inserted position to a mandrel maximum exposed position.

In accordance with an alternative embodiment, said distal ablation assembly 21 is fixedly disposed at said mandrel distal portion 139.

In accordance with an alternative embodiment, said distal ablation assembly 21 comprises a plurality of mandrel electrodes 132, wherein said mandrel electrodes 132 are axially spaced along said mandrel distal portion 139.

In accordance with an alternative embodiment, said mandrel electrodes 132 comprise at least a monopolar electrode 113 and/or at least a bipolar electrode 114.

In accordance with an alternative embodiment, when said shape setting mandrel 26 is in said mandrel fully inserted position, the shaft electrodes 127 are electrically connected with at least a part of the plurality of mandrel electrodes 119.

In accordance with an alternative embodiment, when said shape setting mandrel 26 is in said mandrel maximum exposed position the shaft electrodes 127 are electrically disconnected from any electrical source.

In accordance with an alternative embodiment, the non-thermal energy is irreversible electroporation energy or, IRE, the thermal energy is radiofrequency energy or RF.

In accordance with an alternative embodiment, the shape setting mandrel 26 is slidable outside the shaft distal portion distal end 19 from a mandrel fully inserted position to a mandrel maximum exposed position. In said mandrel fully inserted position, the mandrel 26 is in said loaded straight configuration, and in said mandrel maximum exposed position, the mandrel is in said pre-shaped configuration.

In accordance with an alternative embodiment, said ablation assembly 100 comprises a single power source 4.

Said shaft ablation assembly 20 comprising at least a plurality of electrodes 127, 113 or 114 fixedly disposed at said elongated shaft distal portion 17. All electrodes of said at least a plurality 127, 113 or 114 being electrically powered by said single power source 4 through an electric signal S to deliver both non-thermal energy for treating the tissue 41 and thermal energy for ablating the tissue 41.

Said single power source 4, when requested, changes continuously said electric signal S in order to power the said least a plurality of electrodes 127, 113 or 114 to deliver from a non-thermal energy to a thermal energy, and vice versa, or to deliver at the same time a combination of thermal energy and non-thermal energy.

In accordance with an alternative embodiment, said single power source 4 comprises a single control unit 400 and a power unit 401 for generating said electric signal S.

In accordance with an alternative embodiment, said power unit 401 being electrically connected to all electrodes of said at least a plurality of electrodes 127, 113 or 114.

In accordance with an alternative embodiment, said power unit 401 is driven by the single control unit 400 to change continuously the electric energy level associated to the signal S to be supplied to the electrodes 127, 113 or 114 to deliver from a non-thermal energy to a thermal energy, and vice versa, or to deliver a combination of thermal energy and non-thermal energy at the same time.

In accordance with an alternative embodiment, said power unit 401 comprises a power module 402. Said power module 402 comprises:

a drive circuit block 403 controlled by the single control unit 400 for generating said electric signal S starting from a supply voltage signal Vcc provided by the single control unit 400;

a selecting block 404 selectively controlled by said drive circuit block 403 to change continuously the electric energy level associated to said signal S;

a filtering and electrical isolation block 405, 406.

In accordance with an alternative embodiment, said single control unit 400 comprises a Microprocessor 407 configured to control a variable High Voltage Power Supply block 408 and a Programmable Logic Controller block 409.

Said variable High Voltage Power Supply block 408 being configured to provide said supply voltage signal Vcc to the power module 402 for generating said electric signal S.

Said Programmable Logic Controller block 409 being configured to generate drive signals to control the drive circuit block 403 of the power module 402.

In accordance with an alternative embodiment, said single control unit 400 further comprises:

a Video interface and Push Button block 410, 410' controlled by the Microprocessor 407 to set parameters of the equipment 100 and display the selected parameters;

a Watch Dog block 411 for controlling proper functioning of the Microprocessor 407;

an Audio interface block 412 for providing audio information representative of correctness of the ablation process and/or errors occurred.

In accordance with an alternative embodiment, said power unit 401 comprises one or more power modules 402 equal to each other.

In accordance with an alternative embodiment, at least one of said electrodes 127, 113 is a monopolar electrode 113, and said monopolar electrode 113 of said at least a plurality of electrodes is electrically connected to only one power module 402 of said power unit 401.

In accordance with an alternative embodiment, at least two of said electrodes 127, 114 are electrically connected to form a bipolar electrodes 114, and said bipolar electrodes 114 of said at least a plurality of electrodes are electrically connected separately to respective power module 402 selectable among the power modules of said power unit 401. In accordance with an alternative embodiment, said electric signal S to be supplied to the electrodes of said plurality 127, 113 or 114 comprises pulse trains 204. In accordance with an alternative embodiment, said single control unit 400 is configured to drive the power unit 401 to modify the pulse duration 203 of each pulse 201 in the pulse trains 204 to change the electric energy level associated with the signal S.

In accordance with an alternative embodiment, said single control unit 400 is configured to drive the power unit 401 to modify the number of pulses 209 in the pulse train 204 to change the electric energy level associated with the signal S.

In accordance with an alternative embodiment, said single control unit 400 is configured to drive the power unit 401 to modify the gap of time 205 between adjacent pulse trains 204 to change the electric energy level associated with the signal S. In accordance with an alternative embodiment, each monopolar electrode 113 of said least a plurality of electrodes is electrically connected to the corresponding power module 402 of said power unit 401 by a single wire 210 welded to the monopolar electrode 113.

In accordance with an alternative embodiment, each bipolar electrode 114 of said least a plurality of electrodes is electrically connected to the two selected power modules 402 of said power unit 401 by two wires 210 welded to the bipolar electrode 114.

In accordance with an alternative embodiment, said electric signal S to be supplied to the electrodes of said plurality 127, 113 or 114 comprises at least a square wave signal.

In accordance with an alternative embodiment, said electric signal S to be supplied to the electrodes of said plurality 127, 113 or 114 comprises a signal obtained by combining or summing or superimposing two or more square wave signals each other.

In accordance with an alternative embodiment, said electric signal S to be supplied to the electrodes of said plurality 127, 113 or 114 comprises a DC signal or an AC signal or a combination of a DC signal and an AC signal.

In accordance with an alternative embodiment, said single power source 4 is powered by a battery or is connected to a standard wall outlet of an AC electrical power grid capable of producing 110 volts or 240 volts.

In accordance with an alternative embodiment, said least two electrodes 127, 114 electrically connected to form a bipolar electrodes 114 comprise:

a first electrode **114*a* connected to a first power module 402 of said power unit 401 by a first wire 210*a*, said first electrode 114*a* having an electrode body 424 that delimits an internal compartment of the first electrode 114*a* accessible from the outside of the first electrode 114*a*;**

a second point like electrode **114*b* connected to a second power module 402 of said power unit 401 by a second wire 210*b*, said second point like electrode 114*b* being housed in said internal compartment of the first electrode 114*a***.

In accordance with an alternative embodiment, the single control unit 400 is configured to drive said power unit 401 to generate in each power module 402 a respective electric signal S of a plurality of electric signals S to be supplied to the electrodes 127, 113 or 114, said Microprocessor 407 being configured to control, through said Programmable Logic Controller block 409, each power module 402 to modify the ON status, the OFF status and the phase angle of each electric signal S of said plurality of electric signals so that, by selecting two or more electric signals S supplied to the electrodes 127, 113 or 114, both a monopolar electric filed from each electrode with a ground electrode 425 and a bipolar electric field between two contiguous electrodes is generated.

The present invention refers also to a method for controlling at least a plurality of electrodes 127, 113 or 114 in an ablation assembly or equipment 100 comprising an ablation catheter 1 and a single power source 4 according to the embodiments previously described. The method comprising:

generating, by said single power source 4, an electric signal S comprising pulse trains 204 for electrically powering all electrodes of said at least a plurality 127, 113 or 114;

modifying the pulse duration 203 of each pulse 201 in the pulse trains 204, or modifying the number of pulses 209 in the pulse train 204, or modifying the gap of time 205 between adjacent pulse trains 204, to induce said least a plurality of electrodes 127, 113 or 114 to deliver from a non-thermal energy to a thermal energy, and vice versa, or to deliver at the same time a combination of thermal energy and non-thermal energy.

In accordance with an alternative embodiment, each monopolar electrode 113 of said least a plurality of electrodes is electrically connected to the corresponding power module 402 of said power unit 401 by a single wire 210 welded to the monopolar electrode 113.

In accordance with an alternative embodiment, each bipolar electrode 114 of said least a plurality of electrodes is electrically connected to the two selected power modules 402 of said power unit 401 by two wires 210 welded to the bipolar electrode 114.

The present invention refers also to an ablation kit 200. Said ablation kit 200 comprises:

at least an ablation equipment 100 according to any one of the preceding embodiments;

a set of shape setting mandrels 134.

The shape setting mandrels of said set 134 have different pre-shaped configurations.

The shape setting mandrels of said set 134 are alternatively disposable and removable in said ablation catheter 1.

According to an alternative embodiment, said set of shape setting mandrels 134 comprises at least a first shape setting mandrel 135 and a second shape setting mandrel 136.

The first shape setting mandrel 135 has a first pre-shaped configuration and the second shape setting mandrel 136 has a second pre-shaped configuration.

Said first pre-shaped configuration is different than said second pre-shaped configuration so that different shapes of shaft distal portion 17 are performed depending on which shape setting mandrel 135, 136 of said set of setting mandrels 134 is disposed into the ablation catheter 1.

In accordance with an alternative embodiment, at least one shape setting mandrel of said set of shape setting mandrels 134, has a circular pre-formed configuration.

In accordance with an alternative embodiment, at least one shape setting mandrel of said set of shape setting mandrels 134, has a spiral pre-formed configuration.

In accordance with an alternative embodiment, at least one shape setting mandrel of said set of shape setting mandrels 134 has a straight pre-formed configuration.

In accordance with an alternative embodiment, at least one shape setting mandrel of said set of shape setting mandrels 134 has a circular pre-formed configuration provided with an elbow.

The present invention furthermore refers to ablation catheter Kit 300.

The ablation catheter kit 300 comprises at least a first ablation assembly 100 and a second ablation assembly 100' according to any of the preceding described embodiments.

The shaft distal portion 17 of the ablation catheter 1 of the first ablation assembly 100 is deflectable in at least two symmetric geometries.

The shaft distal portion 17' of the ablation catheter 1' of the second ablation assembly 100' is deflectable in in at least two asymmetric geometries.

The present invention furthermore refers to a method for set shaping an ablation catheter, comprising the following steps:

providing an ablation assembly 100 according to any embodiment previously described, inserting said shape setting mandrel 26 in said loaded straight configuration within said inner lumen 118 of said ablation catheter 1, moving said shape setting mandrel 26 within said inner lumen 118 towards the shaft distal portion distal end 19 until the shape setting mandrel 26 is fully inserted into said shaft distal portion 17, and conforming the shape of shaft distal portion 17 to the pre-shaped configuration of said shape setting mandrel 26 when the shape setting mandrel 26 is fully inserted into said shaft distal portion 17.

The present invention furthermore refers to a method for multiple set shaping an ablation catheter, comprising the following steps:

providing an ablation kit 200 as previous described, inserting the first shape setting mandrel 135 within the ablation catheter 1, conforming the shaft distal portion 17 of the elongate shaft 13 of the ablation catheter 1 to the shape of the first pre-formed configuration of the first shape setting mandrel 135, removing the first shape setting mandrel 135 from the elongate shaft 13 of the ablation catheter 1, inserting the second shape setting mandrel 136 within the ablation catheter 1, and conforming the shaft distal portion 17 to the shape of the second pre-formed configuration of the second shape setting mandrel 136.

The present invention furthermore refers to a method for controlling at least a plurality of electrodes 127, 113 or 114 in an ablation equipment 100. Said ablation equipment comprises an ablation catheter 1 and a single power source 4 according to anyone of the embodiments described before.

The method comprises the following steps:

generating, by said single power source 4, an electric signal S comprising pulse trains 204 for electrically powering all electrodes of said at least a plurality 127, 113 or 114;

modifying the pulse duration 203 of each pulse 201 in the pulse trains 204, or modifying the number of pulses 209 in the pulse train 204, or modifying the gap of time 205 between adjacent pulse trains 204, to induce said least a plurality of electrodes 127, 113 or 114 to deliver from a non-thermal energy to a thermal energy, and vice versa, or to deliver at the same time a combination of thermal energy and non-thermal energy.

Thanks to the solutions proposed, it is possible to provide a method for set shaping an ablation catheter, comprising the following steps:

providing an ablation equipment 100 according to anyone of the above described embodiments, inserting said shape setting mandrel 26 in said loaded straight configuration within said inner lumen 118 of said ablation catheter 1, moving said shape setting mandrel 26 within said inner lumen 118 towards the shaft distal portion distal end 19 until the shape setting mandrel 26 is fully inserted into said shaft distal portion 17, and conforming the shape of shaft distal portion 17 to the pre-shaped configuration of said shape setting mandrel 26 when the shape setting mandrel 26 is fully inserted into said shaft distal portion 17.

Thanks to the solutions proposed, it is possible to provide a method for the treatment of proximal, persistent or long-standing persistent atrial fibrillation in a patient comprising the following steps:

providing an ablation assembly 100 according to anyone of the above described embodiments;

placing the ablation catheter 1 in the coronary sinus of the patient, such as to map electrograms and/or ablate tissue, and subsequently;

place the ablation catheter 1 in the left or right atrium to map electrograms and/or to deliver energy for treating a tissue 41 at least with the a shaft ablation assembly 20 with the shaft distal portion 17 shaped at a pre-shaped configuration imposed by the shape setting mandrel 26 fully inserted in the shaft distal portion 17, place the ablation catheter in the left or right atrium to deliver energy for treating a tissue at least with the a shaft ablation assembly 20 with the shaft distal portion 17 shaped at a pre-shaped configuration imposed by the shape setting mandrel 26 fully inserted in the shaft distal portion 17, wherein the tissue locations include fasicals around a pulmonary vein, and/or the left atrial roof, and/or the mitral isthmus.

Thanks to the solutions proposed, it is possible to provide a method for the treatment of atrial flutter in a patient comprising the following steps:

providing an ablation assembly 100 according to anyone of the above described embodiments;

placing the ablation catheter 1 in one or more locations in the right atrium of the heart to achieve bi-directional block delivering energy for treating a tissue 41 at least with the a shaft ablation assembly 20 with the shaft distal portion 17 shaped at a pre-shaped configuration imposed by the shape setting mandrel 26 fully inserted in the shaft distal portion 17.

Thanks to the solutions proposed, it is possible to provide a method of ablating tissue in the right atrium of the heart comprising the following steps:

providing an ablation assembly 100 according to anyone of the above described embodiments;

placing the ablation catheter 1 in one or more locations in the right and/or left atrium of the heart 43;

creating lesions between the superior vena cava and the inferior vena cava and/or the coronary sinus and the inferior vena cava and/or the superior vena cava and the coronary sinus by delivering energy for treating a tissue at least with the a shaft ablation assembly 20 with the shaft distal portion 17 shaped at a pre-shaped configuration imposed by the shape setting mandrel 26 fully inserted in the shaft distal portion 17.

Thanks to the solutions proposed, it is possible to provide a method for the treatment of sinus node tachycardia in a patient comprising the following steps:

providing an ablation assembly 100 according to anyone of the above described embodiments;

placing the ablation catheter 1 in one or more locations in the right and/or left atrium of the heart 43;

mapping electrograms sinus node and/or mapping sinus node and/or ablating the sinus node delivering energy for treating a tissue at least with the a shaft ablation assembly 20 with the shaft distal portion 17 shaped at a pre-shaped configuration imposed by the shape setting mandrel 26 fully inserted in the shaft distal portion 17.

Thanks to the solutions proposed, it is possible to provide a method for the treatment of ventricular tachycardia in a patient comprising the following steps:

providing an ablation assembly 100 according to anyone of the above described embodiments;

placing the ablation catheter 1 in the left or right ventricles of the heart 43;

inducing ventricular tachycardia by delivering pacing energy, and ablating tissue to treat the patient by delivering energy for treating a tissue at least with the shaft ablation assembly 20 with the shaft distal portion 17 shaped at a pre-shaped configuration imposed by the shape setting mandrel 26 fully inserted in the shaft distal portion 17.

Thanks to the solutions proposed, it is possible to provide a method to ablate atrial tissues comprising the following steps:

providing an ablation assembly 100 according to anyone of the above described embodiments;

wherein the shaft distal portion 17 comprises a first deflection geometry when the shape setting mandrel 26 is fully inserted in the elongate shaft 13, and the shaft distal portion 17 comprises a second deflection geometry when the shape setting mandrel 26 is removed from the shaft distal portion 17, wherein the first deflection geometry is larger than the second deflection geometry;

placing the ablation catheter 1 exposed to an atrial tissue, with the shaft distal portion 17 in the second deflection geometry with said shape setting mandrel 26 outside said distal portion 17;

ablating one or more of the following tissue locations: left atrial septum; tissue adjacent the left atrial septum; and tissue adjacent the left atrial posterior wall;

placing the ablation catheter 1 with the shaft distal portion 17 in the first deflection geometry by fully inserting the shape setting mandrel 26 within the elongate shaft 13, ablating at least the circumference around the pulmonary veins.

The present invention furthermore refers to a use of the kit according to anyone of the above described embodiments and to treat both the left and right atria of a heart, wherein the ablation catheter 1 of the ablation assembly 100 is used to ablate tissue in the right atrium using at least the first shape setting mandrel 135, and the same ablation catheter 1 is used to also ablate tissue in the left atrium using at least the second shape setting mandrel 136.

Reference will now be made in detail to the present embodiments of the invention, examples of which are illustrated in the accompanying drawings.

Configured to be percutaneously advanced into Left Atrium and Left Ventricle of Heart (through septum via transseptal sheath).

May be advanced through sheath previously placed in LA (e.g. deflectable or fixed cure sheath).

Elongate Catheter Body 13, 207 May be steerable (uni-directional or bidirectional)

e.g. one pull wire 25 e.g. two pull wires 25 e.g. attached near distal tip with _180° separation e.g. attached near distal tip with _90° separation e.g. four pull wires 25 e.g. attached near distal tip with _90° separation

May be Asymmetric steerable curves e.g. spring to restrict curve radius in one plane and not the opposing plane Construction Pref PeBax Braided, (SS flat wire braid, Nylon strand braid, combination)

Pref has a transition 126 from more rigid proximal end to less rigid distal end 1st Control Shaft (Outer)

Distal End attached to distal end of Single Atraumatic Electrode Tip
Distal End attached to distal end of Split Atraumatic Electrode Tip
Distal End attached to distal end of Quartered Atraumatic Electrode Tip
Distal End pref attached to atraumatic tip electrode
Shaft preferably has a lumen for Saline Flush
Shaft preferably has a lumen for isolating signal wires
Shaft preferably has side hole ports at 90° separation about the diameter at various locations on the distal section.
Side hole ports allow signal wires to pass from inside to outside
Prox End attached to Handle
Alt Design—shaft may have 1 or more electrical (power/signal) wires 210 (connected to
electrodes/thermocouples on Single Wire Segment)
Includes multiple Electrodes along its length
Side hole ports allow saline flush to exist inside control shaft lumen 118
Holes in segment—underneath electrodes—wires feed through holes
Having cylindrical electrodes mounted 2-4 mm from distal tip and 2-3 mm apart
2nd Lumen 118—multi-purpose (fluid flush and shape setting mandrel)
Runs from proximal to distal inside 1st lumen.
Attached to proximal end of Handle with port for either saline delivery and/or a shape setting
Mandrel
Attached to the Control shaft proximal to the distal electrodes
Prox End of Shaft attached to Control on Handle
Pref constructed to withstand high pressure fluid flow while being soft and flexible
Atraumatic Electrode Tip
Resiliently biased in rounded configuration
Includes at least one Thermocouple
e.g. thermocouple integral to an electrode
Cylindrical Shaft Electrodes
Resiliently biased in circular configuration
Holes in segment—underneath electrodes—wires feed through holes
Includes at least one Thermocouple
e.g. thermocouple integral to an electrode
Electrodes
Construction
Platinum, Platinum/Iridium
>2 mm in length
<4 mm in length
Pref include thermocouple
Copper and Constantine wires
Welded to inside portion of electrode
Alt Design—electrodes could have fins, other heat sinks
Handle
On proximal end of Catheter Body
Lever (single)—connected to the two pull wires for tip deflection
1st Sliding Knob for asymmetrical steering engagement
Attaches to 1st Control Shaft
Attaches to 2nd Control Shaft
Pref—includes energy activation control
ALT—single Control Shaft
Attached to either distal or proximal end of Atraumatic Electrode Tip.

According to alternative embodiments, the present invention provides catheters 1, or ablation assembly 100, for performing various targeted tissue ablation in a subject. According to alternative embodiments, the catheters comprise an elongate shaft 13 having a proximal end 15 and distal end 16 and preferably a lumen, or inner lumen 118, extending at least partially therebetween. The catheter is preferably of the type used for performing intracardiac procedures, typically being introduced from the femoral vein in a patient's leg or from a vessel in the patient's neck. The catheter is preferably introducible through a transport tube, such as a transeptal sheath, and also preferably has a steerable tip that allows positioning of the distal portion 17 such as when the distal end of the catheter is within a heart chamber. The catheters include ablation elements 23, or tip ablation elements 23, located at the distal end of the shaft (tip electrodes 128), as well as ablation elements 22, or shaft ablation elements 22, located on or in the exterior surface of the shaft proximal to the distal end (tube electrodes or shaft electrodes 127). The tip electrodes 128 may be fixedly attached to the distal end of the shaft, or may be mounted on an advancable and/or expandable carrier assembly. The carrier assembly may be attached to a control shaft that is coaxially disposed and slidingly received within the lumen of the shaft. The carrier assembly is deployable by activating one or more controls on a handle 103 of the catheter 1, such as to engage one or more ablation elements against cardiac tissue, typically atrial wall tissue or other endocardial tissue. The shaft may include deflection means, such as means operably connected to a control on a handle of the catheter or through a center lumen where different shape mandrels 26 can be placed to change the catheter distal section shape. The deflection means may deflect the distal portion of the shaft in one or more directions, such as deflections with two symmetric geometries, two asymmetric geometries, or combinations of these. Asymmetries may be caused by different radius of curvature, different length of curvature, differences in planarity, other different 2-D shapes, other different 3-D shapes, and the like.

In particular, according to alternative embodiments, the present invention provides ablation catheters with multiple electrodes that provide electrical energy, such as Radio Frequency (RF) and/or IRreversible electroporation (IRE) which occurs when a strong, pulsed electrical field (PEF) causes permeabilization of the cell membrane, leading to cellular homeostasis disruption and cell death. Radiofrequency (RF) energy, in monopolar (unipolar), bipolar or combined unipolar-bipolar fashion, as well as methods for treating conditions such as paroxysmal atrial fibrillation, chronic atrial fibrillation, atrial flutter, supra ventricular tachycardia, atrial tachycardia, ventricular tachycardia, ventricular fibrillation, and the like, with these devices.

The normal functioning of the heart relies on proper electrical impulse generation and transmission. In certain heart diseases (e.g., atrial fibrillation) proper electrical generation and transmission are disrupted or are otherwise abnormal. In order to prevent improper impulse generation and transmission from causing an undesired condition, the ablation catheters and RF generators of the present invention may be employed.

One current method of treating cardiac arrhythmias is with catheter ablation therapy. Physicians make use of catheters to gain access into interior regions of the body. Catheters with attached electrode arrays or other ablating devices are used to create lesions that disrupt electrical pathways in cardiac tissue. In the treatment of cardiac arrhythmias, a specific area of cardiac tissue having aberrant conductive pathways, such as atrial rotors, emitting or conducting erratic electrical impulses, is initially localized. A user (e.g., a physician) directs a catheter through a main vein or artery into the interior region of the heart that is to be treated. The ablating element (or elements) is next placed near the targeted cardiac tissue that is to be ablated. The physician directs energy, provided by a source external to the patient, from one ore more ablation elements to ablate the neighboring tissue and form a lesion. In general, the goal of catheter ablation therapy is to disrupt the electrical pathways in cardiac tissue to stop the emission and/or prevent the propagation of erratic electric impulses, thereby curing the focus of the disorder. For treatment of atrial fibrillation AF, currently available methods and devices have shown only limited success and/or employ devices that are extremely difficult to use or otherwise impractical.

The ablation systems of the present invention allow the generation of lesions of appropriate size and shape to treat conditions involving disorganized electrical conduction (e.g., AF). The ablation systems of the present invention are also practical in terms of ease-of-use and limiting risk to the patient (such as in creating an efficacious lesion while minimizing damage to untargeted tissue), as well as significantly reducing procedure times. The present invention addresses this need with, for example, arrangements of one or more tip ablation elements and one or more shaft ablation elements configured to create a linear lesion in tissue, such as the endocardial surface of a chamber of the heart, by delivery of energy to tissue or other means. The electrodes of the present invention may include projecting fins or other heat dissipating surfaces to improve cooling properties. The distal portions of the catheter shafts of the present invention may deflect in two or more symmetric or asymmetric geometries, such as asymmetric geometries with different radius of curvature or other geometric shape differences. The ablation catheters and RF generators of the present invention allow a clinician to treat a patient with AF in a procedure much shorter in duration than current AF ablation procedures. The lesions created by the ablation catheters and RF generators of the present invention are suitable for inhibiting the propagation of inappropriate electrical impulses in the heart for prevention of reentrant arrhythmias, while minimizing damage to untargeted tissue, such as the esophagus or phrenic nerve of the patient.

Referring to the figures, one embodiment of an energy delivery system for selectively ablating tissue, or ablation equipment or assembly 100, is illustrated. In one aspect, the system can comprise at least one energy delivery device, or ablation catheter 1, such as, but not limited to, a monopolar probe 101, and at least one energy delivery source or power source, or single power source, 4. In one aspect, at least a portion of the probe can be configured for insertion into a patient. In one aspect, the at least one energy source, or single power source 4, can further comprise at least a non-thermal energy source 6 and a thermal energy source 7. In one aspect, the system can comprise a mechanism for coupling the probe to one desired energy source of the at least one energy source 8, or probe connector. In one aspect, although a monopolar probe is described herein, one of ordinary skill in the art will recognize that the energy delivery device used with the system described herein can be a different type of energy delivery device, such as, but not limited to, a bipolar probe 102. In one aspect, the probe can be selected from a group consisting of: a monopolar electrode 113, a bipolar electrode 114, and an electrode array 111, such as shaft electrodes 127, mandrel electrodes 132, and tip electrode 128.

This can allow for utilization of an optimal energy delivery device for a given medical procedure. In one aspect, the monopolar probe 101 can comprise a handle 103, a electrode having a proximal end, or electrode proximal end 104, and a distal end, or electrode distal end 105, and at least one connector of the probe. In one aspect, the electrode(s) can comprise at least one distal electrode 106 that is positioned therein at the distal end of the probe and round electrodes 107 positions on the body of the probe that is positioned in the heart chamber. In one aspect, the tip can be a rounded conical type shape and can be capable of sliding along the wall of the heart and said probe designed to allow the sliding to match the heart wall motion.

In one aspect, at least one monopolar probe, as described above, can be used with system. In another aspect, although not illustrated, at least two monopolar electrodes 113, as described above, can be used with system. In one exemplary embodiment, it is contemplated that if more than one electrode is used in the system, the probes can be used in various configurations and shapes, such as, but not limited to, a parallel configuration or a spiral configuration. In one aspect, if two electrodes are used, it is contemplated that the distal electrode would be one and each of the body electrodes would be selected based on the length requirements of the ablation. In another exemplary aspect, the electrodes can be positioned such that the distal tip can be staggered in length compared to a body electrode. In one exemplary embodiment, if at least two electrodes are used in the system, the at least two electrodes can be spaced about 2-5 mm apart while mounted on the catheter body inserted into heart chamber and can provide a voltage of up to 4000 volts. In yet another exemplary embodiment, the at least two electrodes can be spaced about 6 mm apart or greater be selecting alternate electrodes on catheter body and can have a voltage of up to about 5000 volts. In one exemplary embodiment, the at least two electrodes can be spaced from each other such that they are approximately 4 mm apart while inserted into a target tissue and can provide a voltage of up to approximately 4000 volts.

In one aspect, the at least one electrode of the monopolar probe can be configured to be electrically coupled to and energized by energy source. Further, although not shown, one of ordinary skill in the art would recognize that at least one grounding pad 108 can be used in conjunction with the at least one electrode to complete an electrical circuit 109. Although a single electrode configuration is described herein, it is contemplated that other various needle 110 and/or electrode array formations could be used in any of the embodiments described herein. An array herein refers to an orderly arrangement of multiple probes 111. In one aspect, this array could be a plurality or series of monopolar and/or bipolar probes arranged in various shapes, configurations, or combinations in order to allow for the ablation of multiple shapes and sizes of target regions of tissue. Various array patterns can reduce the need to reposition the electrode array during treatment by allowing multiple selectively activatable electrode patterns 112. In one aspect, the electrodes can be of different sizes and shapes, such as, but not limited to, square, oval, rectangular, circular or other shapes. In one aspect, the electrodes described herein can be made of various materials known in the art.

In one aspect, the electrodes described herein can be exposed up to various lengths. In one aspect, the electrodes can have an exposed length of up to approximately 20-25 mm while inserted into tissue, such can be either linear length or circular length as in the case where the at least two electrodes are spaced up to approximately 2-5 mm mm apart on catheter body and distal tip. In another exemplary aspect, the electrodes can have an exposed electrode length of up to approximately 2-4 mm, such as in the case where the at least two electrodes are spaced approximately 2-5 mm apart. In yet another aspect, the electrodes can be spaced at various distances from one another. In one aspect, the electrodes can be spaced apart a distance of from about 0.5 cm to about to 1 cm. In another exemplary embodiment, the electrodes can be spaced apart a distance of from about 1 cm to about 5 cm. In yet another embodiment, the electrodes can be spaced apart a distance of between about 2 cm and about 3 cm. In one exemplary aspect the electrode surface area can vary. In one exemplary embodiment, the electrode surface area can vary from about 0.05 cm2 to about 5 cm2. In yet another exemplary embodiment, the electrodes can have a surface area of between about 1 cm2 to about 2 cm2.

In one aspect, the system can comprise a means 11, 12 for selectively energizing a desired energy source to ablate at least a portion of the tissue adjacent to the at least one probe. In one aspect, the non-thermal energy source 6 of the at least one energy source or single power source 4, can be selectively energized to apply non-thermal energy to at least a portion of the desired tissue region to ablate at least a portion of the desired tissue region 45. Thus, in one aspect, the energy source can be configured to deliver non-thermal energy, such as, but not limited to, irreversible electroporation (IRE) energy to target tissue. In one exemplary embodiment, the thermal energy source can be an RF energy source. In one aspect, although not shown, during use of the system, the at least one electrode/probe can be selectively coupled to the non-thermal energy source, and the non-thermal energy source can be selectively energized to apply nonthermal energy from the non-thermal energy source to at least a portion of the desired tissue region to ablate at least a portion of the desired tissue region In one exemplary aspect, the at least one energy source can have at least one connector 8 that is configured for selective coupling to the at least one electrode/probe. In one aspect, the energy source can have a positive connector 9 and a negative connector 10. More particularly, the at least one connector of the electrode/probe can be connected to the energy source via at least one of the positive connector and the negative connector.

In one exemplary embodiment, the power source or energy source can be a Argá model 100 electrosurgical generator capable of delivering up to 1000 watts of RF power. One of ordinary skill in the art would recognize that a variety of generator models could be used with the system described herein. In one aspect, the generator can be powered by a battery 5. In one aspect, the generator can be connected to a standard wall outlet that is capable of producing about 110 volts or about 240 volts. In one aspect, the power supply can be capable of being manually adjusted, depending on the voltage. In one exemplary embodiment, the generator can be capable of producing a minimum voltage of about 100 volts to about 4000 volts. In one aspect, at least one of the power outlets, generators, and battery sources described herein can be used to provide voltage to the target tissue during treatment. In yet another exemplary embodiment, to achieve IRE ablation of the target region of tissue, the power source or generator can be used to deliver IRE energy to target tissue, including target tissue that can be somewhat difficult to reach. In one aspect, an exemplary embodiment of an IRE generator can include anywhere from 2 to 10 positive and negative connectors, though one of ordinary skill in the art would understand that other numbers of positive and negative connectors and different embodiments of connectors could be used and may be and necessary for optimal ablation configurations. A system in which a bipolar probe 102 is used. In one aspect, the bipolar probe 102 can comprise a handle 103, electrode having a proximal end 104 and a distal end 105, and at least one probe connector 9. In one aspect, the electrode can comprise at least one electrode that is positioned therein at the distal end of the catheter and that is positioned at a distal most portion of the ablation elements. In one aspect, the electrode can further comprise a first electrode 115 that is positioned at the distal most portion of the catheter, a second electrode 116 that is positioned proximal of the distal electrode, and at least one spacer 117 that can be positioned between and adjacent to at least a portion of each of the first and second electrodes and the third, etc. electrode. In one aspect, at least a portion of a distal portion of the second electrode can abut at least a proximal portion of spacer and at least a distal portion of spacer can abut at least a portion of a proximal portion of the first electrode. In one aspect, similar to monopolar probe, the bipolar probe can be coupled to a thermal energy source 8. During use of the system, the probe can be coupled to the energy source. More particularly, in one exemplary aspect, at least one connector of the probe 8 can be connected to the energy source via at least one of the positive connectors 9 and the negative connector 10, as also described above.

Depending on various parameters, such as voltage (including application of DC or AC or both as well as voltage per square centimeter), current, pulse number 209, pulse duration 203, and the dwell between pulses applied to tissue, or gap of rime between adjacent pulses 205, the tissue can be subjected to reversible electroporation, irreversible electroporation, or thermal damage (generally considered to be resistive heating). Nonthermal IRE ablation involves ablation where the primary method of cellular disruption leading to death is mediated via electroporation (rather than factors such as effects of or responses to heating). In certain embodiments, depending on the parameters mentioned (including time that the resulting temperature occurs), cellular death can be mediated via nonthermal IRE up to approximately >46 degrees C. In certain embodiments cellular damage from thermal heating occurs above approximately >46 degrees C. In various embodiments, the parameters resulting in nonthermal IRE can be changed to result in the death of cells via thermal heating. The parameters can also be changed to from one having nonthermal IRE effects to alternative settings where the changed parameters also have nonthermal IRE effects.

More particularly, in one aspect, the total number of pulses 209 and pulse trains 204 in various embodiments can be varied based on the desired treatment outcome and the effectiveness of the treatment for a given tissue. During delivery of non-thermal IRE energy to target tissue, a voltage can be generated that is configured to successfully ablate tissue. In one aspect, certain embodiments can involve pulses between about 1 microsecond and about 80,000 milliseconds, while others can involve pulses of about 75 microseconds and about 20,000 milliseconds. In yet another embodiment, the ablation pulse applied to the target tissue 47 can be between about 20 microseconds and 100 microseconds. In one aspect, the at least one energy source can be configured to release at least one pulse of energy for between about 100 microseconds to about 100 seconds and can be adjustable at 10 microsecond intervals. In certain embodiments the electrodes described herein can provide a voltage of about 100 volts per centimeter (V/cm) to about 7,000 V/cm to the target tissue. In other exemplary embodiments, the voltage can be about 200 V/cm to about 2000 V/cm as well as from about 300 V/cm to about 1000 V/cm. Other exemplary embodiments can involve voltages of about 2,000 V/cm to about 20,000 V/cm. In one exemplary aspect, the bipolar probe 100 can be used at a voltage of up to about 2700 volts.

In one aspect, the number of pulses 209 that can be used in IRE ablation can vary. In certain exemplary embodiments the number of pulses 209 can be from about 1 pulse to about 25 pulses. In other exemplary embodiments, groups of about 1 pulse to about 25 pulses can be applied in succession following a gap of time between each pulse group or pulse train. In one exemplary embodiment the gap of time between groups of pulses can be about 0.05 second to about 2 seconds. In one aspect, pulses can be delivered to target tissue using energy delivery devices, such as, but not limited to, probes, electrodes, and other conductive materials. In one aspect, such energy delivery devices can be of varying lengths suitable for use in procedures such as, but not limited to, percutaneous, laparoscopic, and open surgical procedures. In one aspect, the at least one energy source can be configured to release at least one pulse of energy for between about 5 microseconds to about 10 seconds. In one exemplary aspect, the voltage described herein can be applied using the bipolar electrodes 114 in pulses of 5 microseconds in length to a target region of tissue. In one aspect, the voltage can be applied in pulses of about 1 microsecond in groups of pulses or pulse-trains of 10, with an interval between pulses of about 50 milliseconds and a time between pulse-trains of about 0.5 seconds.

In one exemplary aspect, at least two monopolar electrodes 113 can be used to ablate target tissue, such that a zone of ablated tissue is produced that is approximately 20-25 m×5-10 mm. In one exemplary embodiment, two single electrodes can be configured so as to involve other ablation areas, including, but not limited to, an ablation area of approximately 30 m×25 mm. One of ordinary skill in the art would be understood that the ablation size and shape can be advantageously varied with placement of the electrode and various electrode types. In one aspect, during treatment, an additional area surrounding an outer edge of the target region of tissue is also ablated (ablation of unwanted or diseased tissue). This surrounding area of tissue can be ablated in order to ensure patient safety and the complete and adequate ablation of the target region of tissue. In one aspect, during the method of use, the catheter electrode tip 128 of the catheter is designed as not to puncture a patient's tissue. One of ordinary skill in the art would recognize that the target region of tissue can be any tissue from any organ where ablation can be used to ablate unwanted or diseased tissue, such as, but not limited to, cardiac tissue, digestive, skeletal, muscular, nervous, endocrine, circulatory, reproductive, integumentary, lymphatic, urinary tissue or organs, or other soft tissue or organs where selective ablation is desired. Soft tissue can include, but is not limited to, any tissue surrounding, supporting, or connecting other body structures and/or organs. For example, soft tissue can include muscles, tendons, ligaments, fascia, joint capsules, and other tissue. More specifically, target tissue can include, but is not limited to, areas of the heart, the prostate (including cancerous prostate tissue), the kidney (including renal cell, carcinoma tissue), as well as breast, lung, pancreas, uterus, and brain tissue, among others.

In one aspect, the energy source can be a thermal energy source. In one aspect, the non-thermal energy source can be selectively energizing for a desired period of time. More particularly, the period of time can be a predetermined period of time. In yet another aspect, the period of time can be a plurality of predetermined periods of time. In one aspect, the thermal energy source is selected from the group consisting of radiofrequency (RF), focused ultrasound, microwave, lasers, thermal electric heating, traditional heating methods with electrodes using DC or AC currents, and the application of heated fluids and cold therapies (such as cryosurgery). RF energy is known in the art for effective use in tumor ablation, though it is clear that any form of temperature-mediated continuous ablation could be used at settings known the art. In one aspect, after the energy delivery device is inserted into target organ 44, tissue 43 is ablated, and the energy delivery device is withdrawn. In one aspect the thermal energy source 7 can be an alternating current thermal energy source. In yet another aspect, the thermal energy source 7 is a direct current thermal energy source.

In one aspect, the electrode(s) can start at the point of non-thermal ablation of the target region. In one aspect, thermal ablation can be initiated at the start of the electrode chain (length wise on the catheter), which in one embodiment is applied to prevent abrehent tissue conduction. As the energy delivery device or electrode is withdrawn, thermal energy can be applied through the electrode to the target tissue. In one aspect, the electrode is selectively energized with thermal energy or nonthermal to ablate tissue adjacent the electrode track and proximate to a boundary of the tissue ablated.

In one aspect, IRE treatment of target tissue, followed by thermal ablation of at least one tissue area can be performed during procedures such as, but not limited to, cardiac, laparoscopic procedures and open surgical procedures. In one aspect ablation track can be ablated during the repositioning or dragging of a electrodes. In one aspect, after delivery of IRE energy to the target tissue, an ablated region of tissue remains. In one aspect, ablated region of tissue includes target tissue region and the surrounding area of tissue. In one exemplary embodiment, after treatment of the target tissue using IRE, treatment parameters can be reset to bring about thermal track ablation. In one aspect, after IRE treatment of the target tissue, the energy delivery device or electrodes is repositioned. In one aspect, upon termination of the energy delivery (and in some cases repositioning) of the energy delivery device ablate tissue in a different area/location, a tissue track is coagulated and bleeding can be prevented. In one aspect thermal energy, such as, but not limited to RF energy, can be applied to the ablation track during the ablation cycle. In another aspect the track ablation zone is created to stop bleeding. It is important to prevent bleeding so as no clots are formed, especially during procedures that could involve ablation in the left-side of the heart.

In one aspect, the generator, or single power source 4, used during the thermal ablation procedure can be configured to have various ablation settings and capabilities. In one exemplary aspect, the Arga 1000 generator described above can be used as an RF energy source. In one aspect, the RF energy source can be used to ablate tissue using 10-100 watts of power. In other exemplary aspects, one of ordinary skill in the art would recognize that smaller or larger amounts of power can be used in various embodiments, as necessary, in order to provide ablation. In one exemplary embodiment utilizing the generator, the RF power source can provide AC power in addition to being used for ablation, while the IRE power source can be used to provide DC power.

In one aspect, if a thermal energy source is used, it could be used with a variety of techniques to bring about tissue ablation. In one exemplary aspect, additional embodiments can involve ablation performed using one or more of radiofrequency (RF), focused ultrasound, microwaves, lasers, thermal electric heating, traditional heating methods with electrodes using DC or AC currents, and application of heated fluids and cold therapies, such as, but not limited to, that used in cryosurgery. In one aspect h heat energy can be delivered in certain embodiments via pulses that can be in a range of about 35 microseconds to about 10 seconds. In other exemplary embodiments the at least one energy source can be configured to release or deliver at least one pulse of heat energy in a range of about 35 microseconds to about 1 second. In yet another exemplary embodiment, at least one energy source can release or deliver at least one pulse of energy for between about 35 microseconds to about 1000 microseconds. In yet another exemplary embodiment, at least one pulse can be delivered in a range of from about 1 microsecond to about 100 microseconds.

In one exemplary embodiment thermal energy can be applied such that it produces fluctuations in temperature to effect treatment. In one aspect, the thermal energy provided to the tissue can heat the target tissue to between about 46 degree C. and about 70 degrees C. to bring about cell death. In one aspect the temperature can be adjusted such that it can be lesser or greater than this temperature range, depending on the exact rate of speed of removal of the heat generated via externally supplied fluid and/or blood from the target tissue. In one embodiment the temperature used is between about 50 degrees C. and about 100 degrees C., although one of ordinary skill would recognize that temperatures above about 100 degrees C. can cause tissue vaporization. Ellis L, Curley S, Tanabe K. Radiofrequency Ablation for Cancer; Current Indications, Techniques, and Outcomes, NY: Springer, 2004. In one exemplary embodiment, thermal energy can be used to ablate approximately 2-3 mm of tissue. In one aspect this tissue thickness can be varied depending upon various factors, such as, but not limited to, the condition of the target tissue, the various parameters used, and the treatment options.

In one embodiment the mechanisms through which the user sets the parameters for bringing about IRE effects are changed to bring about thermal results through thermal heating that is resistive heating. In certain embodiments the mechanisms are reset such that DC energy is applied to bring about thermal ablation. In one exemplary embodiment, ablation can be performed using DC current. In one aspect, the DC current can be used for heating the target tissue. In one aspect, at least one pulse of DC current can be delivered in one direction. In yet another aspect, at least one pulse of DC current can be delivered from the opposite direction of an electrical circuit. In one aspect, DC current can be applied such that the temperature of the tissue can be between about 42 degrees C. and about 75 degrees C. In one aspect, the DC current can be applied such that thermal damage is induced at a temperature as low as about 42 degrees C. In yet another aspect, as the rate of probe removal increases, the DC current can be applied to the target tissue such that the temperature can be from about 42 degrees C. to about 75 degrees C. Davalos R, Mir L, Rubinsky B. Tissue Ablation with Irreversible Electroporation. Annals of Biomedical Engineering, Vol. 33(2):223-231 (2005).

One of ordinary skill in the art would recognize that various lengths of DC pulses can be applied to bring about effective track ablation. In yet other embodiments, AC pluses can be applied as the energy delivery device is removed from the target tissue in stages. In summary, the method for selectively ablating tissue involves providing at least one energy source, such as a generator, described above. In one aspect, the at least one energy source, or single power source 4, can comprise at least a non-thermal energy source 6 and a thermal energy source 7, providing at least one probe, or at least one ablation catheter 1, that is configured to be selectively manually operatively coupled to a desired energy source of the at least one energy source, positioning, via a electrode, at least a portion of the at least one electrode within a desired region of a target tissue. In one aspect, the selective coupling of the electrodes to the thermal energy source comprises the actuating a switch 40 to operatively select between the non-thermal energy source 7 and the thermal energy source 8. Then at least one probe is selectively coupled to the non-thermal energy source, and the non-thermal energy source is selectively energized to apply non-thermal energy from the non-thermal energy source to at least a portion of the desired region to ablate at least a portion of the desired region, selectively coupling the at least one probe to the thermal energy source, withdrawing the at least probe from the desired region, and selectively energizing the thermal energy source to apply thermal energy during at least a portion of withdrawal of the at least one probe to ablate tissue substantially adjacent to the probe track. In one aspect, prior to selectively coupling the at least one probe to the thermal energy source, the at least one probe is operatively decoupled from the non-thermal energy source.

In one aspect, one pulse can be longer in duration than any of the pulses in but which mediate thermal heating via resistive heating. Also, the thermal heating can be brought about by changing energy modes such that the pulses are greater in number or shorter, the pulses are different length, the dwell between pulses is also changed to adapt to the tissue being ablated and the BIO feedback acquired from the system. It is also conceivable to alter one or both the voltage as well as pulses to increase or decrease either or both (including having the option to vary time between pulses) to bring about thermal effects for track ablation. In certain embodiments the change from pulses leading to IRE effects the pulse or pulses leading to thermal effects are used to bring about IRE and thermal effects on tissue where both effects are within the target region. Also, in certain embodiments the order of application of pulses and pulse or pulses switching in the target region or in the tissue or both to most effectively treat the patient. Also, pulses and pulses or pulses chains can be used in conjunction with thermal heating methods such as Radiofrequency such that nonthermal IRE effects, effects from resistive heating due to DC current changes, and thermal heating effects from AC current (such as RF) can be brought about in any order in target tissue or in a tissue track for the benefit of the patient. For example, the mitral isthmus tissue can be treated with IRE or RF (or other AC as well as other DC pulses leading to resistive heating) or more than one of these in any order so as to ablate the target tissue or tissues and control bleeding or coagulate or ablate vessels or cells, and then upon probe removal, IRE or RF (or other AC as well as other DC pulses leading to resistive heating) pulses can be uses as necessary together or independently in any order to control bleeding, coagulate or ablate tissue, vessels, tumor cells, or to ablate or treat tissue surrounding the tissue. In certain embodiments the changes between treatments or treatment methods can be brought about using a mechanism or device or system for altering or changing one or more parameters herein described via an energy source; the source could have one or more generators coupled and parameters could be determined using mechanisms of a system or a generator or energy source, and the mechanisms could have control components allowing user changes from a probe directly or from the energy source directly.

REFERENCES

Mali B, Jarm T, Snoj M, Sersa G, Miklavcic D. Antitumor effectiveness of electrochemotherapy: A systematic review and meta-analysis. Eur J Surg Oncol. 2013; 39:4-16.

Heller R, Heller L C. Gene Electrotransfer Clinical Trials. Adv Genet. 2015; 89:235-62.

LIST OF REFERENCE NUMERALS

1 ablation catheter OR energy delivery system OR energy delivery device OR probe OR multi-electrode and multi-functional ablation catheter
3 system for selectively ablating tissue
4 single power source OR energy source OR energy delivery source OR generator
5 battery powered generator
6 non-thermal energy source
7 thermal energy source OR alternating current thermal energy source OR direct current thermal energy source
8 means for selectively coupling the probe to one desired energy source of the at least one energy source OR mechanism for coupling the probe to one desired energy source OR probe connector
9 positive connector
10 negative connector
11 means for selectively energizing the non-thermal energy source
12 means for selectively energizing the thermal energy source
13 elongate shaft
14 elongate shaft proximal portion
15 elongated shaft proximal end
16 elongate shaft distal end
17 elongated shaft distal portion
18 elongated shaft distal portion proximal end
19 elongated shaft distal portion distal end
20 shaft ablation assembly OR functional element fixedly mounted to the distal portion
21 distal ablation assembly OR tip ablation element OR Tip OR mandrel with electrodes
22 shaft ablation element OR electrode OR single/multiple ablation element
23 tip ablation element
24 deflection shapes and geometries of the distal portion OR deflection geometries
25 steering wire (configured to deflect the distal portion in the one or more deflection directions)
26 shape setting mandrel OR deflection assembly (to maintain deflections in a single plane)
27 asymmetric joint (between two elongate shaft portions)
28 integral member
29 variable braid OR steering wires
30 control port OR aperture on the tip of the elongate shaft
31 single ablation element OR ablation element (suitable for RF and Irreversible Electroporation) OR electrode
32 multiple ablation elements OR electrodes
33 shape setting mandrel carrier assembly OR shape setting mandrel OR deflection assembly OR mandrel
34 control shaft OR prossimal portion of the mandrel
35 shaft outer diameter
36 ablation electrodes/ablation elements outer diameter

37 thermocouple
38 means of dissipating heat (such as increased surface area)
39 set of electrode tips
40 switch to operatively select between the non-thermal energy source and the thermal energy source
41 tissue
42 ablated tissue
43 heart
44 organ
45 ablating region OR desired region
100 ablation assembly or equipment
101 monopolar probe OR ablation catheter having monopolar solution OR ablation catheter having a monopolar arrangement of the at least one electrode
102 bipolar probe OR ablation catheter having a bipolar arrangement of the electrodes
103 handle
104 electrode proximal end
105 electrode distal end
106 distal electrode
107 round electrodes
108 grounding pad
109 electrical circuit
110 needle
111 electrode array OR orderly arrangement of multiple probes
112 multiple selectively activatable electrode patterns.
113 monopolar electrode
114 bipolar electrode
115 first electrode OR most distal portion electrode
116 second electrode OR proximal electrode
117 spacer
118 inner lumen (2nd Lumen—multi-purpose (fluid flush and shape setting mandrel))
119 mandrel elastic body
120 catheter bend portion
121 mandrel heating element
122 mandrel locking mechanism
123 retention element
124 locking seat
125 ball-tip
126 shaft transition portion
127 shaft electrodes
128 electrode tip/atraumatic tip
130 small electrode
131 large electrode
132 mandrel electrodes
134 set of shape fitting mandrel
135 first shape setting mandrel
136 second shape setting mandrel
138 mandrel proximal portion
139 mandrel distal portion
140 mandrel seat
141 inner lumen neck portion
142 wire proximal extension
143 wire gripping portion
144 steering device
145 steering device through hole
200 Kit of ablation catheter and set of mandrels
201 pulse
202 pulse amplitude
203 pulse duration
204 pulse train
205 gap of time between adjacent pulse trains
206 energizing period of time
207 catheter elongated shaft flexible body=flexible body

208 body vessels
209 number of pulses
210 wire
300 kit of ablation catheters
400 single control unit
401 power unit
402 power module
403 drive circuit block
404 selecting block
405 filtering block
406 electrical isolation block
407 Microprocessor
408 variable High Voltage Power Supply block
409 Programmable Logic Controller block
410 Video interface block
411 Watch Dog block
412 Audio interface block
S electric signal
Vcc supply voltage signal
N insulated conductive portions of an electrode
IRE irreversible electroporation
RF radiofrequency
X-X elongate shaft longitudinal main direction
P shaft distal portion plane
ALFA acute angle
410' Push Button block
114*a* first electrode
424 electrode body
114*b* second point-like electrode
210*a* first wire
210*b* second wire
425 ground electrode

The invention claimed is:

1. An ablation assembly to treat target regions of a tissue in organs comprising:

an ablation catheter comprising an elongate shaft having a longitudinal main direction (X-X), said elongate shaft comprising at least a shaft distal portion, said shaft distal portion comprising a shaft distal portion distal end;

said ablation catheter comprising an inner lumen arranged within the elongate shaft;

said ablation catheter comprising a shaft ablation assembly fixedly disposed at said shaft distal portion, the shaft ablation assembly being configured to deliver both thermal energy for ablating said tissue and non-thermal energy for treating said tissue;

at least a shape setting mandrel disposed within the ablation catheter, the shape setting mandrel being insertable within the inner lumen and removable from the inner lumen, wherein the shape setting mandrel is free to move in respect of the inner lumen avoiding any constraint with said shaft distal portion during the shape setting mandrel insertion, wherein the shape setting mandrel comprises at least a pre-shaped configuration and the shape setting mandrel is reversibly deformable between at least a straight loaded configuration and said pre-shaped configuration, wherein, when the shape setting mandrel is fully inserted in the shaft distal portion, the shape setting mandrel is configured to shape set said shaft distal portion with said pre-shaped configuration, wherein said shape setting mandrel comprises a mandrel distal portion, wherein said mandrel distal portion comprises a mandrel seat, wherein a retention element is fixed to said shape setting mandrel and partially housed in said mandrel seat, wherein said inner lumen proximal to said shaft distal portion distal end presents a neck portion, and wherein said retention element interferes with said neck portion to lock said shape setting mandrel in a mandrel fully inserted position.

2. The ablation assembly of claim 1, wherein said shape setting mandrel comprises a mandrel proximal portion, wherein said mandrel proximal portion is disposed outside said inner lumen so that said shape setting mandrel is drivable by a user, wherein said elongate shaft comprises a shaft proximal end, wherein said ablation catheter comprises a steering device attached to said shaft proximal end, wherein said ablation catheter comprises a handle, wherein said steering device is connected to said handle and is drivable in rotation with respect to said handle so that a rotation of said steering device with respect to said handle causes a rotation of said elongate shaft.

3. The ablation assembly of claim 2, wherein said steering device comprises a through hole in communication with said inner lumen, wherein during insertion or removal of the shape setting mandrel within or from said ablation catheter said shape setting mandrel passes through said through hole, and wherein when the shape setting mandrel is fully inserted in the shaft distal portion, said mandrel proximal portion is outside said steering device, and/or wherein, when the shape setting mandrel is fully inserted in the shaft distal portion, said shape setting mandrel deforms said shaft distal portion at least in a shaft distal portion plane (P), wherein said steering device comprises at least two protrusions, wherein said at least two protrusions and said shaft distal portion plane (P) are coplanar to help a user to handle the catheter assembly.

4. The ablation assembly of claim 1, wherein said ablation catheter comprises at least one steering wire configured to deflect the shaft distal portion in one or more deflection directions, wherein said at least one steering wire is fixedly connected to said shaft distal portion, wherein said at least one steering wire comprises a wire proximal extension that is arranged outside with respect to a shaft proximal portion, wherein said wire proximal extension comprises a wire gripping portion configured to pull at least one the steering wire for steering the shaft distal portion with shape setting mandrel fully inserted into the shaft distal portion.

5. The ablation assembly of claim 4, wherein said shaft distal portion comprises a shaft distal portion proximal end, wherein said ablation catheter comprises at least two steering wires.

6. The ablation assembly of claim 5, wherein a first steering wire of said at least two steering wires is fixedly connected proximal to the shaft distal portion distal end;

and/or wherein a second steering wire of said at least two steering wires is fixedly connected proximal to the shaft distal portion proximal end;

and/or wherein a third steering wire of said at least two steering wires is fixedly connected proximal to the shaft distal portion distal end;

and/or wherein a fourth steering wire of said at least two steering wires is fixedly connected proximal to the shaft distal portion distal end.

7. The ablation assembly of claim 1, wherein when the shape setting mandrel is fully inserted in the shaft distal portion defines said mandrel fully inserted position, wherein said ablation assembly comprises a locking mechanism configured to lock said shape setting mandrel to said shaft distal portion when said shape setting mandrel is in said mandrel fully inserted position.

8. The ablation assembly of claim 7, wherein said locking mechanism comprises said retention element that reversibly locks said shape setting mandrel in said mandrel fully inserted position, and wherein said retention element is configured to release said shape setting mandrel from said mandrel fully inserted position when a pull force is applied to said shape setting mandrel;

and/or wherein said retention element is made of metal, metal alloy, rubber or polymer; and/or wherein said shape setting mandrel comprises a ball-tip configured to engage said retention element when said shape setting mandrel is in said fully inserted position.

9. The ablation assembly of claim 7, wherein said retention element is an O-ring, wherein said mandrel seat is toroidal.

10. The ablation assembly of claim 1, comprising a distal ablation assembly disposable at least at said shaft distal portion distal end, said distal ablation assembly being configured to deliver both thermal energy for ablating said tissue and non-thermal energy for treating said tissue, wherein said distal ablation assembly comprises at least an electrode tip disposable at least at said shaft distal portion distal end, wherein said shaft electrodes are arranged along the shaft distal portion spaced apart from each other and/or wherein said shaft ablation assembly (20) is configured also to map a tissue.

11. The ablation assembly of claim 10, wherein at least one of said shaft electrodes comprises at least two conductive portions (N) electrically isolated from each other, wherein each conductive portion (N) covers radially less than 180° around the shaft distal portion and/or wherein at least one of said shaft electrodes comprises at least four conductive portions (N) electrically isolated from each other, wherein each conductive portion (N) covers radially less than 90° around the shaft distal portion.

12. The ablation assembly of claim 10, wherein when the shape setting mandrel is fully inserted in the shaft distal portion define said mandrel fully inserted position, wherein the shaft distal portion distal end is open and the shape setting mandrel is slidable outside said shaft distal portion distal end from said mandrel fully inserted position to a mandrel maximum exposed position, wherein the shape setting mandrel comprises a mandrel distal portion, wherein said distal ablation assembly is fixedly disposed at said mandrel distal portion, wherein said distal ablation assembly comprises a plurality of mandrel electrodes, wherein said mandrel electrodes (132) are axially spaced along said mandrel distal portion.

13. The ablation assembly of claim 12, wherein when said shape setting mandrel is in said mandrel fully inserted position, the shaft electrodes are electrically connected with at least a part of the plurality of mandrel electrodes;

and/or wherein when said shape setting mandrel is in said mandrel maximum exposed position the shaft electrodes are electrically disconnected from any electrical source.

14. An ablation assembly to treat target regions of a tissue in organs comprising:

an ablation catheter comprising an elongate shaft having a longitudinal main direction (X-X), said elongate shaft comprising at least shaft distal portion, said shaft distal portion comprising a shaft distal portion distal end;

said ablation catheter comprising an inner lumen arranged within the elongate shaft;

said ablation catheter comprising a shaft ablation assembly fixedly disposed at said shaft distal portion, the shaft ablation assembly being configured to deliver both thermal energy for ablating said tissue and non-thermal energy for treating said tissue;

said assembly comprising a distal ablation assembly disposable at least at said shaft distal portion distal end, the distal ablation assembly being configured to deliver both thermal energy for ablating said tissue and non-thermal energy for treating said tissue;

at least a shape setting mandrel disposed within the ablation catheter, the shape setting mandrel being insertable within the inner lumen and removable from the inner lumen, wherein the shape setting mandrel is free to move in respect of the inner lumen avoiding any constraint with said shaft distal portion during the shape setting mandrel insertion, wherein the shape setting mandrel comprises at least a mandrel distal portion, wherein said distal ablation assembly is fixedly disposed at said mandrel distal portion, wherein the shape setting mandrel comprises at least a pre-shaped configuration and the shape setting mandrel is reversible deformable between at least a straight loaded configuration and said pre-shaped configuration, wherein the shape setting mandrel is slidable outside the shaft distal portion distal end from a mandrel fully inserted position to a mandrel maximum exposed position, wherein in said mandrel fully inserted position, the mandrel is in said loaded straight configuration, wherein in said mandrel maximum exposed position, the mandrel is in said pre-shaped configuration, wherein said mandrel distal portion comprises a mandrel seat, wherein a retention element is fixed to said shape setting mandrel and partially housed in said mandrel seat, wherein said inner lumen proximal to said shaft distal portion distal end presents a neck portion, wherein said retention element interferes with said neck portion to lock said shape setting mandrel in said mandrel fully inserted position.

* * * * *